(12) United States Patent
Bruetting et al.

(10) Patent No.: US 6,513,365 B1
(45) Date of Patent: Feb. 4, 2003

(54) MEASUREMENT OF PHYSICAL CHARACSTERISTICS OR PHYSICAL PROPERTIES OF VISCOUS MEDIA BY MEANS OF RAYLEIGH WAVES

(75) Inventors: Christian Bruetting, Marktredwitz (DE); Gerhard Lindner, Coburg (DE); Michael Kessler, Offenbach am Main (DE); Uwe Klippert, Oberaula (DE); Arnold Gallien, Coburg (DE)

(73) Assignee: Brose Fahrzeugteile GmbH & Co. KG, Coburg, Coburg (DE)

( * ) Notice: Subject to any disclaimer, the term of this patent is extended or adjusted under 35 U.S.C. 154(b) by 0 days.

(21) Appl. No.: 09/445,876

(22) PCT Filed: Jun. 12, 1998

(86) PCT No.: PCT/DE98/01645
§ 371 (c)(1),
(2), (4) Date: Mar. 30, 2000

(87) PCT Pub. No.: WO98/57163
PCT Pub. Date: Dec. 17, 1998

(30) Foreign Application Priority Data

Jun. 13, 1997 (DE) .......................... 197 25 012
Jun. 14, 1997 (DE) .......................... 197 25 290

(51) Int. Cl.[7] .......................... G01N 29/18; G01N 29/02
(52) U.S. Cl. ........................ 73/32 A; 73/61.49; 73/64.53
(58) Field of Search ............................ 73/19.03, 24.01, 73/24.06, 31.05, 31.06, 32 R, 32 A, 54.24, 54.25, 54.26, 54.27, 54.38, 54.41, 61.49, 64.53

(56) References Cited

U.S. PATENT DOCUMENTS

| | | | |
|---|---|---|---|
| 3,743,973 A | 7/1973 | Jones | 333/30 R |
| 4,691,714 A | 9/1987 | Wong et al. | 128/738 |
| 4,735,097 A | 4/1988 | Lynnworth | 73/861.28 |
| 4,767,719 A | 8/1988 | Finlan | 436/501 |
| 5,117,146 A * | 5/1992 | Martin et al. | 310/312 |
| 5,130,257 A * | 7/1992 | Baer et al. | 204/400 |
| 5,214,966 A | 6/1993 | Delsing | 73/861.28 |
| 5,283,037 A * | 2/1994 | Baer et al. | 310/311 |
| 5,321,331 A * | 6/1994 | Baer et al. | 310/313 B |
| 5,433,113 A | 7/1995 | Andoh et al. | 73/622 |

FOREIGN PATENT DOCUMENTS

| | | |
|---|---|---|
| DE | 126 118 | 6/1977 |
| EP | 0 527 176 | 2/1993 |
| EP | 0 542 469 | 5/1993 |
| EP | 0 621 462 | 10/1994 |
| JP | 06109710 | 4/1994 |
| JP | 09145692 | 6/1997 |
| SU | 1155915 | 1/1984 |
| WO | WO 92/01931 | 2/1992 |

OTHER PUBLICATIONS

O. Veilleux, "Oberflachenwellen–Bauelemente", Elektronic 14/1981, pp. 35–41 [partial English translation of pertinent portion only].

(List continued on next page.)

*Primary Examiner*—Hezron Williams
*Assistant Examiner*—Rose M. Miller
(74) *Attorney, Agent, or Firm*—Christie, Parker & Hale, LLP

(57) ABSTRACT

A method for measuring physical properties or characteristics of liquids uses an acoustic transfer system that utilizes Rayleigh waves. A wave guide with at least one test section formed from a solid surface made from non-piezo-electric material, contacts the liquid medium to be measured and/or a transfer system. A sender sends acoustic wave energy that includes at least one Rayleigh wave, and at least part of the acoustic wave energy leaving the sender passes at least once through a mode converter on its way to the receiver, whereby this part of its wave energy is converted at least partly from a Rayleigh wave (RW) into a volume sound wave (VW) or vice versa. The physical characteristics or physical properties of the liquid are then determined using changes of at least a parameter of the Rayleigh wave.

30 Claims, 36 Drawing Sheets

OTHER PUBLICATIONS

Figure 1A:
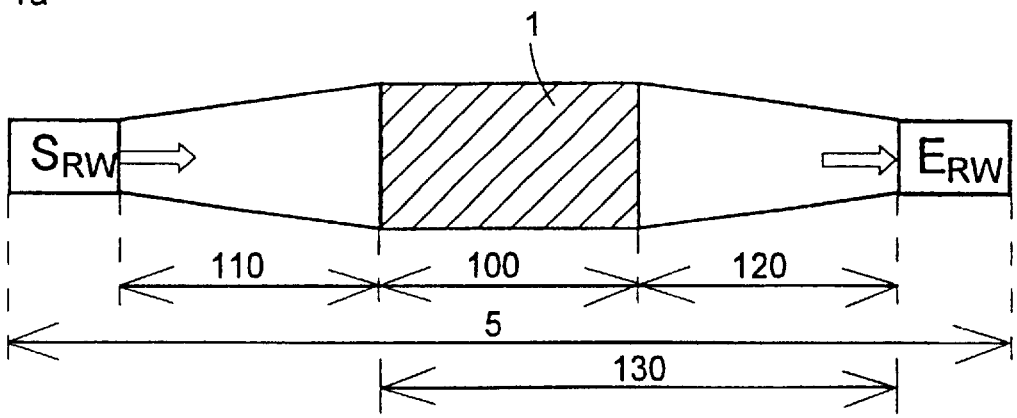

T. Nomura, et al., "Measurement and Mapping of Elastic Anisotropy of Solids Using a Leaky SAW Excited by an Interdigital Transducer", IEEE Transactions on Sonics and Ultrasonics, vol. SU–32, No. 2, Mar. 1985; pp. 235–240.

R. Lee, et al., Prototype Microwave Acoustic Fluid Sensors, 1988 Ultrasonics Symposium, pp. 543–548.

W. Gopel, et al., "Sensors", vol. 8, Micro–and Nanosensor Technology/Trends in Sensor Markets, vol. 8, pp. 148–149.

J. Kondoh, et al., "Multichannel Shear–Horizontal Surface Acoustic Wave Microsensor for Liquid Characterization", 1995 IEEE Ultrasonics Symposium, pp. 445–449 (on order).

R.M. White, et al., "Silicon Based Ultrasonic Microsensors and Micropumps" Integrated Ferroelectics, 1995, vol. 7, pp. 353–358 (on order).

R. F. Humphreys, et al., "Acoustic Bulk–Surface–Wave Transducer", Electronic Letters, May, 1969, vol. 5, No. 9, pp. 175–176 (*).

J. W. Grate, et a., "Acoustic Wave Microsensors", Analytical Chemistry, vol. 65, No. 21, Nov. 1993, pp. 940A–948A (*).

B. Jokoby, et al., "Properties of Love Waves: Applications in Sensors", PH:S0964–1726(97)87564–7, pp. 668–679 (*).

M. Rapp. et al., "Acoustoelectric Immunosensor Based on Surface Transverse Waves for In Situ Measurements in Water", The $7^{th}$ International Conference on Solid–State Sensors and Actuators, pp. 538–540.

S.J. Martin et al.; "Characterization of SH Acoustic Plate Mode Liquid Sensors", Sensors and Actuators, 20 (1989) pp. 253–268.

* cited by examiner

Fig. 1f
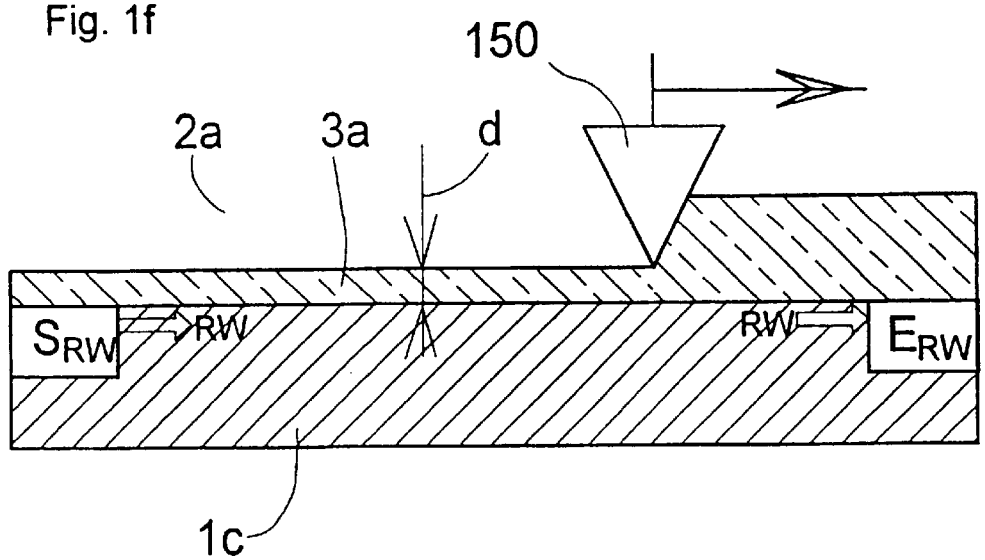
Fig. 1g
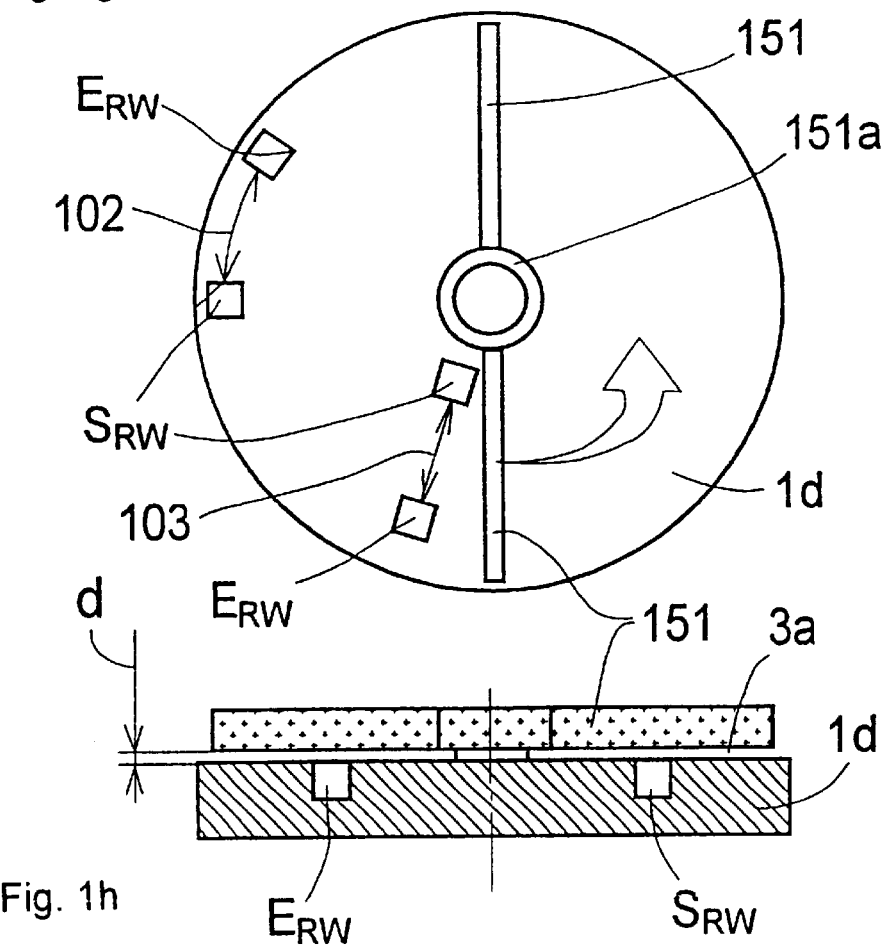
Fig. 1h

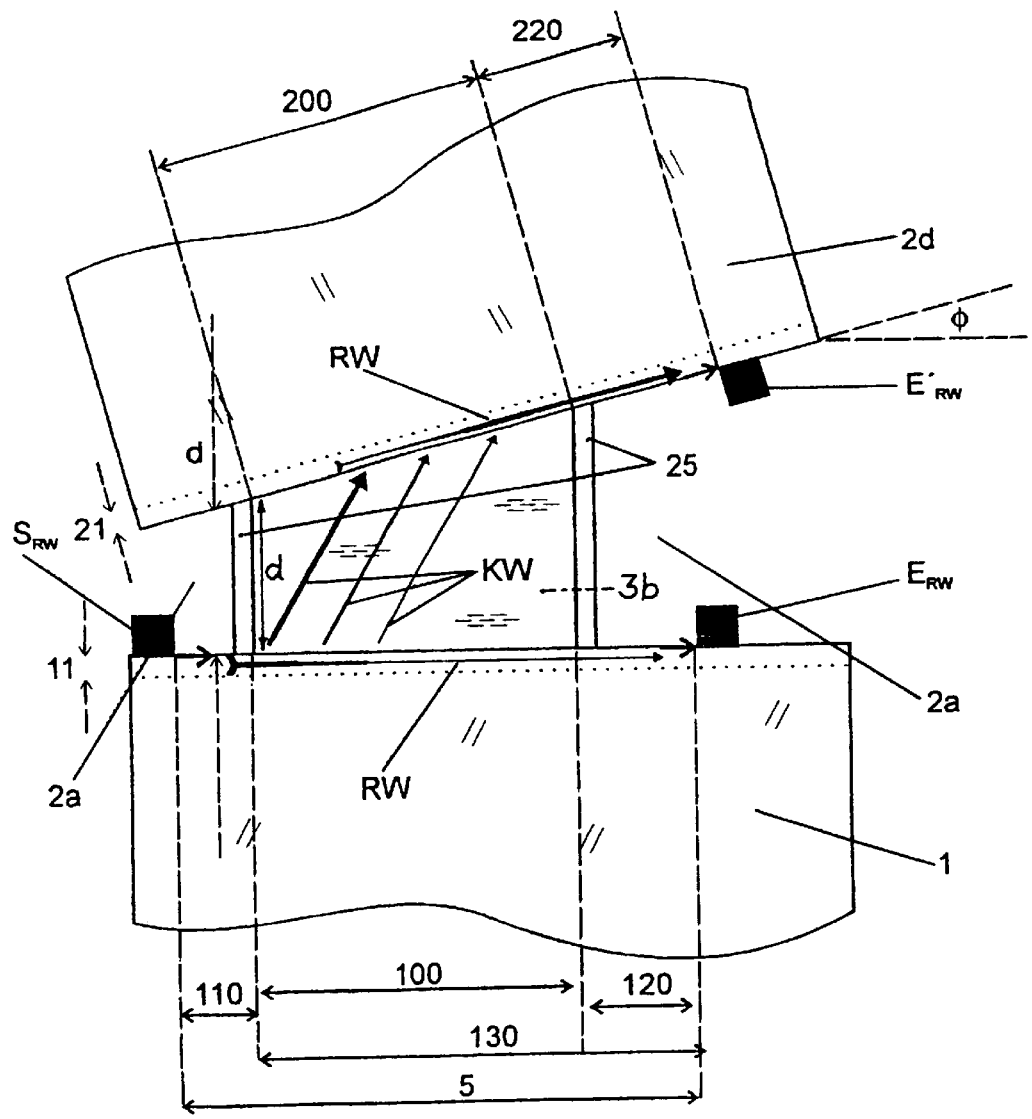

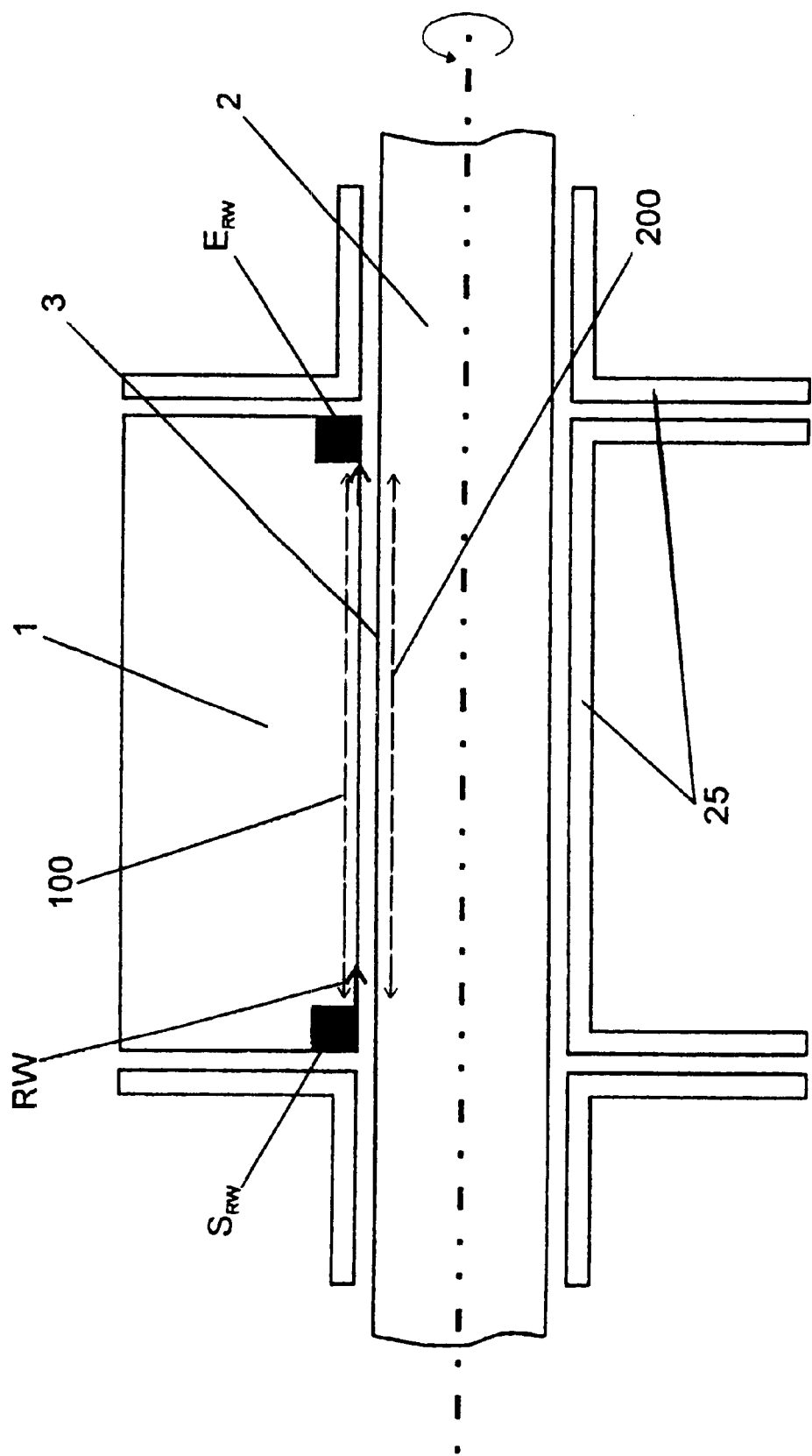

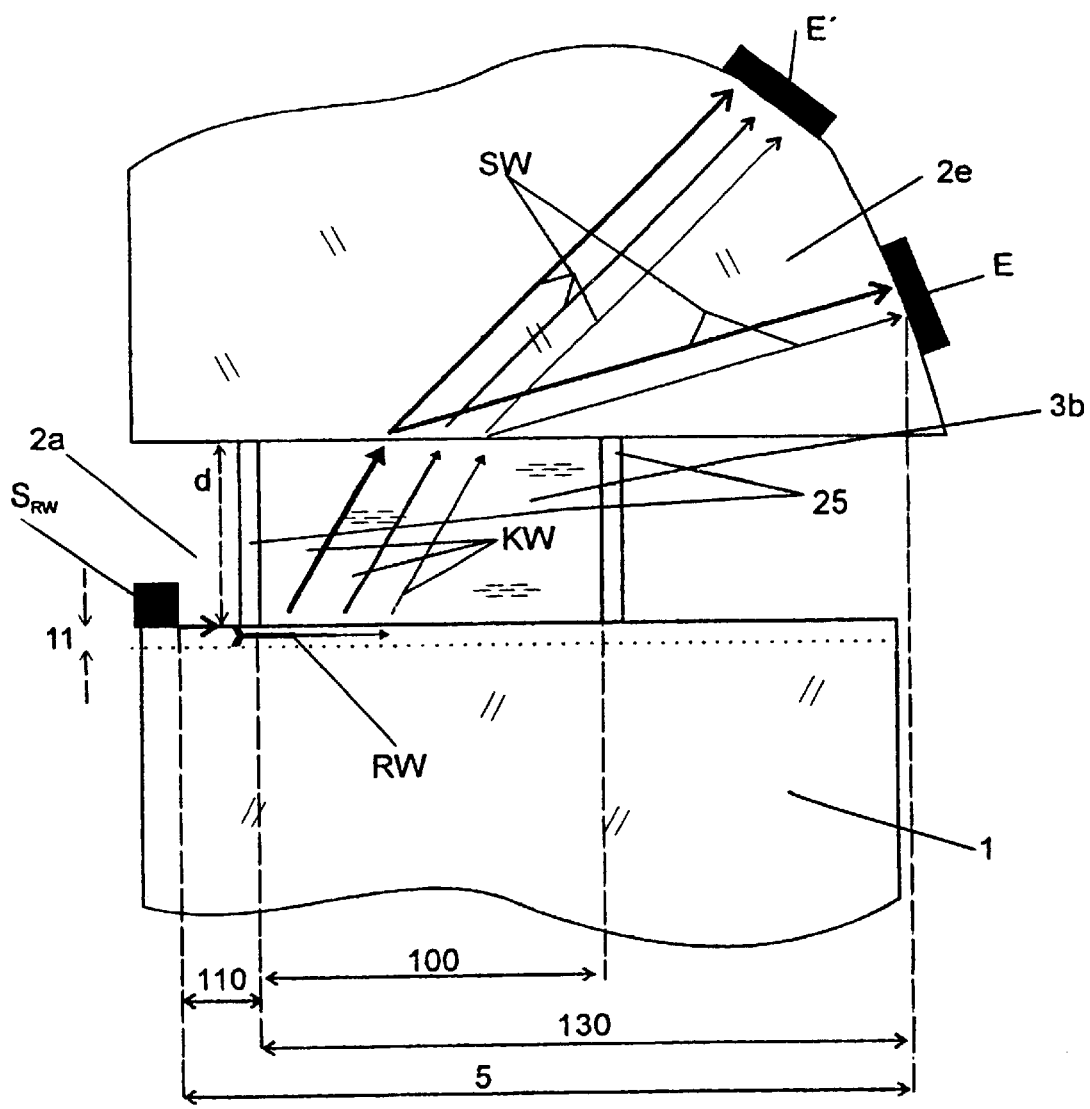

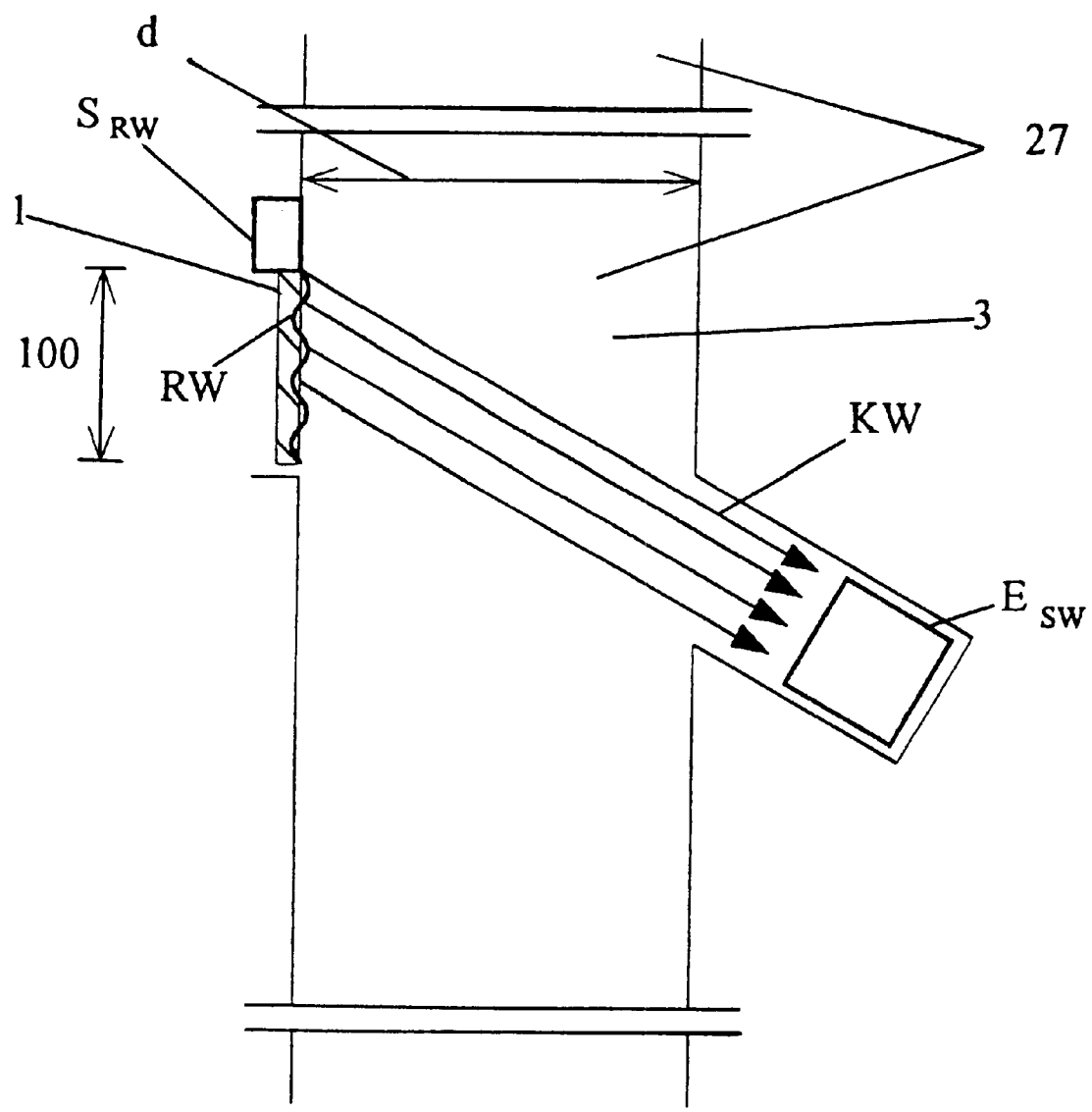

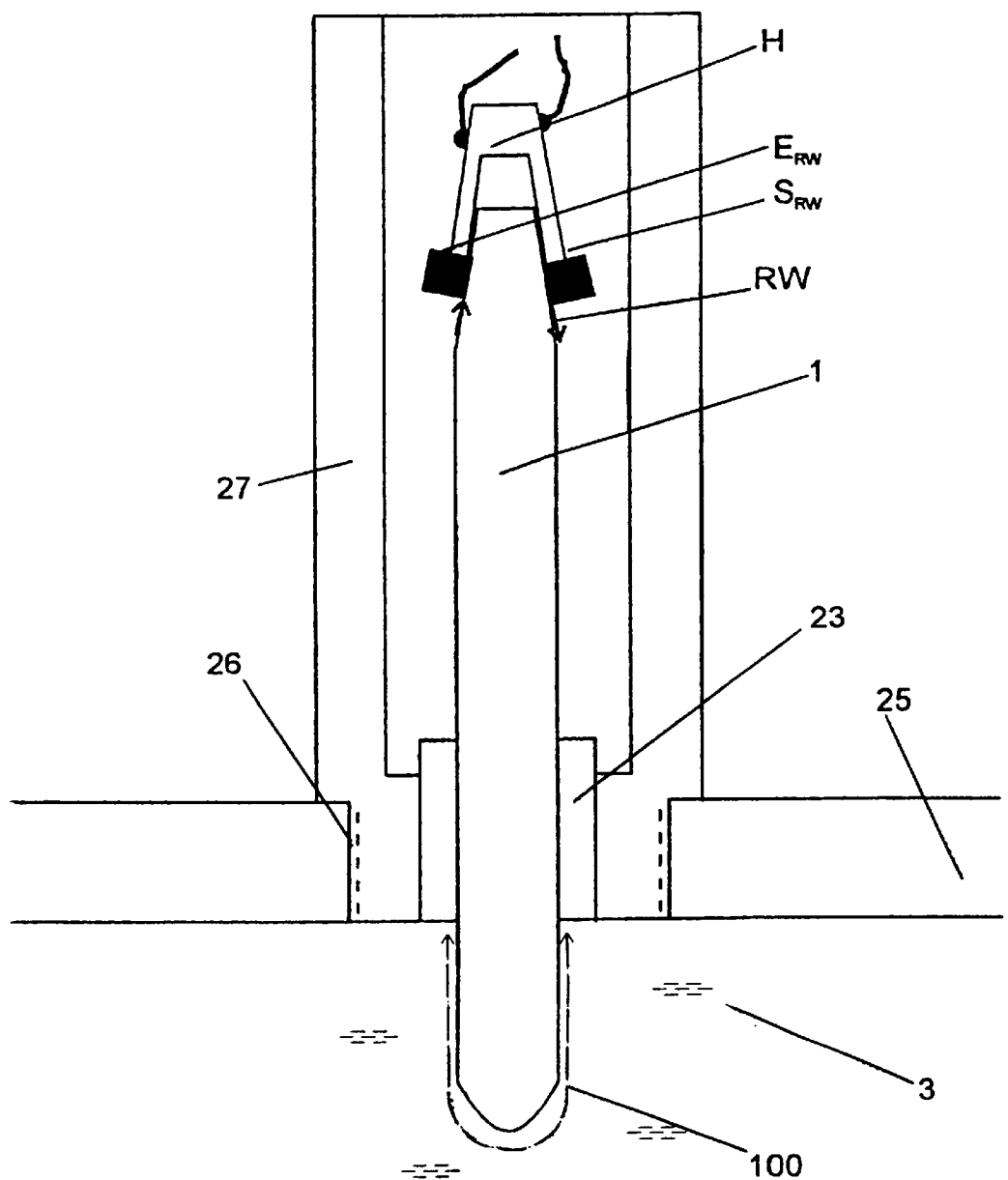

Grooves

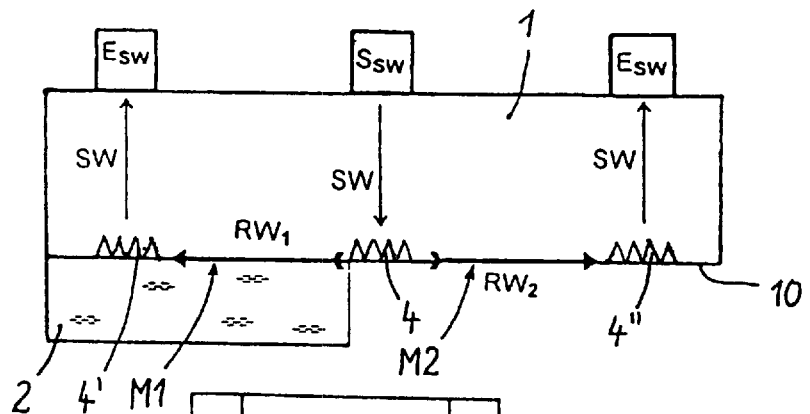
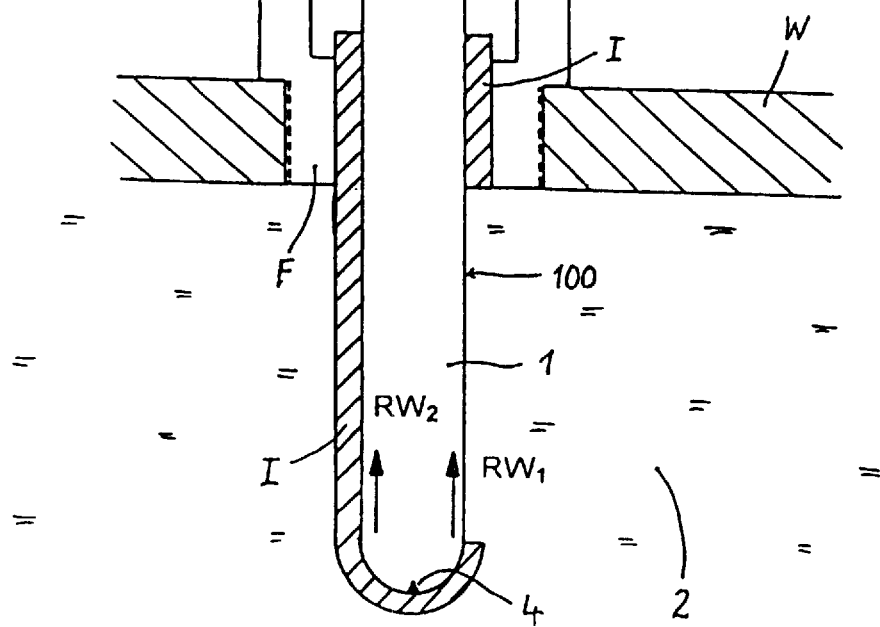

MEASUREMENT OF PHYSICAL CHARACSTERISTICS OR PHYSICAL PROPERTIES OF VISCOUS MEDIA BY MEANS OF RAYLEIGH WAVES

BACKGROUND OF THE INVENTION

The invention relates to a method for measuring physical characteristics or physical properties of liquids including highly viscous, doughy or paste-like mediums, using an acoustic transfer system (sender—test section—receiver) with at least one test section formed from a solid surface, which can be brought at least partly into contact with the medium to be measured. In addition, a device for implementing the method is described.

Conventional methods for measuring viscosity generally require the removal of a trial quantity which is tested in a separate measuring device. Particularly common are rotation viscosimeters, falling sphere viscosimeters and capillary viscosimeters which use the shear gradient in the liquid on the basis of the relative motion of at least one solid surface to the liquid. A disadvantage of these methods, however, is that they cannot be integrated into a technical process, which means that great resources are necessary for a correct measurement. Measurements of products whose properties are subject to a rapid transitory change or whose properties can be easily distorted by the removal of the trial quantity or the transportation of the trial quantity are particularly difficult and are often encumbered with errors.

A viscosity sensor which is suitable for on-line measurements is described in EP 0 527 176 B1. It consists of a cylindrical main body of piezo-electric material which is connected to an alternating current source and which is activated to torsional vibrations in the ultrasound field (20–100 kHz). The vibration properties (e.g. frequency) of the main body are changed by the contiguous liquid and converted into correspondingly altered electric signals. By evaluating these signals conclusions can be drawn regarding the viscosity. This technical solution, however, makes high demands upon the material of the main body and requires great resources in the manufacture of suitable materials and the geometrical formation of the main body.

In addition, scientific and patent literature has revealed various acoustic methods and devices which—using surface waves—are suitable for measuring physical and/or technical dimensions (i.e. physical characteristics or physical properties) of liquids. A common factor of these methods and devices is that they are generally limited to special materials (mainly piezo-electric material, whereby sender, test section and receiver form a centralized physical entity) for the substrate of the test section and/or they rely upon defined geometric conditions (thin plates) for the sensor surface. This gives rise to disadvantages concerning the adaptability of the suggested solutions to given technical conditions (e.g. temperature, corrosivity of the medium to be measured, constructive parameters, material of the transfer section, among other things).

J. Kondoh, K. Saito, S. Shiokawa, H. Suzuki; Multichannel Shear-Horizontal Surface Acoustic wave Microsensor for Liquid Characterization; 1995 IEEE Ultrasonics Symposium, pp 445–449 disclosed the use of shear surface waves (SH-SAW→SHEAR HORIZONTAL SURFACE ACOUSTIC WAVE) for determining substance properties in liquids. In this case, it is a question of a special type of surface waves characterized by particle deflections solely parallel to the wave-guiding solid surface and perpendicular to the propagation direction. i.e. there are no deflection components of the particles arising perpendicularly to the surface. Even this type of wave requires the use of a piezo-electric material (e.g. LiTaO$_3$), whereby the wave-guiding solid surface must be formed from a special crystal section.

R. M. White; Silicon Based Ultrasonic Microsensors and Micropumps; Integrated Ferroelectrics, 1995, vol. 7, pp. 353–358 describes a method for measuring viscosity using plate vibrations of a thin membrane of only a few micrometers on a silicon base. Membrane structures of this nature are, however, very sensitive particularly in relation to mechanical loads. Plate vibrations are characterized on the one hand by particle movements parallel to the surface in the propagation direction and on the other hand by particle movements perpendicular to the surface. For viscosity measurement, however, only the first-mentioned particle movements can be used.

JP 09145692 A discloses a water drop sensor for windscreens and side mirrors of vehicles or the like. The water-drop sensor consists essentially of a component (sender) generating surface waves and a component (receiver) receiving surface waves which is positioned at a distance therefrom on the surface of the body to be monitored. As soon as drops of water reach the propagation field of the surface waves between the sender and the receiver, there is a scattering of the surface waves and absorption of part of the wave energy. By means of an electronic switching circuit, an evaluation of the attenuation of the signal can be carried out. It is supposed to be possible to thereby control a windscreen wiper depending upon the quantity of water on a windscreen.

The described drop sensor can essentially only be used as a switch which triggers/does not trigger specified reactions on the basis of recognising the presence or absence of water. Due to the property of surface waves to uncouple into contiguous liquids, the measurement result—thus the degree of attenuation of the signal—depends to a large extent upon the distribution of the water on the sensed surface. Therefore, with a dormant surface, whereby upon leaving propagation paths for the surface waves the drops form local water collections, one expects a lower attenuation than with an agitated surface with the same quantity of water, whereby the drops are distributed to a more or less even layer. Should the dynamic forces working on the water drops be so great that on the surface only a liquid layer density can form which is smaller than a quarter of the wavelength of the compression wave in the liquid, then the desired attenuation effect would not come into play.

As could be shown, the measurement signal of the drop sensor is to be understood as a total value which does not allow a differentiation between the various interactions involved in its formation. Quantitative conclusions concerning concrete physical or technical dimensions, for example the viscosity of liquids, are impossible. On the other hand, with a comparatively strong, high-volume striking of the test section with water it is expected that the wave energy used is permanently almost completely uncoupled in such a way that it is not possible to obtain a measurement signal which can be analyzed quantitatively.

EP O 542 469 A1 discloses a sensor for determining the viscosity of a liquid. The sensor has a substrate forming a sensor surface (test section) which can be brought into contact with the liquid to be investigated. Acoustic energy is made available in the form of surface waves (STW) on the sensor surface. The wave components propagate predominantly within the surface itself and only have a negligibly small vertical component propagating into the liquid. Through the use of such waves, in particular horizontal shear waves, a situation is supposedly avoided where the surface waves are too strongly attenuated during their interaction with the liquid to produce a signal which can be evaluated.

U.S. Pat. No. 4,691,714 discloses a probe device for simultaneous determination of the viscosity and temperature of a liquid. This device has a plate in which volume waves propagate, which for the purpose of determining the viscosity of the liquid interact with the liquid on a first surface which can be brought into contact with the liquid, and on whose second surface—turned away from the first surface—acoustic surface waves propagate, whereby the propagation speed depends upon the temperature of the probe. As the temperature of the probe is in turn influenced by the temperature of the liquid to be investigated, the temperature of the liquid to be investigated can thereby be determined indirectly.

SUMMARY OF THE INVENTION

It is an object of the invention to develop a method and a device for measuring physical characteristics or physical properties of liquids including highly viscous, doughy or paste-like mediums, which, using an acoustic transfer system with at least one test section formed from a solid surface, can be easily adapted to the most varied conditions of tangible concrete technical applications. This is achieved in particular through a multitude of substrate materials which can be used for the test section, an essentially free formation of the geometrical parameters of the transfer system and the possibility of various activation mechanisms for generating acoustic waves.

Accordingly, at least a proportion of the acoustic energy transferred in the test section is made available in the form of Rayleigh waves, whereby the Rayleigh wave propagates on a test section made from non-piezo-electric material over at least 1/8, but preferably over 2l, wherein l is the wavelength of the Rayleigh wave. At least a proportion (sufficient for the measurement) of the acoustic wave energy remaining after the passage of the Rayleigh wave through one or several test sections in the measurement device is guided to and received by the receiver according to the principle of a wave guide, whereby the wave-guiding property begins at least at the beginning of the first test section (if the device has several test sections) and remains up until the receiver. i.e. the test section and the transfer path between the test section and the receiver must have a wave-guiding property. This includes both the transmission of the use signal gained in the test section with the fewest possible losses and the protection from unwanted disruptive influences. Influences on the use signal through the wave-guiding properties of the acoustic transfer system should preferably be known and ideally be optimized.

According to the invention, the wave-guiding property is provided at least between the beginning of the test section and the receiver. Otherwise, through the uncoupling of energy through the vertical component into the contiguous liquid, the information about the dimensions of the liquid to be measured which is obtained through the interaction of the Rayleigh wave with the liquid is also lost, and can therefore no longer be passed for evaluation. In order to measure the dimension of interest only, changes of at least one parameter of the Rayleigh wave are used, whereby preferably the dissipative energy loss of the Rayleigh wave in the test section is used as a basis. Essential embodiments of acoustic transfer systems with wave-guiding properties are examined in greater detail below.

The device developed to implement the method has at least one test section which can be brought at least partly into contact with the medium to be measured. This test section is suitable for forming and passing on Rayleigh waves at least a distance which corresponds to 1/8 of the Rayleigh wave generated. Moreover, the acoustic transfer system is formed at least between the beginning of the test section and the receiver of the wave energy according to the principle of a wave-guide.

Through the exclusive use of Rayleigh waves for the measurement effect, the wave-guiding is largely independent of the form stability of the carrier material. The largest part of the solid is able to pass on Rayleigh waves on its surface and thus to serve fundamentally as a test section/as an acoustic transfer medium between the sender and the receiver. As the largest part of the wave energy is transported in the boundary layer (penetration depth around l) between the solid surface and the contiguous liquid, and as the Rayleigh wave has a shear component of the movement of the surface, a test section at that boundary is particularly suitable for viscosity measurement with a favorable signal—noise ratio.

In the strict physical sense, Rayleigh waves can only occur on unlimited, even surfaces of a solid, which may however have no significance for technical applications. Rayleigh waves nonetheless occur under these limited conditions in such a way that they can definitely be used for technical measurement purposes. Rayleigh waves within the scope of the invention are also intended to include "distorted" Rayleigh waves which deviate from the "ideally" formed Rayleigh wave on the basis of the restrictions of the wave surface through geometric structures or boundary surfaces of materials of differing acoustic properties, or on the basis of the proximity to the sender, in whose immediate vicinity there is a not yet fully formed Rayleigh wave, or the like.

In addition the period duration of the Rayleigh wave can be determined by the construction of the transfer system and the choice of a suitable material for the test section such that the period duration is greater than the relaxation time of the liquid to be measured. For the purpose of viscosity measurement, the period duration should lie as close as possible to the relaxation time, which has a positive effect upon measurement accuracy.

When choosing materials for the purpose of adaptation to the particular application, one should consider the manufacture of alloys which are optimized in their composition or the change in elastic properties of the layer provided for passing on the Rayleigh wave, where the change is achieved through radiation with a beam which produces structural changes. Preferably, this radiation is nuclear radiation or particle radiation (e.g. neutrons), laser treatment, ion implantation or gas implantation (e.g. hydrogenation). With such precise adaptation of the wave-guiding bodies, the smallest changes in the medium to be measured, e.g. its composition, can lead to loss of equilibrium of the coupling/uncoupling behavior of the wave energy and can be used to draw corresponding conclusions.

It should be pointed out here that by using the so-called melting-spinning process, virtually any desired alloy can be produced. The basic idea of the method consists in quickly freezing the condition of a melt through shock cooling. This generally occurs by allowing a thin beam of liquid melt to run on a rotating, cooled drum, in such a way that with cooling speeds of around 1 million Kelvin per second, amorphous bands up to a density of around 0.1 millimeter are formed. However, the materials thus produced can only be used below their re-crystallization temperature.

In principle, the invention can be used to determine all those physical and/or technical dimensions of a liquid medium which influence the propagation properties of Rayleigh waves. The parameters which can be evaluated are thus the frequency, the phase speed and the amplitude of the Rayleigh waves as well as the physical characteristics or physical properties of the medium which are directly related thereto, like e.g. the viscosity or the density. Phase transitions such as those arising during "Betauung", freezing, boiling processes, cavitation or crystallisation can, however, also be detected. Further application possibilities are seen in the evaluation of non-homogenous liquids or as a humidification sensor or a cavitation sensor. For example, information concerning the condition of inner structures of non-homogenous liquids can be obtained. Preferably use is thereby made of the property of the Rayleigh wave to possess both shear components and vertical components of the movement in the boundary layer.

Although it is impossible to cite all possible application fields of the invention exhaustively, it should be pointed out that the invention can also be used in systems for process control and monitoring. This also applies for the monitoring of the condition and of the maturation process of electro-chemical aggregates, e.g. fuel cells, electrolysers and batteries. In chemistry and biotechnology, removal devices for substance trials could immediately provide information concerning the substance properties.

The multitude of the substrate materials that can be used not only gives rise to good adaptability to given thermal, chemical, electrical, optical and/or mechanical conditions. The good propagation conditions of Rayleigh waves allow in many cases the use of the boundary surfaces of an existing device, e.g. of a working device or a solid wall, as a carrier for the Rayleigh wave. In this connection with carrying, it is advantageous if senders and receivers can as required be removed from the test section/from the body carrying the test section or be re-connected thereto.

A further advantage of the invention is the straightforward facility for physical separation of the sender and receiver on the one hand and the test section (measurement location) of the system on the other hand, so that for example the sender and receiver do not have to be brought into the corrosive field of the medium to be measured. Between the sender/receiver and the measurement location, a comparatively large distance can be bridged. Even the good transferability of the Rayleigh waves from one carrier to another carrier through the intermediary of an incompressible coupling medium (e.g. a liquid) can be advantageously used for bridging distances.

For the purpose of producing and verifying Rayleigh waves, greatly differing mechanisms can be used, which further increases the adaptability of the invention. The following effects can be used for production and reception of Rayleigh waves:

Mechanical/acoustic activation

Mode conversion

Piezo-electric effect

Magnetic, in particular magnetostrictive effect (As the above-mentioned effects are reversible processes, these can be used for sending and receiving.)

Thermal activation through pulsed heating, e.g. with a laser (Effect can only be used for activating a wave.)

Optical effects, including magneto-optical and electro-optical effects.

Piezo-resistive effect (The two last-mentioned effects can only be used to detect a wave.)

Means of mode conversion can be used both between sender and measurement location (test section) and between measurement location and receiver. This is normally an advantage if between the measurement location and the sender/receiver, an acoustic transfer section must be provided which cannot be arranged to pass on Rayleigh waves or can only be arranged for this purpose with difficulty. For example, a compression wave emitted from a sender at the beginning of the test section is converted into a Rayleigh wave through means of conversion (these are suitable changes in the surface structure, e.g. indentations). This method can be used particularly advantageously for guiding wave energy through solid walls (pipes, container walls).

In order to ensure the wave-guiding property of the device according to the invention, there are at least three principal variants of the invention and the sub-variants thereof. They ensure that the uncoupling of acoustic energy out of the Rayleigh wave into the contiguous liquid is suppressed and that the uncoupled energy is so far as possible completely "captured" again and fed to the receiver:

Variant 1

Thin liquid layer (d lkw/4)

neighboring medium with varying acoustic impedance neighboring medium with the same acoustic impedance $V_{(1)RW} < V_{(2)RW}$ If the medium (medium (2)) neighboring the liquid layer which lies opposite the test section (medium (1)) has a very poor coupling ability (like e.g. vacuum, gases or foams), which results in a low degree of transmission and a high degree of reflection to this second boundary surface, the uncoupling of energy in the form of compression waves is avoided if the thickness d of the liquid layer is thinner than the liquid layer which is necessary to form the fundamental vibration of a stationary wave. With a layer thickness below $l_{KW}/4$ of the compression wave this condition is normally fulfilled.

If the layer thickness of the liquid is limited by a neighboring solid (contiguous medium (2)), the condition of total reflection for the (liquid) compression wave must also be fulfilled and that opposite material neighboring the liquid layer (contiguous medium(2)) must have a higher speed $V_{RW(2)}$ for the Rayleigh wave than the material of the test section (contiguous medium (1)) (like e.g. glass in relation to steel, aluminum).

Variant 2

Opposite-lying solid boundary surfaces with acoustic coupling, preferably when d>lKW/4 is supposed to apply $V_{(1)RW} = V_{(2)RW}$ when reciprocal activation of Rayleigh waves on parallel solid boundary surfaces is provided $V_{(1)RW} \neq V_{(2)RW}$ when the opposite-lying solids do not run in parallel, but their gradient is adapted to the differing Rayleigh wave speeds $V_{(1)RW} > V_{(2)RW}$ when the opposite-lying solidis supposed to pass on a volume sound (acoustic) wave The uncoupling of the energy of the Rayleigh wave from the first solid boundary surface(1), which is connected to the sender, into a liquid layer with a thickness d that may be greater than $l_{KW}/4$ of the compression wave, is used to couple the wave energy back to Rayleigh waves on a parallel opposite-lying second solid boundary surface(2), which forms a wave stretch with the same Rayleigh wave speed. For this purpose the sound speeds $V_{(1)RW}$ and $V_{(2)RW}$ of the first solid boundary surface(1) and the parallel opposite-lying second solid boundary surface(2) must be of equal size. From the Rayleigh wave induced on the second solid boundary surface(2) a compression wave is again uncoupled, which for its part on the opposite-lying first solid boundary surface(1) produces a Rayleigh wave again. Dependent upon the dimensions of the test section the process of the reciprocal wave activation can be formed with varying intensity. For the purpose of measuring the wave energy, the first and/or the second solid boundary surface can be provided with a receiver. The same effect can be achieved with differing Rayleigh wave speeds with adapted gradient of the boundary surfaces.

If, however, the sound speed $V_{(1)RW}$ of the first solid boundary surface(1) is greater than the sound speed $V_{(2)RW}$ of the parallel opposite-lying solid boundary surface(2), a volume sound wave is coupled into the opposite-lying solid, whereby this volume sound wave is passed into a receiver connected to this solid.

It is, however, also possible to detect directly by a receiver the compression wave uncoupled from the Rayleigh wave of the first solid boundary surface at a specified angle, and to use it for evaluating the liquid. The angle is determined by the speed $V_{RW(1)}$ of the Rayleigh wave in the test section and the sound speed $V_{KW}$ of the compression wave in the liquid.

Variant 3

Substrate material with slow Rayleigh wave speed ($V_{(1)RW} < V_{KW}$)

If the substrate material of the test section(1) has a sound speed $V_{(1)RW}$ for the Rayleigh wave which lies below the sound speed $V_{KW}$ of the contiguous liquidfl, no uncoupling of energy can take place which does not serve the technical measurement purpose. In relation to most liquids (water, many oils) possible substrate materials are for example synthetic materials, soft metals (gold, lead, bismuth) as well as graphite.

It is also conceivable to use elements with acoustic-optical properties, in order to favorably influence the wave-guiding property of the acoustic transfer system.

If not only information about the liquid to be measured is required, but it is also desired to influence the properties of the liquid—e.g. for the purpose of controlling complex process-technical installations or for the purpose of directly influencing substance-changing processes—it can be advantageous if in addition to the acoustic energy, energy of another kind is coupled into the contiguous liquid layer via the solid boundary surface of the test section. This occurs via a layer which forms the boundary surface of the test section, or via the solid carrying the test section. The layer/the solid can for example be electrically conductive and be connected to a direct or alternating current source. If the liquid neighboring the test section is a polar or an electro-rheological liquid and/or a liquid with constituent parts dissociated in ions, the typical respective interactions occur in an electrical stress field. i.e. the molecules of polar liquids position themselves correspondingly in the stress field; ions migrate to electrodes with an opposite load and are discharged there if there is a sufficiently high voltage; electro-rheological liquids lose their viscosity.

It is, however, also possible to connect the layer forming the boundary surface of the test section or the solid carrying the test section to a heat source, in order to heat the contiguous liquid layer. If this layer or a layer positioned in the vicinity of the boundary surface is electrically conductive, a connection to an electrical voltage source will allow the layer to be influenced according to the principle of resistive heating.

If constituent parts of the liquid display photo-optical reactions, exertion of influence through coupling of light quanta is appropriate. For this purpose, it is recommended that the layer forming the boundary surface of the test section or the solid carrying the test section should be made to be optically permeable and that it should be connected to an energy source producing light quanta, e.g. a laser source.

According to a further embodiment of the invention, at least a part of the acoustic wave leaving the sender traverses a mode converter at least once on its way to the receiver, in order to convert its mode from a Rayleigh wave into a volume sound wave or vice versa. Through the use of mode converters it is possible to activate Rayleigh waves for measurement purposes on surfaces which are not accessible in themselves, whereby acoustic energy is passed for example through solid components, walls or similar and is converted to Rayleigh waves on the mode converter. The Rayleigh waves encumbered with the measurement information can in turn be converted into another wave mode and be forwarded to a receiver positioned at a distance from the measurement location.

The invention allows the measurement device to be formed in such a way as to ensure that senders and receivers can always be positioned outside the area in which the liquid to be measured is situated. Through the geographical separation of the test section on the one hand and the sender and receiver on the other hand, the best conditions arise for adapting the measurement device to the respective application. Furthermore, the pressures of the sender and receiver through thermal, chemical, mechanical or other influences are thereby considerably reduced/completely avoided. In many cases it will be possible to use the boundary surfaces formed from receptacle walls as a test section for acoustic waves (volume sound waves).

Accordingly, a mode converter is in an operational connection with the test section or with a field which is connected conductively to the acoustic Rayleigh waves, whereby the mode converter converts a volume sound wave running to the test section into a Rayleigh wave and/or a Rayleigh wave running back to the receiver into a volume sound wave. Mode converters are constituted by periodically positioned geometric structures whose division of wavelength I corresponds to the Rayleigh wave to be generated. Such geometric structures can for example be series of holes or wedge-like formations.

It is, however, also possible to position separate, i.e. additional elements on the test section or on the field which has a wave-guiding connection with the test section, in order to bring about a mode conversion of a volume sound wave into a Rayleigh wave or vice versa. For example, structures can be used which are stuck on, printed on, sintered on or dampened on the test section periodically with a division of around 1 of the wavelength of the Rayleigh wave.

Through structural measures on the mode converter, the preferred propagation direction of the Rayleigh wave, which originates in the contact of a volume sound wave with the mode converter, can be influenced. If required, a guided or symmetrical mode conversion can be achieved. If a Rayleigh wave reaches the sphere of influence of one of the above-described mode converters, this Rayleigh wave is, among other things, converted into a volume sound wave. Due to the attenuation properties of the vibration-guiding body in question and due to the conversion losses, as few mode converters as possible should lie within a path of the acoustic waves between sender and receiver.

In the event that a one-component sender-receiver unit should be provided for the purpose of generating and receiving volume sound waves by means of a simple oscillating crystal or shear vibrator, the use of only one mode converter is advantageous. It converts the volume sound wave running to the test section into a Rayleigh wave and the Rayleigh wave running back from a reflector into a volume sound wave which can be detected by the receiver. Suitable reflectors are in particular slit-like indentations with almost perpendicular flanks in relation to the propagation direction of the Rayleigh wave, but other points of discontinuity with sufficiently good acoustic reflection behavior are also suitable.

However, should the sender and the receiver (for the purpose of generating/receiving volume sound waves) be positioned far apart, the use of two mode converters which flank the test section at its ends will normally be necessary.

It is also possible to combine senders and receivers for different modes of the acoustic waves, and thus to use a sender for volume sound waves and a receiver for Rayleigh waves (or vice versa). Accordingly, a mode converter would have to be provided between the test section and the receiver/between the sender and the test section.

For the purpose of determining the physical characteristic or physical property to be measured, exclusively changes of at least one parameter of the Rayleigh wave are used, whereby a basis is preferably the dissipative energy loss of the Rayleigh wave in the test section.

The device provided for implementing the method uses an acoustic transfer system with at least one test section formed from a solid surface, whereby this test section can be brought at least partly into contact with the medium to be measured. The test section is suitable for forwarding Rayleigh waves (RW) at least on a length which corresponds to 1/8, preferably more than 2l of the generated Rayleigh wave (RW). According to the invention, at least one mode converter is in an operational connection with the test section or with a field connected to the test section, which a) converts a volume sound wave running from the sender to the test section into a Rayleigh wave and/or b) converts a Rayleigh wave running back from the test section to the receiver into a volume sound wave.

It is also worth noting that between the sender/receiver and the measurement location a comparatively large distance can be bridged, as Rayleigh waves can with a comparatively low energy loss cover long stretches due to their low angle straggling. The good transferability of the Rayleigh waves from one carrier to another carrier by means of an incompressible coupling medium (e.g. a liquid) can also be advantageously used for bridging distances.

Embodiments of the invention are examined in greater detail below by reference to the drawings. The drawings show:

FIG. 1a Schematic representation of an acoustic transfer system with formed system boundaries and a wave-guiding section between sender and receiver which can be traversed by Rayleigh waves.

Figure 1B:
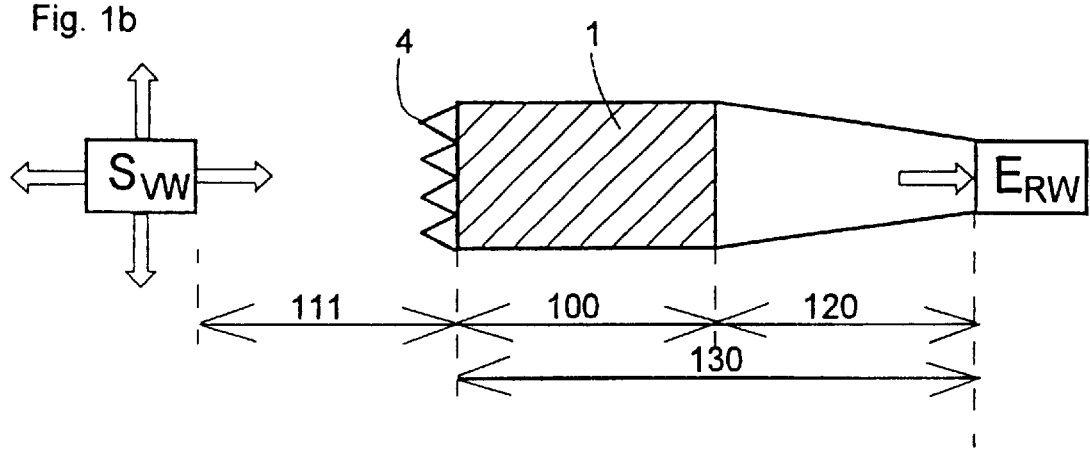

FIG. 1b Schematic representation of an acoustic transfer system with a sender for volume sound waves and a mode converter for converting volume sound waves into Rayleigh waves, whereby this mode converter is positioned at the beginning of the test section.

Figure 1C:
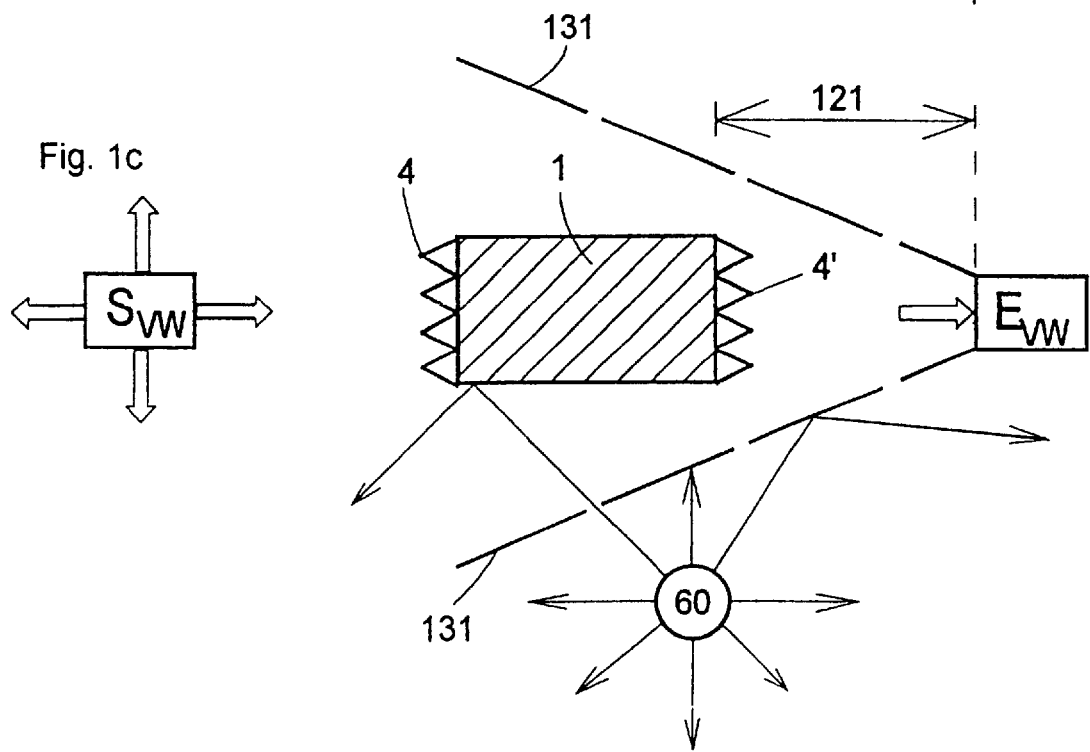

FIG. 1c Schematic representation of an acoustic transfer system with sender and receiver for volume sound waves and with mode converters for converting volume sound waves into Rayleigh waves and vice versa, whereby these mode converters are positioned respectively at the beginning and end of the test section.

Figure 1D:
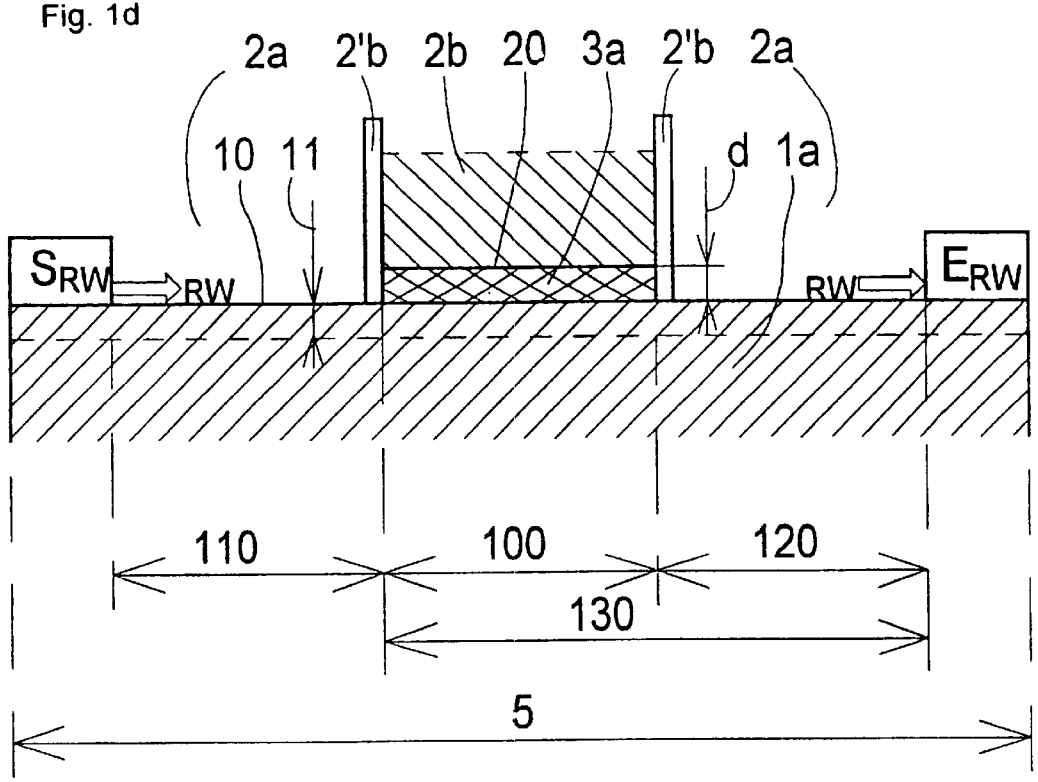

FIG. 1d Schematic representation of the acoustic transfer system for a measurement device with a thin liquid layer, the density of which is limited by a solid lying opposite the test section.

Figure 1E:
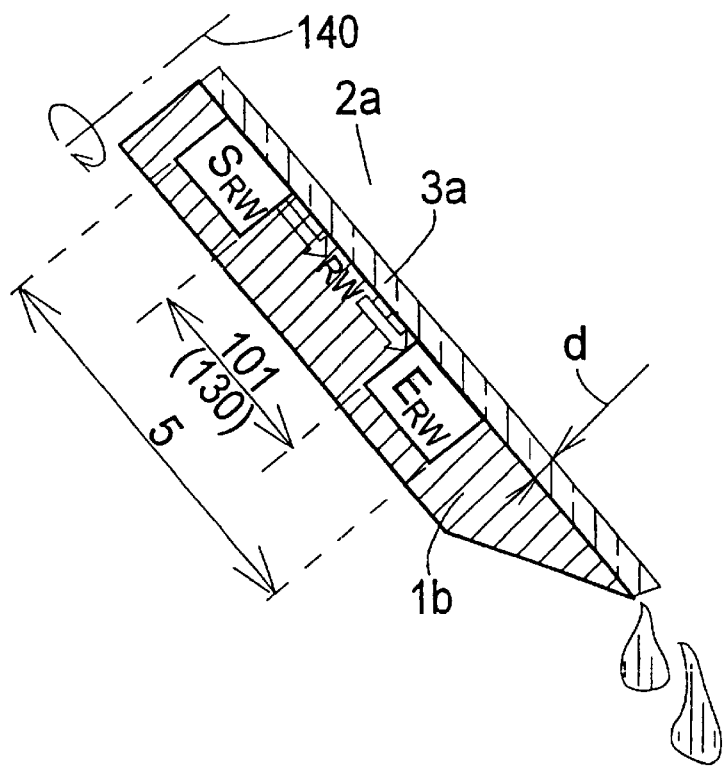

FIG. 1e Schematic representation of the acoustic transfer system for a measurement device with a thin liquid layer, the thickness of which is limited by gravity (tilted surface) or by centrifugal force.

FIG. 1f Schematic representation of the acoustic transfer system for a measurement device with a thin liquid layer, the thickness of which is limited by a separating column.

FIG. 1g Principle representation of a mixer device with contact rods, which also function as separating columns, in order to limit the layer thickness of the liquid for the periodic measurement process to the maximum admissible amount (according to the separating column principle of FIG. 1f).

FIG. 1h Transverse section of the mixer device of FIG. 1g.

Figure 1I:
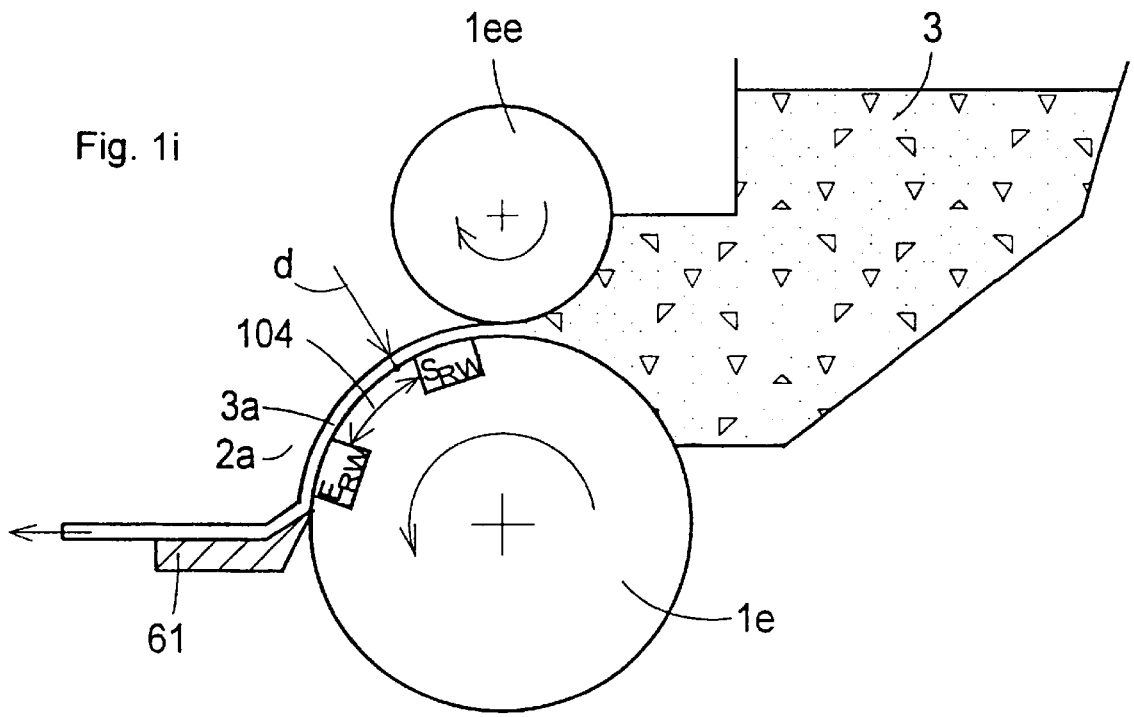

FIG. 1i Principle representation of a drum device with an acoustic transfer system rotating with the drum.

Figure 1J:
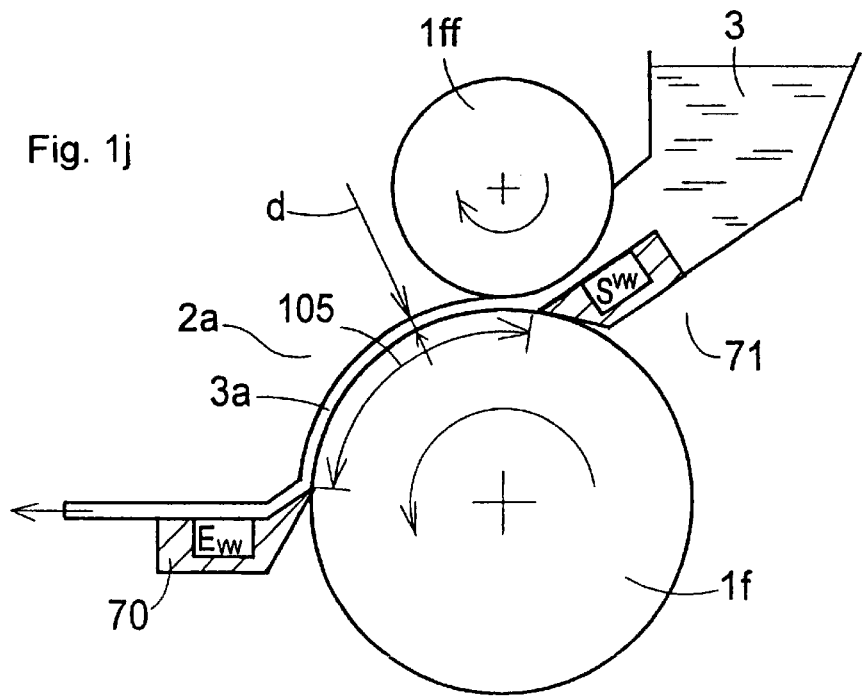

FIG. 1j Principle representation of a drum device with an acoustic transfer system, the test section of which is formed from the surface of the drum which is, however, virtually stationary.

Figure 1K:
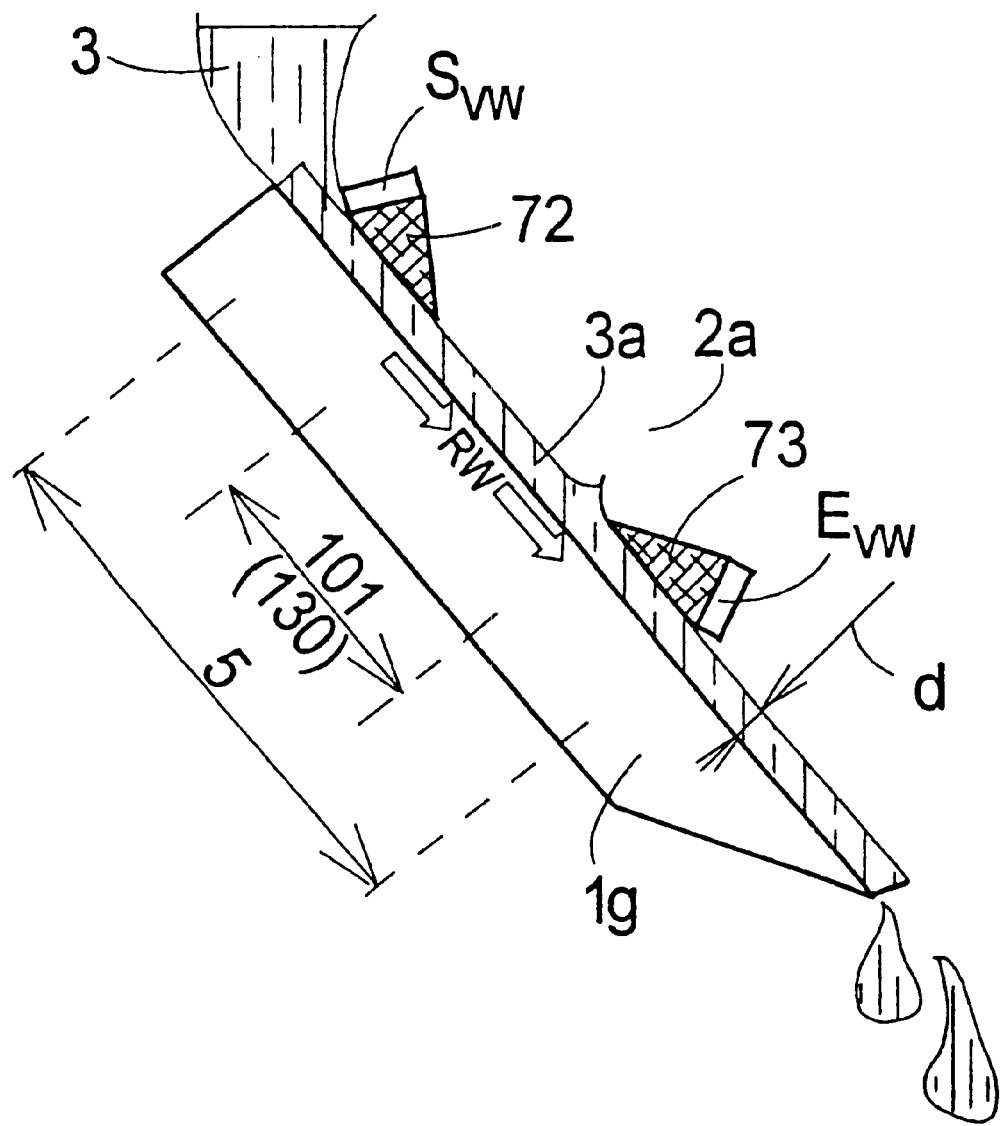

FIG. 1k Schematic representation of an acoustic transfer system with wedge-shaped coupling elements for producing Rayleigh waves by means of simple oscillating crystals which lie/float on a draining liquid layer.

Figure 1L:
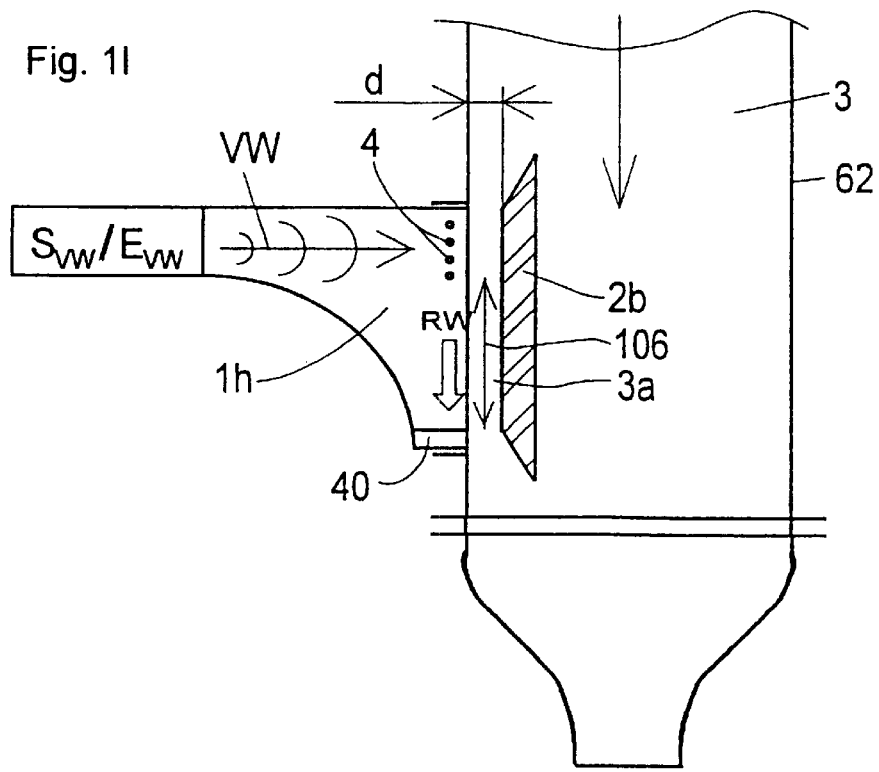

FIG. 1l Principle representation of a flow channel during sending mode with a measurement device in pulsed operation, whereby the test section thereof is limited by a mode converter and a reflector, and with a solid lying opposite the test section which limits the layer thickness of the liquid.

Figure 1M:
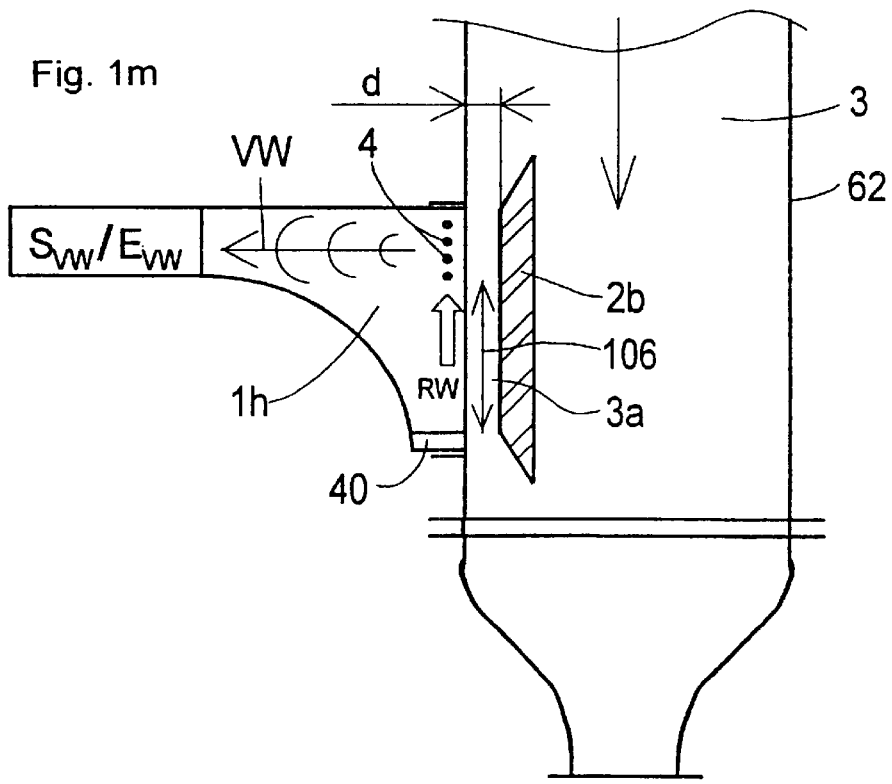

FIG. 1m As for FIG. 1l, but in receiving mode.

Figure 2A:
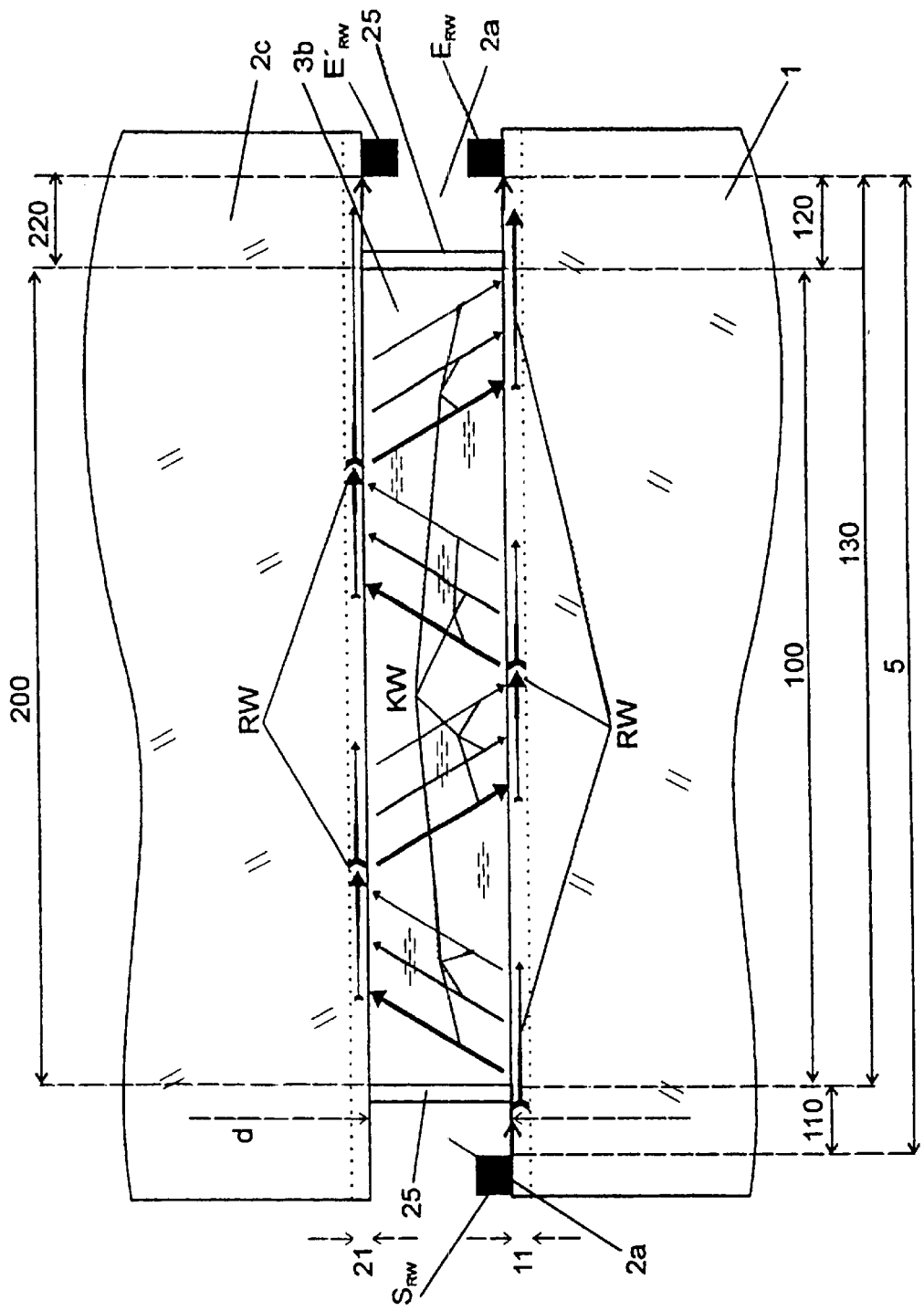

FIG. 2a Schematic representation of the acoustic transfer system for a measurement device with parallel opposite-lying solid border areas with equal Rayleigh wave speeds.

Figure 2B:
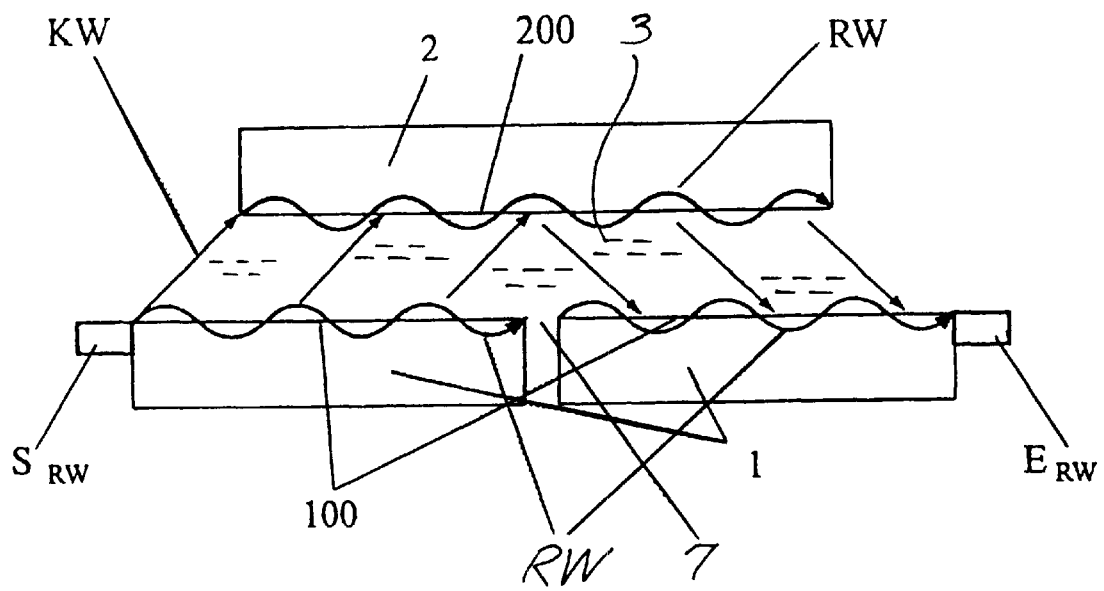

FIG. 2b Principle representation of a screw conveyor moving relative to its case and transporting the liquid. The sliding-past of the screw conveyor shoulder in relation to the test section allows in the short-term an acoustic coupling.

FIG. 2c Schematic representation of the acoustic transfer system for a measurement device with opposite-lying non-parallel solid boundary surfaces, the gradient of which is adapted to the different Rayleigh wave speeds.

FIG. 2d Principle representation of a slide bearing with an acoustic transfer system, the test section of which is formed from the seat of the roller bearing and the parallel opposite-lying boundary surface of the stored wave. The test section is positioned lengthwise to the wave axis.

Figure 2E:
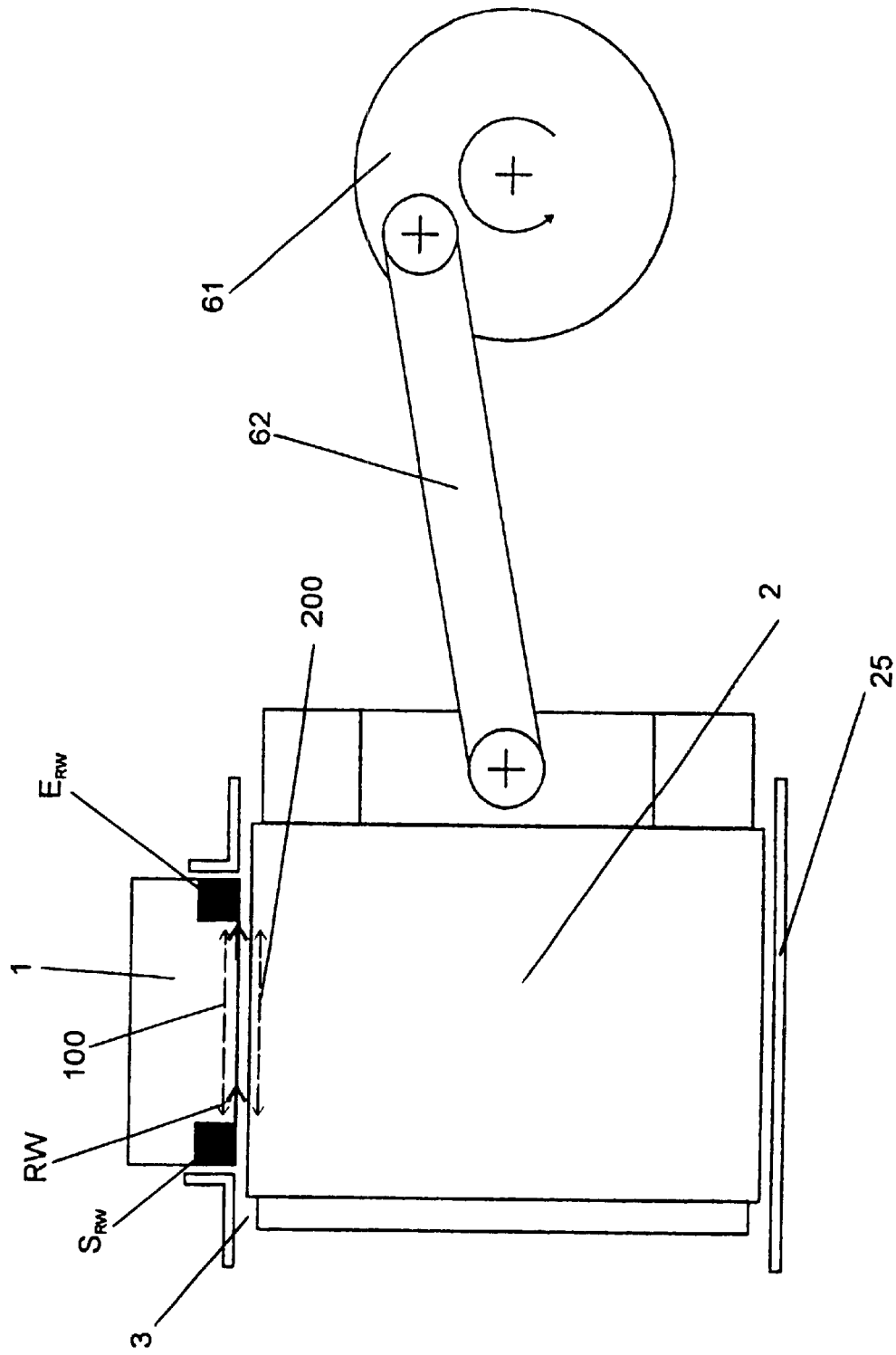

FIG. 2e Principle representation of a piston sliding in a cylinder with an acoustic transfer system, the test section of which is formed from a part of the cylinder wall and the opposite-lying parallel boundary surface area of the piston which slides by.

FIG. 2f Schematic representation of the acoustic transfer system for a measurement device with a solid boundary surface lying opposite the first solid boundary surface with a low Rayleigh wave speed which allows the coupling of volume sound waves and is connected to receivers for volume sound waves.

Figure 2G:
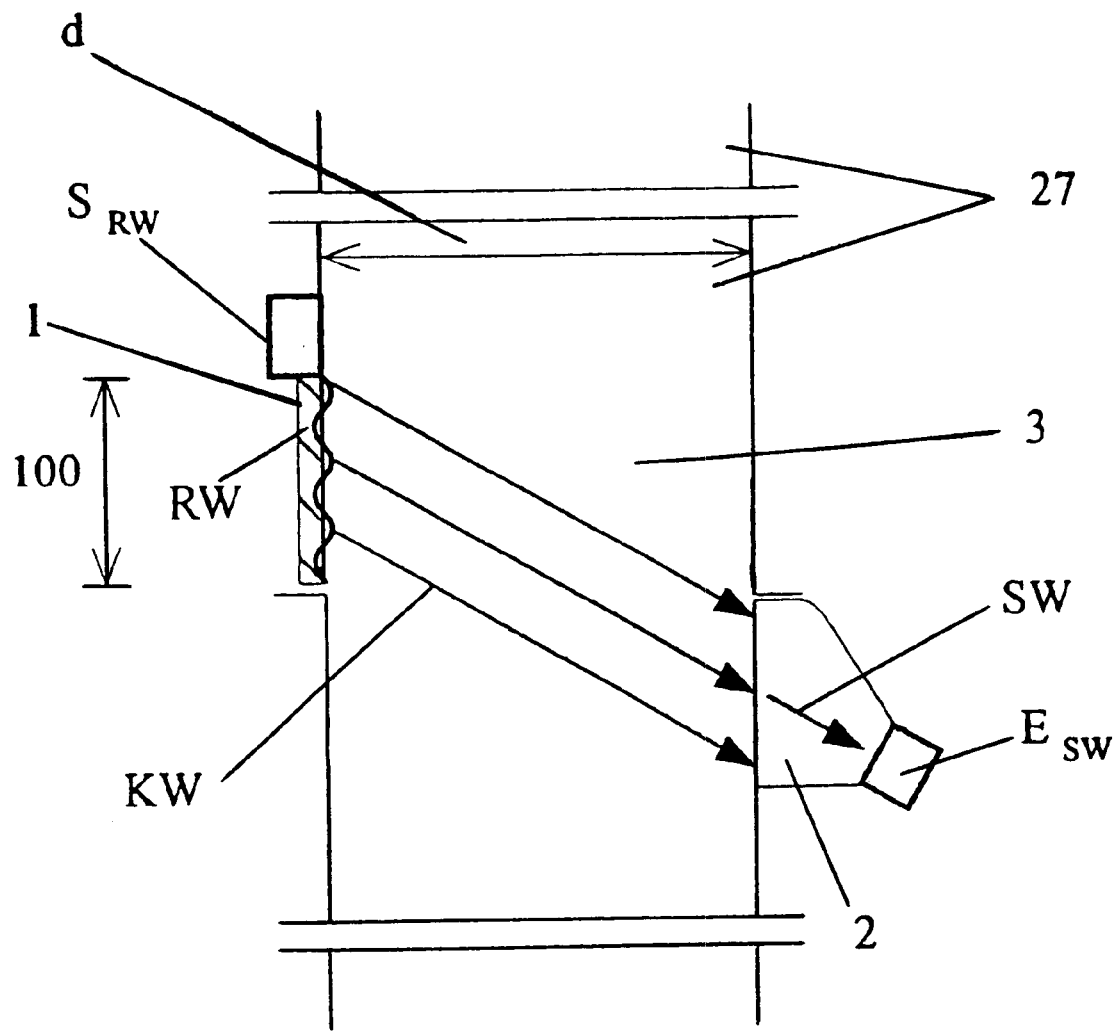

FIG. 2g Principle representation of a pipe segment with an acoustic transfer system which generates Rayleigh waves on the inner side of a pipe wall carrying the test section and the compression waves formed in the liquid filling the pipe are converted to volume sound waves on the opposite-lying pipe wall in a neighboring solid.

Figure 2H:
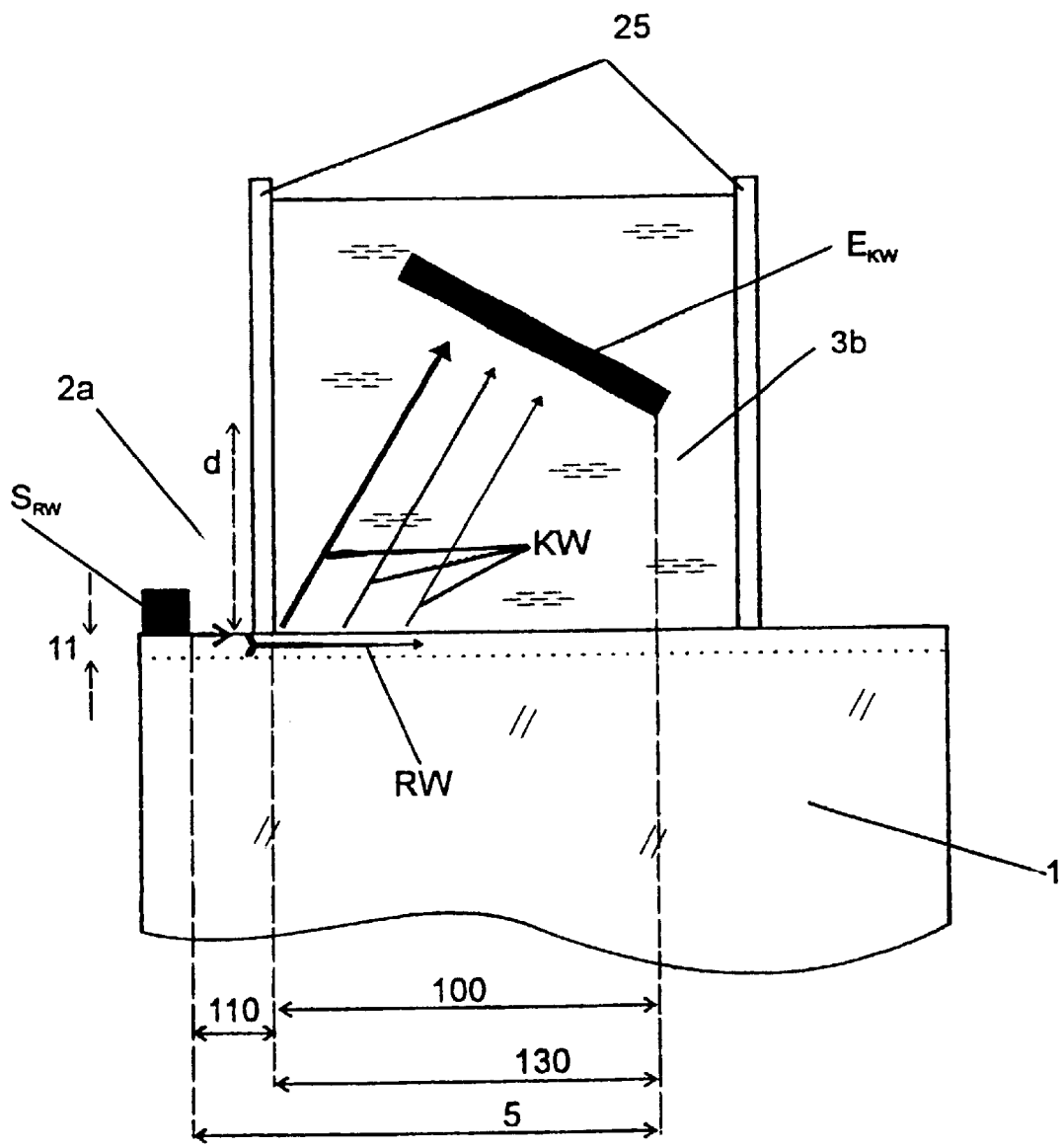

FIG. 2h Schematic representation of the acoustic transfer system for a measurement device with a solid boundary surface lying opposite the first solid boundary surface which is formed from a receiver for the compression waves propagating in the liquid.

FIG. 2i Principle representation of a pipe segment with an acoustic transfer system which generates Rayleigh waves on the inner side of a pipe wall which represents the test section and which leads the compression waves forming in the liquid filling the pipe directly into a receiver for compression waves.

Figure 3A:
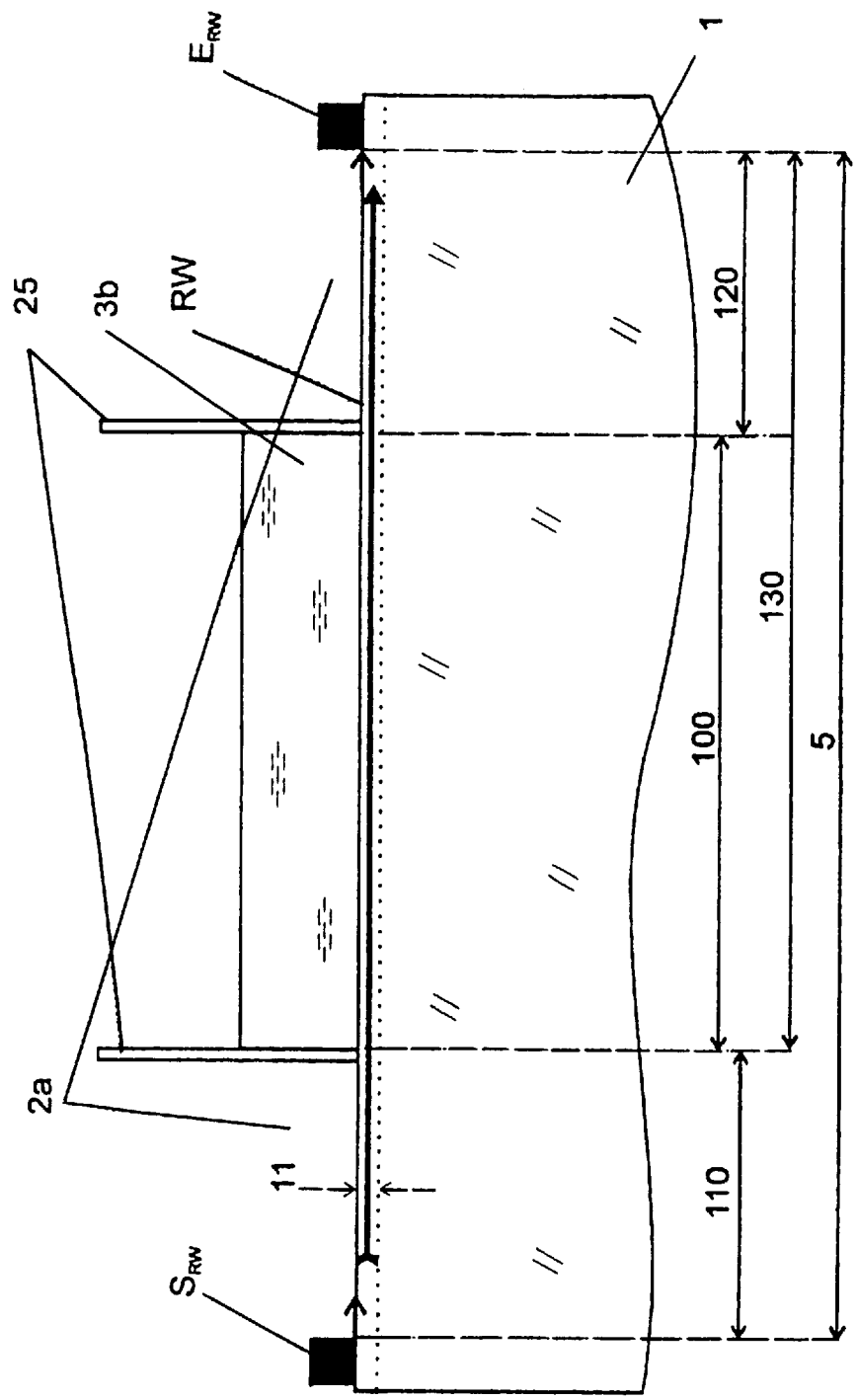

FIG. 3a Schematic representation of the acoustic transfer system for a measurement device with a substrate material, the sound speed of which for Rayleigh waves is lower than the sound speed of the contiguous liquid.

Figure 3B:
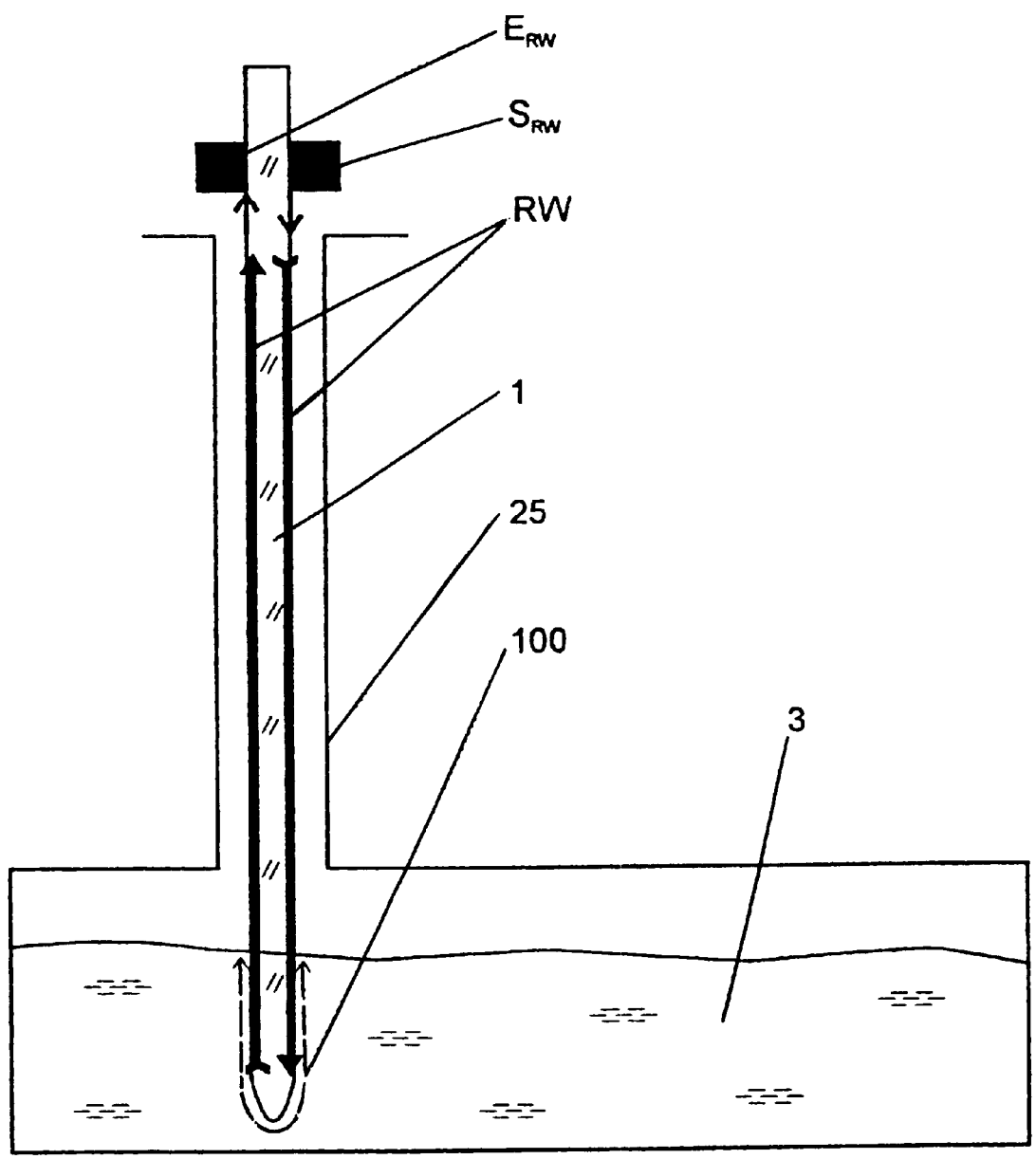

FIG. 3b Principle representation of a measurement device with great geographical separation between the location of the sender and the receiver and the location of the test section.

FIG. 3c Principle representation of a measurement device which allows measuring in an isolated receptacle containing the liquid, whereby all the components necessary for producing and receiving the Rayleigh wave are positioned outside the receptacle.

Figure 3D:
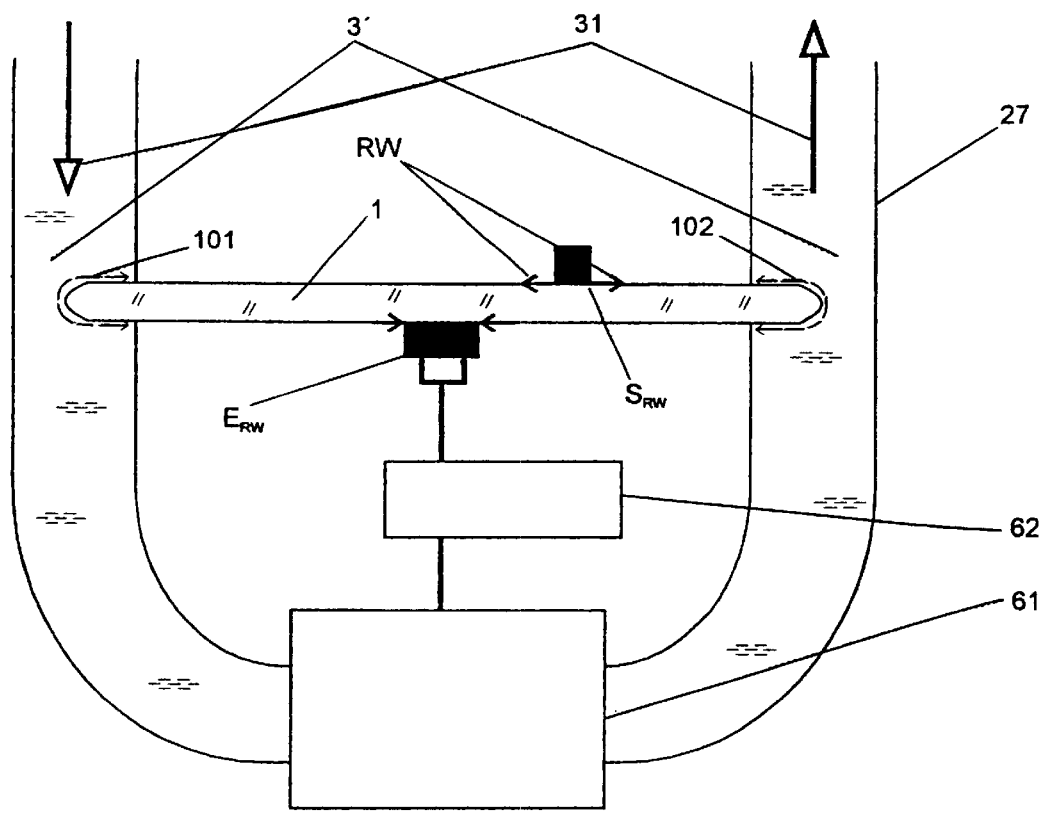

FIG. 3d Principle representation of a measurement device made from two test sections using a one-component solid guiding the Rayleigh waves for the purpose of comparing the properties of a liquid flowing through a reactor. The principle of FIG. 3c is thereby used.

Figure 3E:
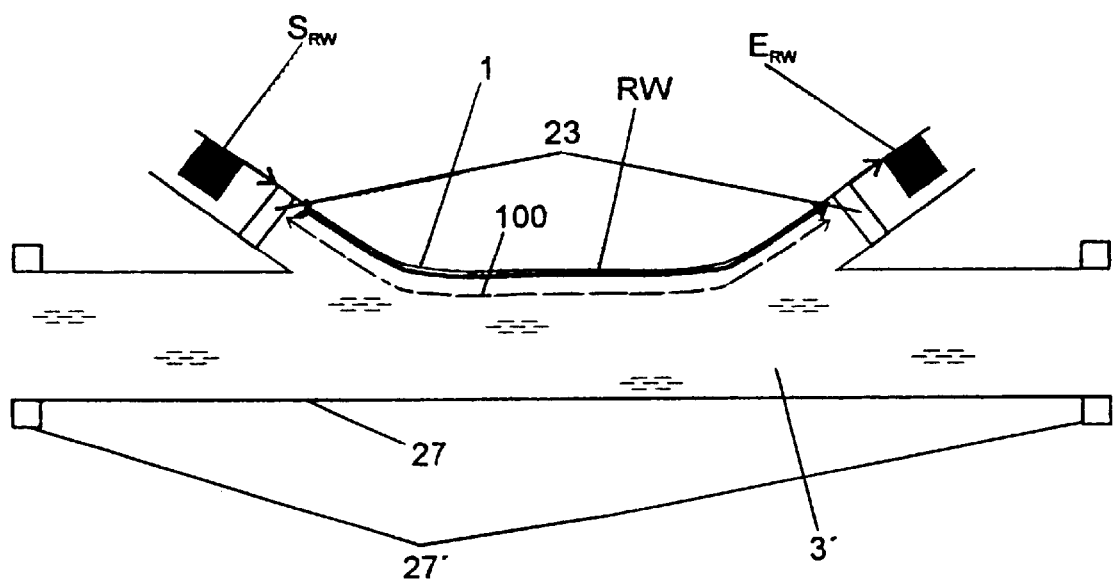

FIG. 3e Principle representation of a pipe segment with a measurement device which does not reduce the pipe cross-section.

Figure 3F:
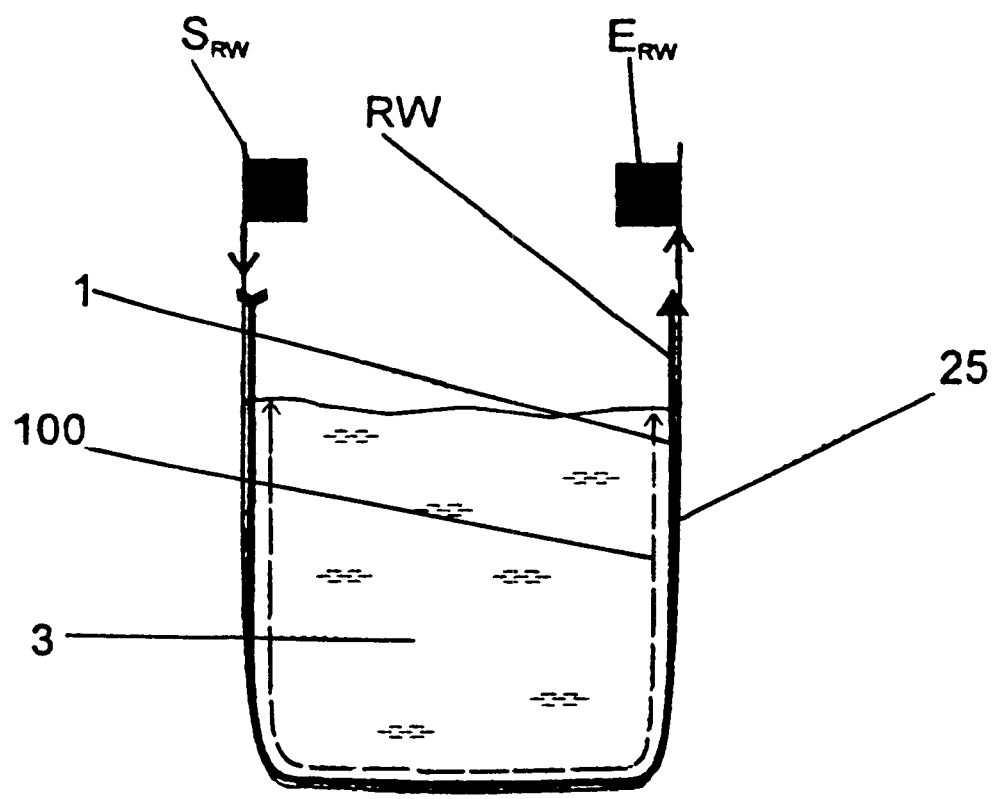

FIG. 3f Principle representation of a cross-section through a receptacle with a measurement device which uses the receptacle wall as the solid guiding the Rayleigh waves.

Figure 4A:
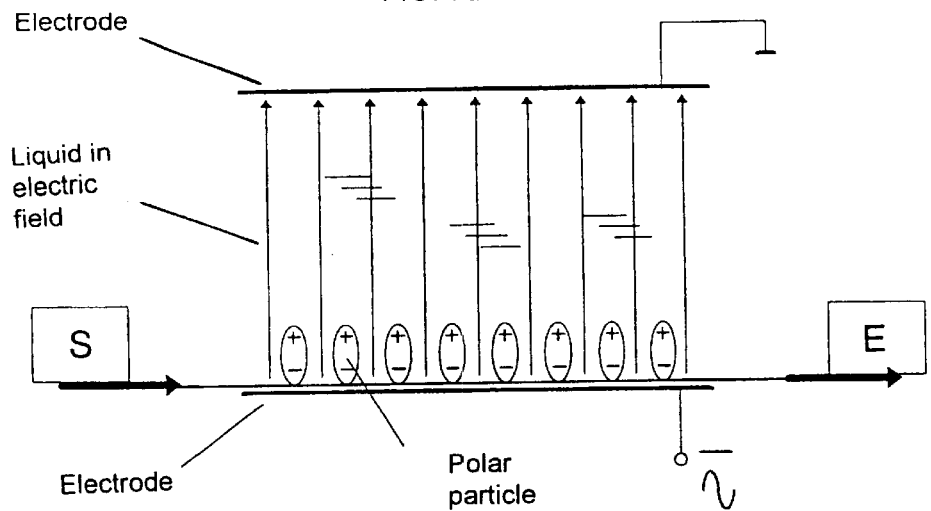

FIG. 4a Principle representation of a test section in the electric field.

Figure 4B:
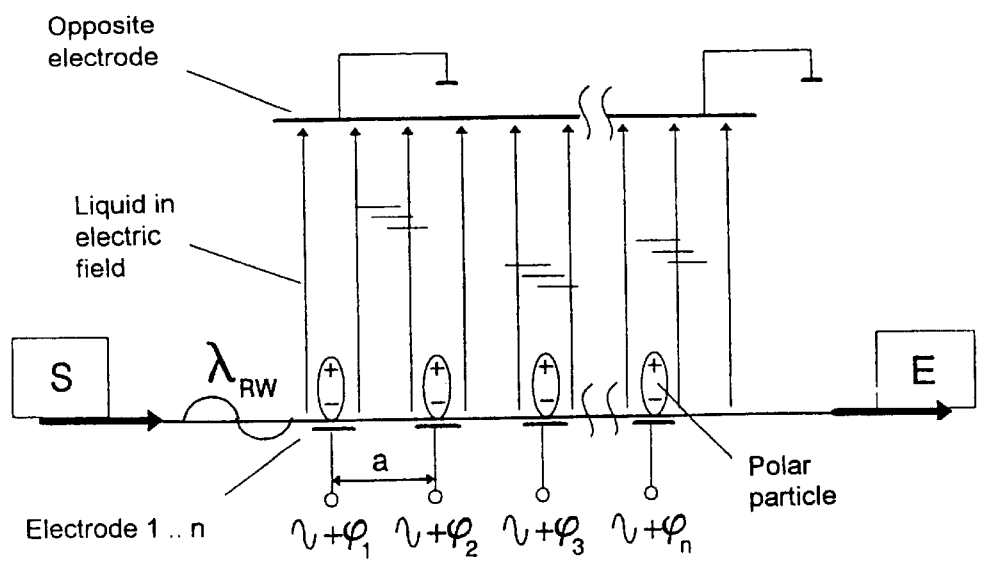

FIG. 4b Principle representation of a test section in the electric field with several allocated electrodes which can be controlled separately.

Figure 4C:
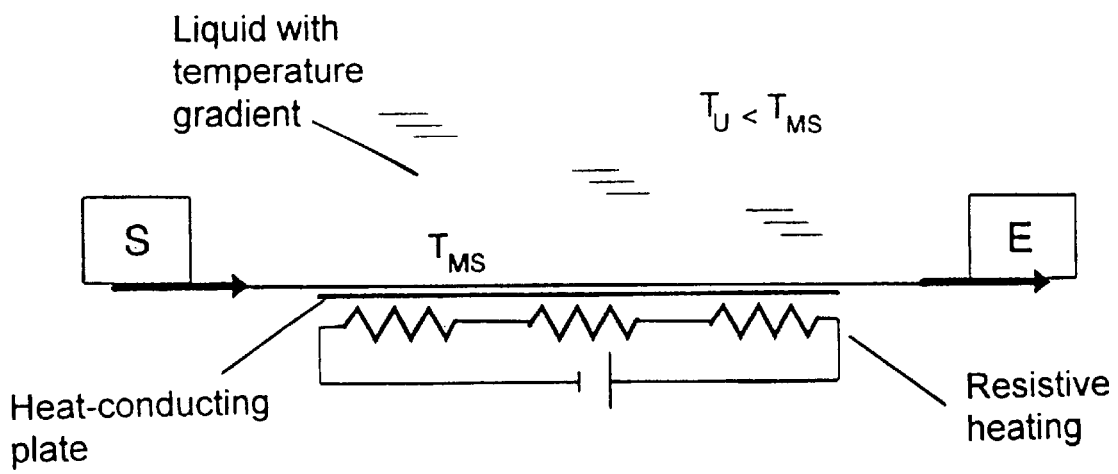

FIG. 4c Principle representation of a test section with electric resistive heating.

Figure 4D:
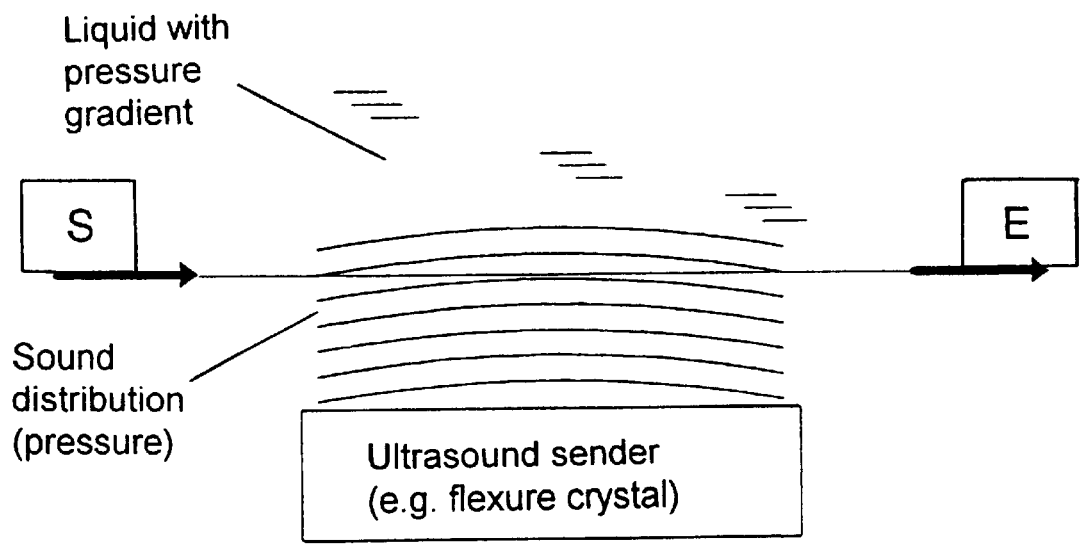

FIG. 4d Principle representation of a test section with an oscillating crystal for introducing mechanical energy.

Figure 4E:
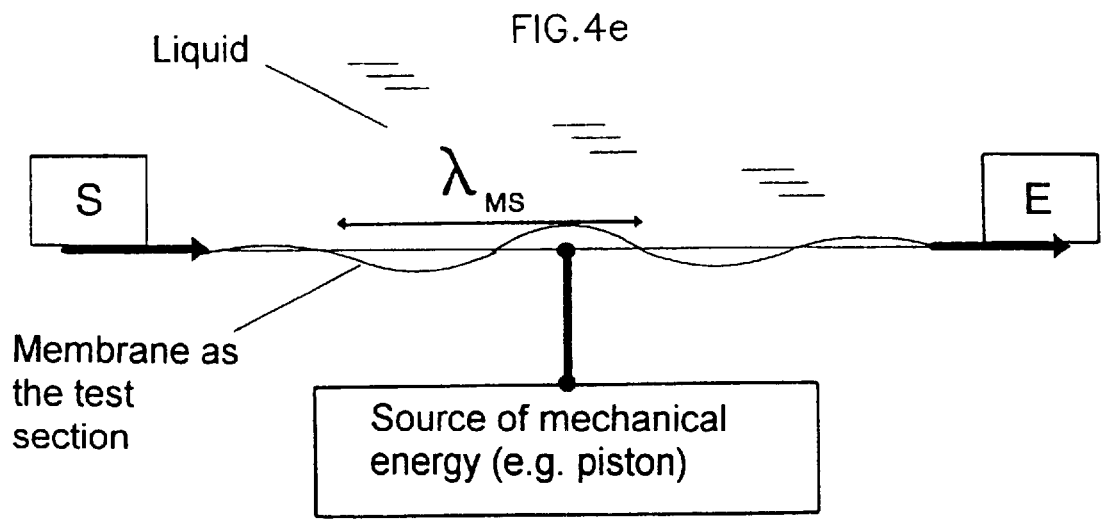

FIG. 4e Principle representation of a membrane-like test section with a connected mechanical element.

Figure 4F:
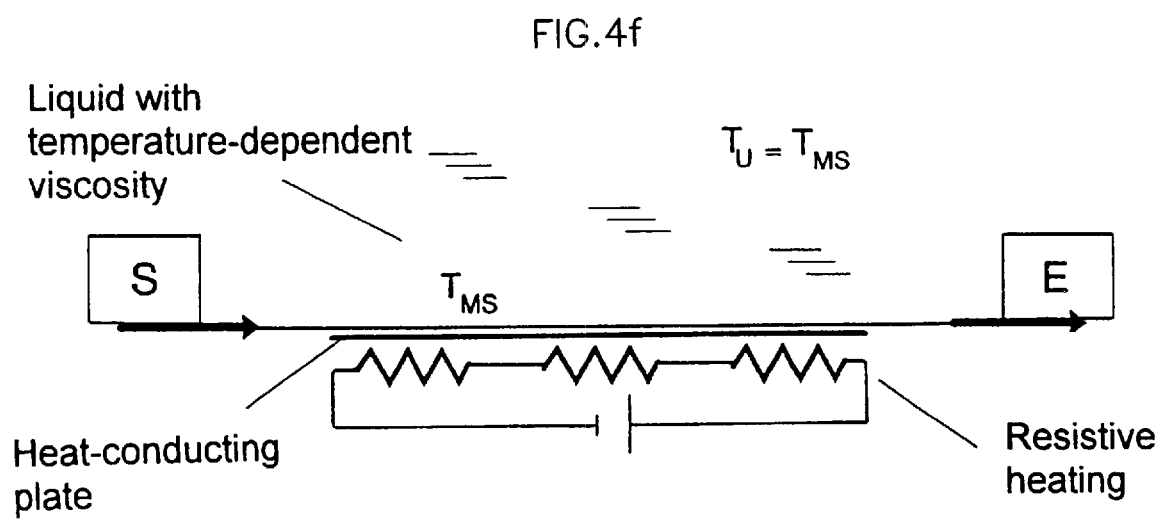

FIG. 4f Principle representation of a measurement device with temperature control via viscosity measurement.

Figure 4G:
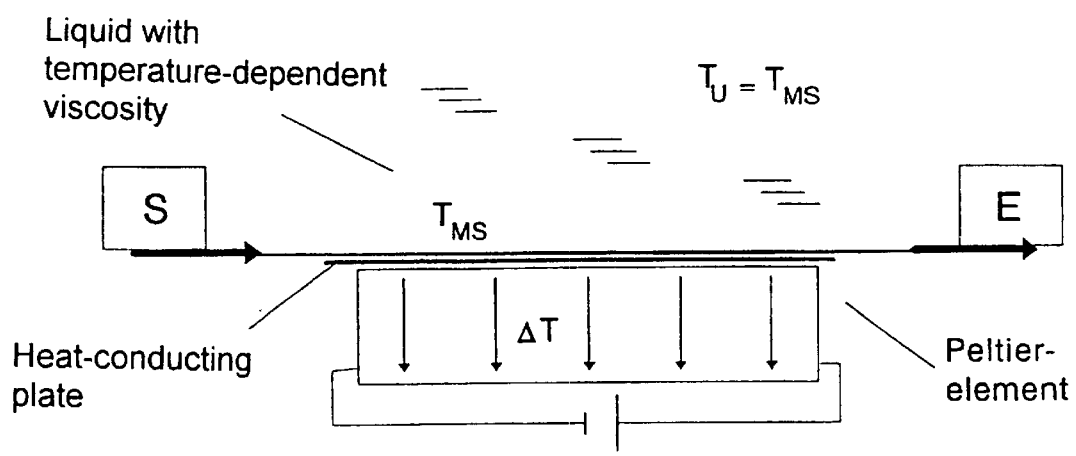

FIG. 4g Combination of a test section with a Peltier element.

Figure 4H:
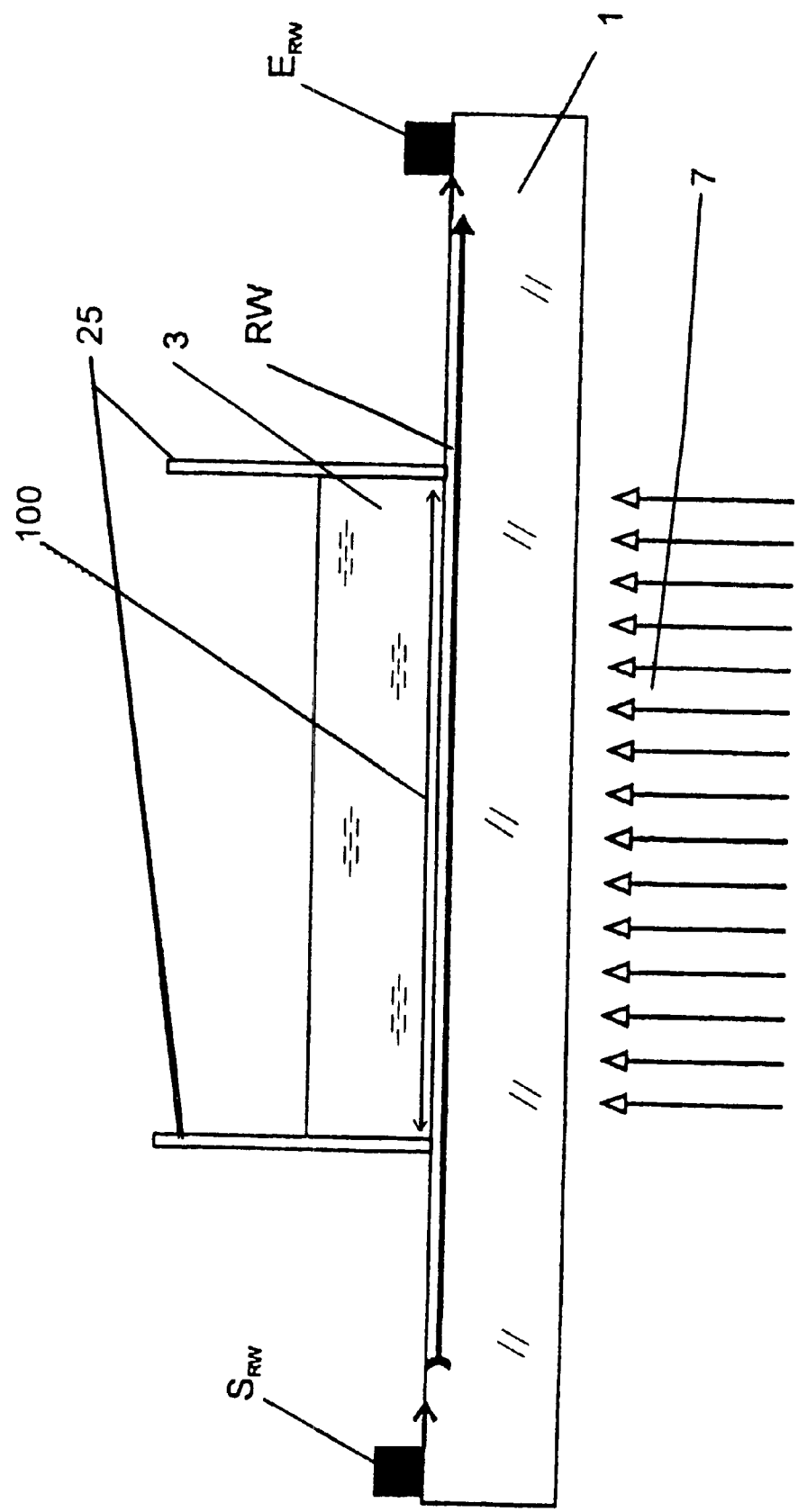

FIG. 4h Schematic representation of the acoustic transfer system for a measurement device on a transparent carrier material, whereby optical energy is additionally brought into the test section.

Figure 4I:
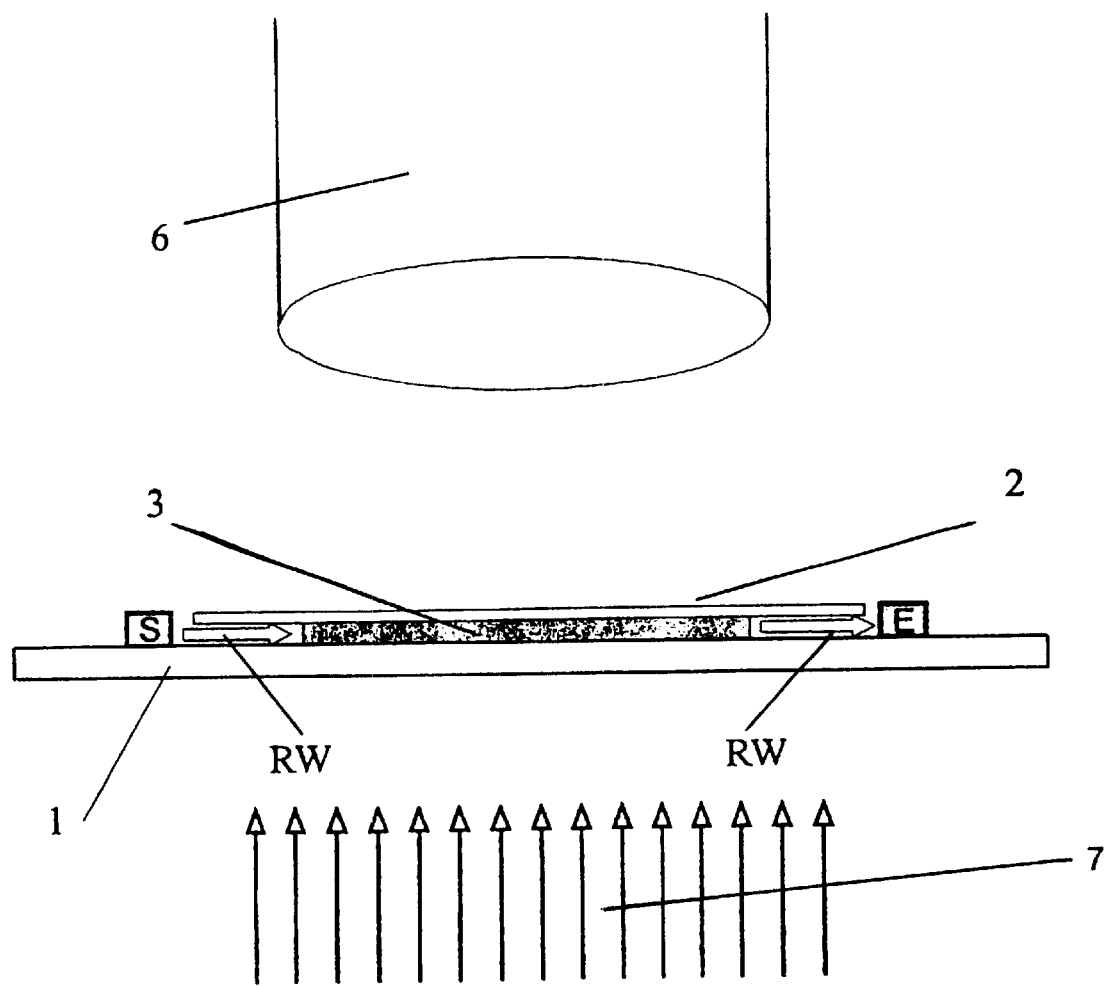

FIG. 4i Principle representation of a combination of acoustic measurement and optical observation device for simultaneous measurement and observation of the change in liquid properties.

Figure 5A:
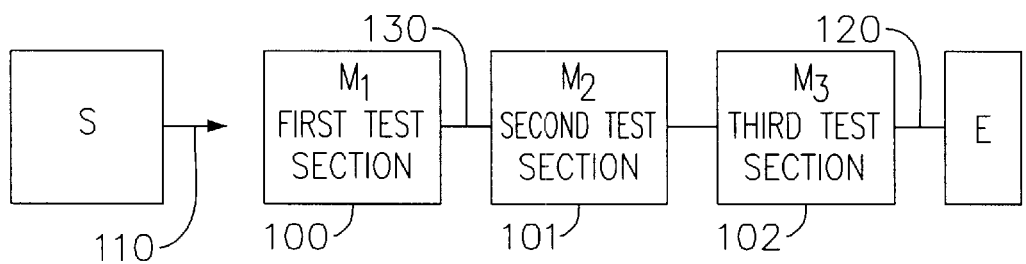

FIG. 5a Schematic representation of devices with several test sections positioned behind one another.

Figure 5B:
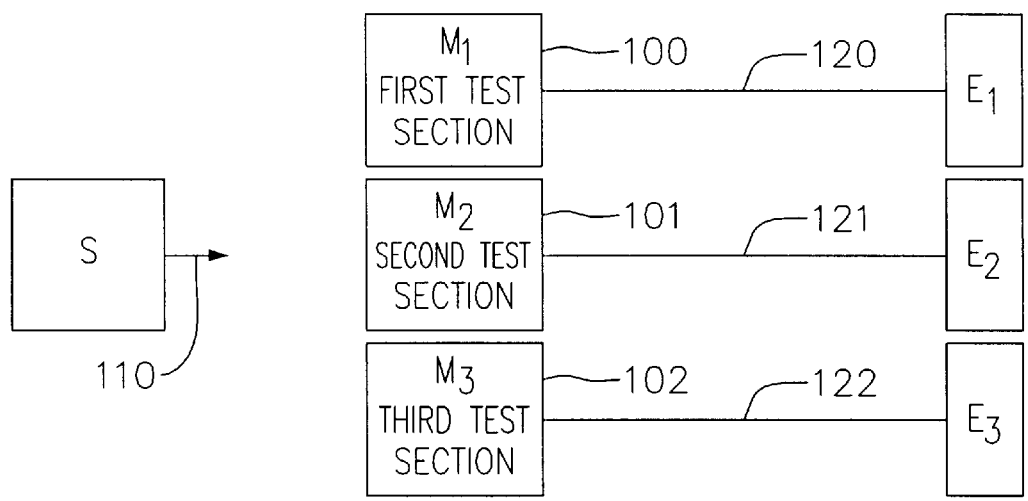

FIG. 5b Schematic representation of devices with several parallel positioned test sections with several receivers.

Figure 5C:
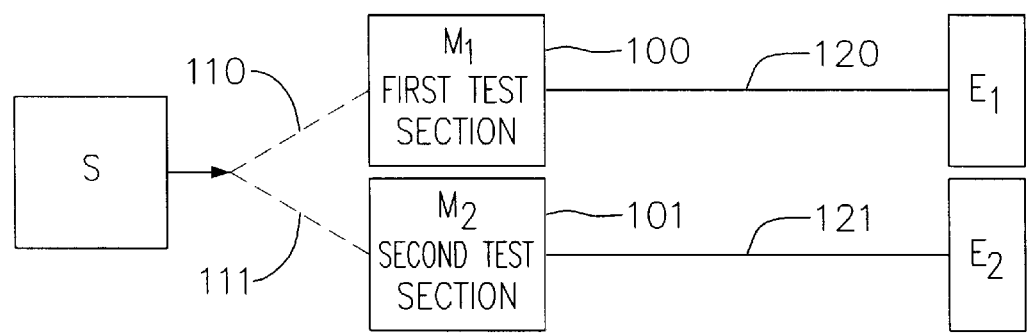

FIG. 5c Schematic representation of devices with several parallel positioned test sections with a single receiver.

Figure 5D:
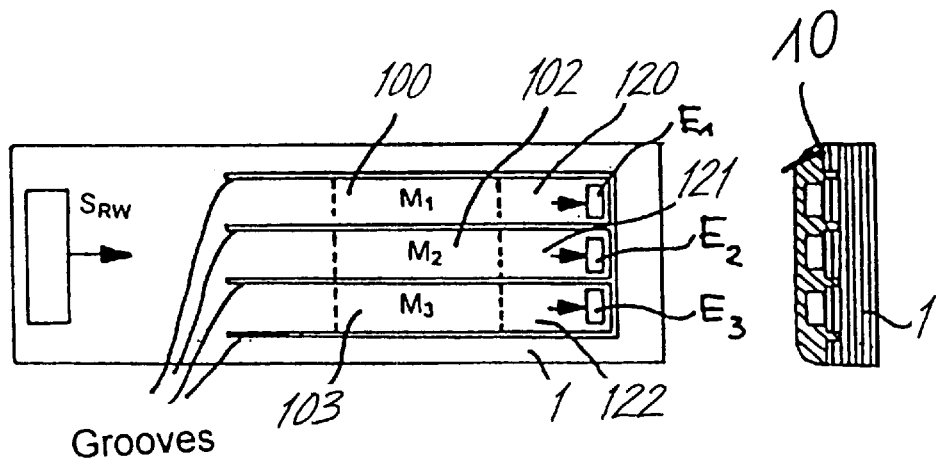

FIG. 5d Schematic representation of devices with several embodiment of a configuration of test sections according to FIG. 5b.

Figure 5E:
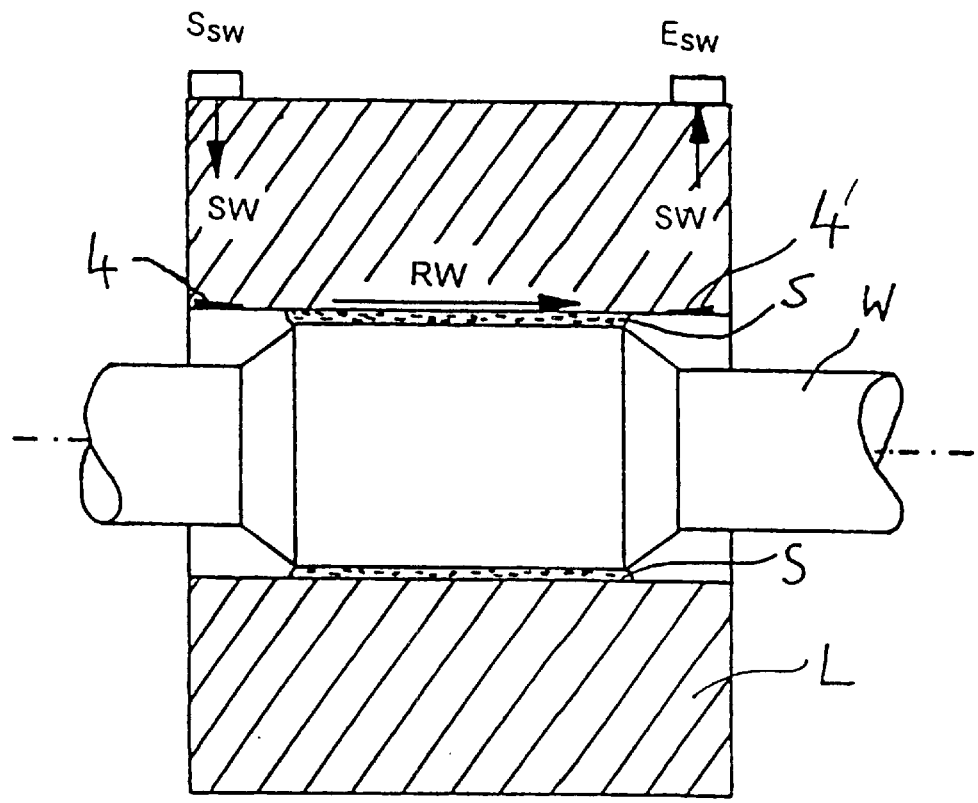

FIG. 5e Schematic representation of devices with several embodiment of a configuration according to the invention for determining a physical parameter of a lubricating film in a slide bearing.

FIG. 5f Schematic representation of a configuration according to the invention with parallel positioned test sections using mode conversion in the wave guide.

FIG. 5g Embodiment of the configuration according to FIG. 5f.

Figures 5H, 5I, 5J:
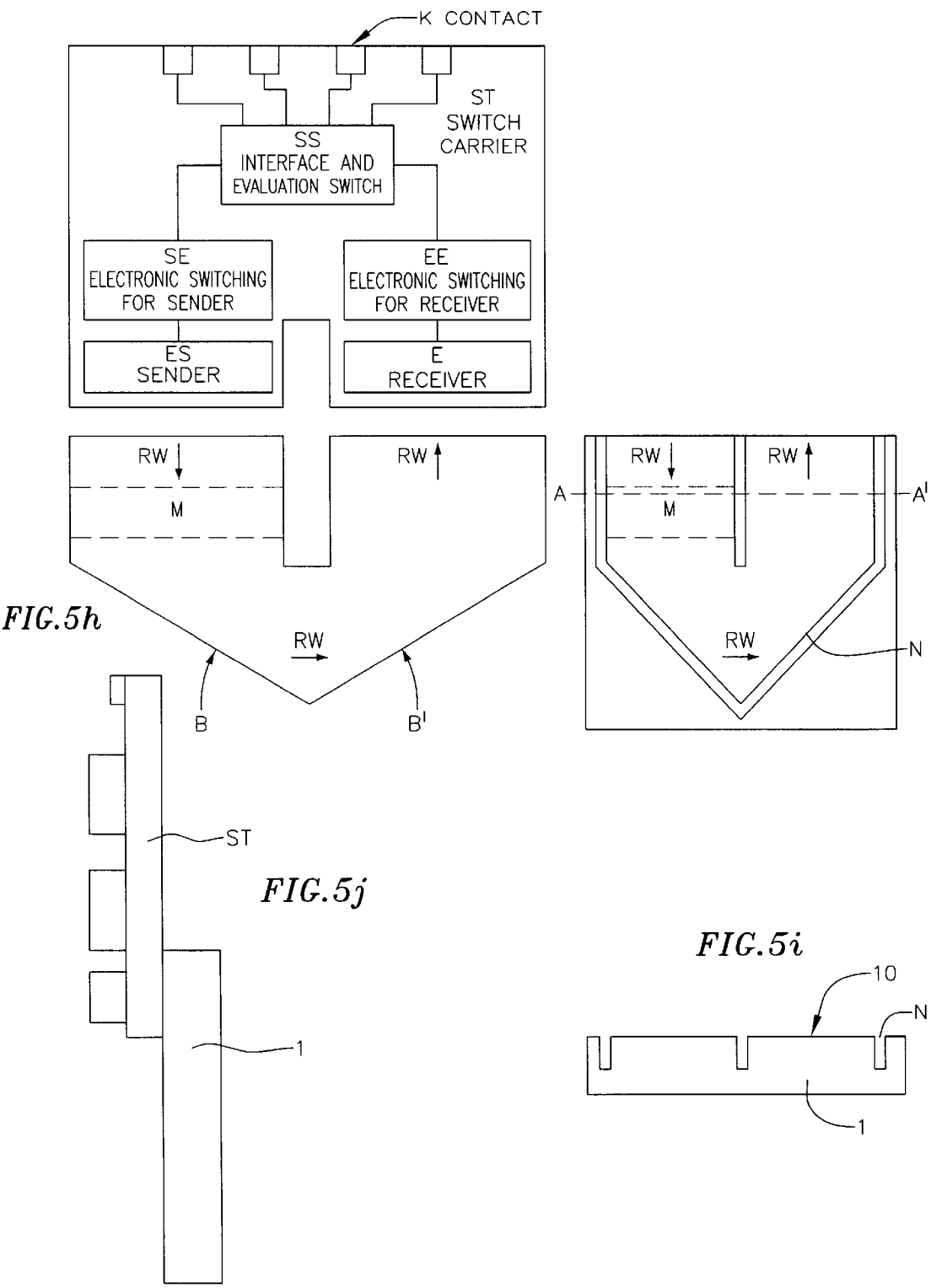

FIG. 5h Example of wave guides on which Rayleigh waves are reflected between sender and receiver, where reflection of the Rayleigh waves is on the outer edges of the wave guide.

FIG. 5i Example of wave guides on which Rayleigh waves are reflected between sender and receiver, reflection of Rayleigh waves is on grooves positioned in a solid.

FIG. 5j Example of wave guides on which Rayleigh waves are reflected between sender and receiver, with a schematic representation of an embodiment of a compact sender and receiver configuration.

Figure 6:
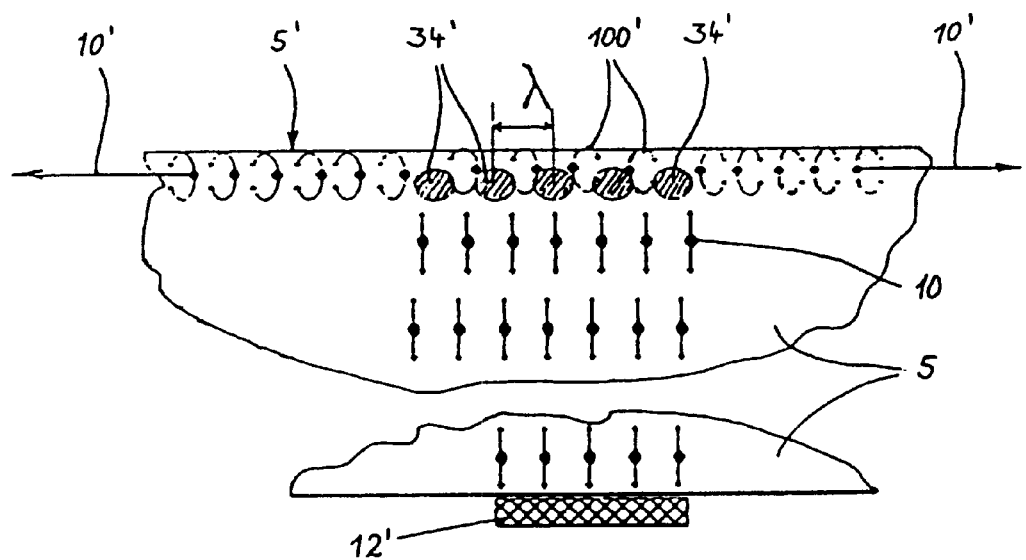

FIG. 6 Section of a solid with a periodic hole structure as a mode converter in the vicinity of the solid surface.

Figure 7:
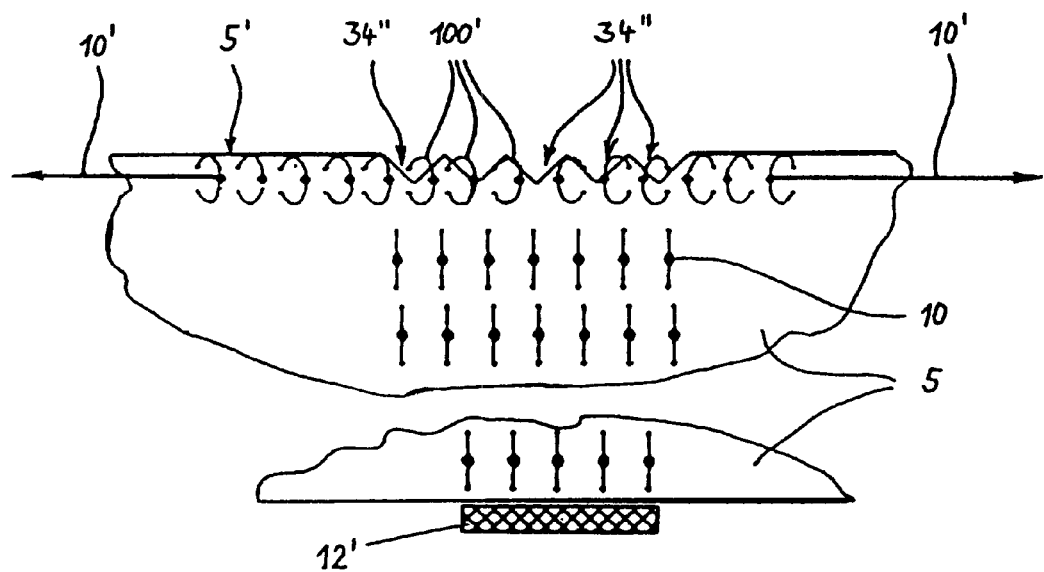

FIG. 7 Section of a solid with a periodic indentation structure as a mode converter in the vicinity of the solid surface.

Figure 8:
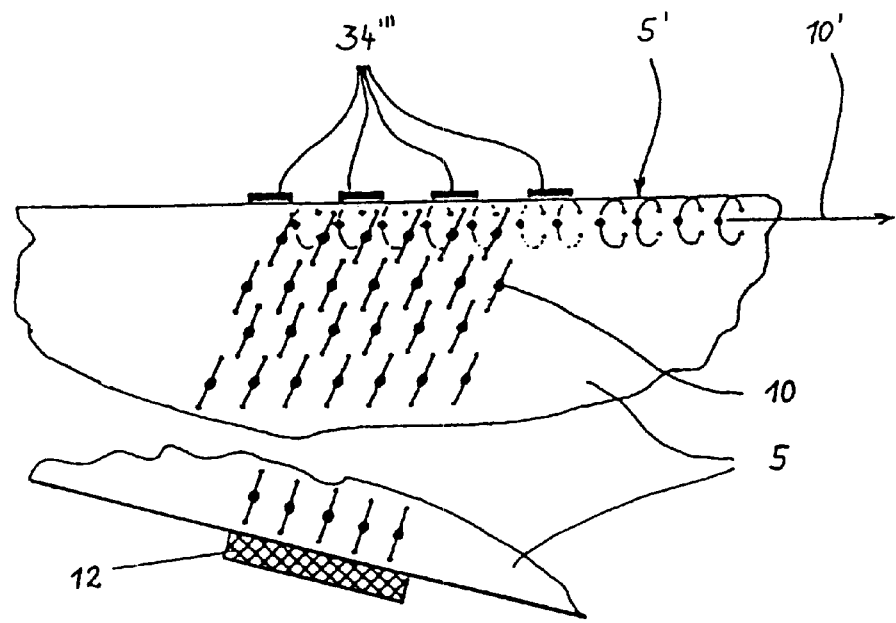

FIG. 8 Section of a solid with a periodic surface structure as a mode converter, formed from elements stuck on the solid surface.

Figure 9:
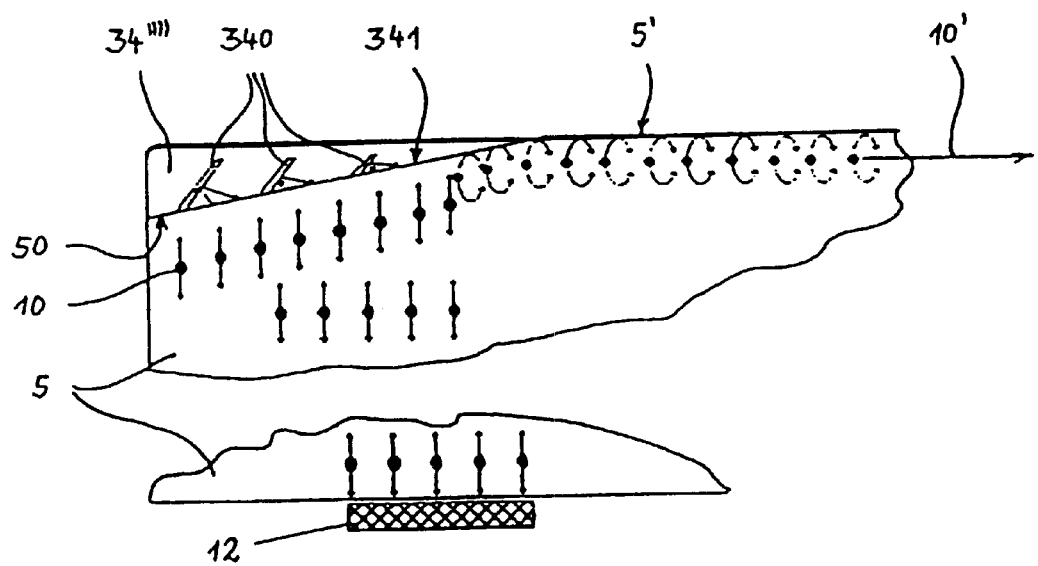

FIG. 9 Section of a solid with a periodic structure of reflection elements in a wedge positioned on the solid surface as a mode converter.

Figure 10:
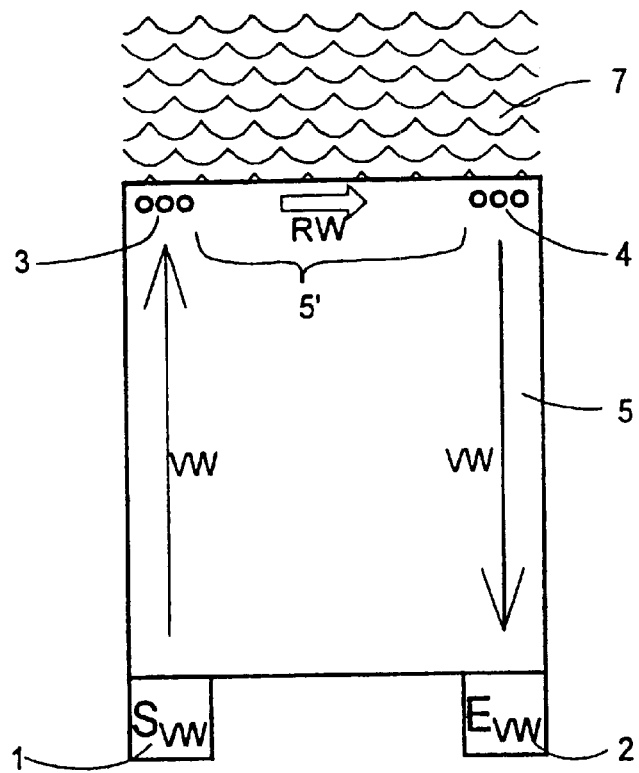

FIG. 10 Principle representation of a measurement installation with a test section which is limited by two mode converters.

Figure 11:
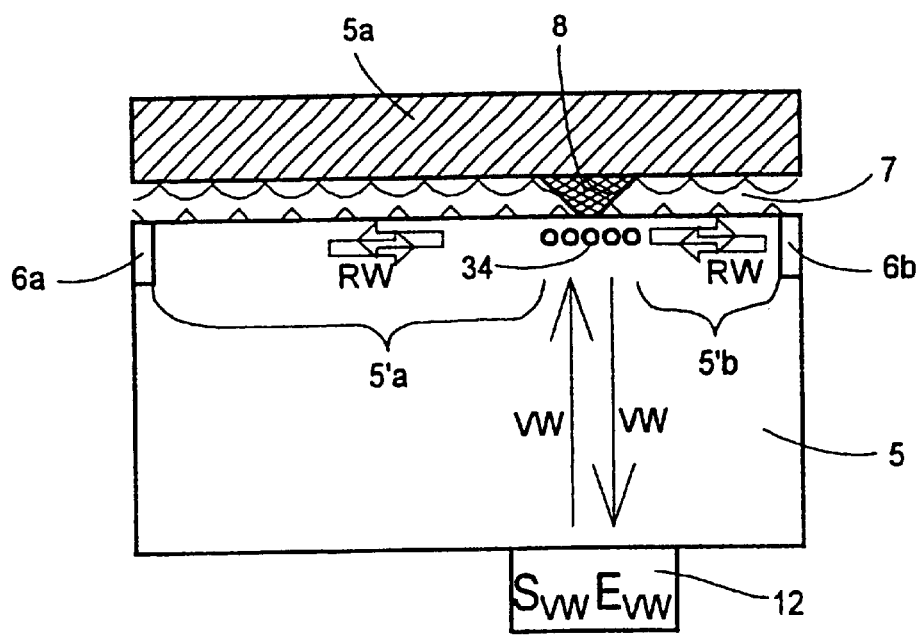

FIG. 11 Principle representation of a measurement installation with two test sections which extend right and left from a common mode converter to the allocated reflectors, and with a thin liquid layer with a thickness less than $l_{KW}/4$ of the compression wave.

Figure 12A:
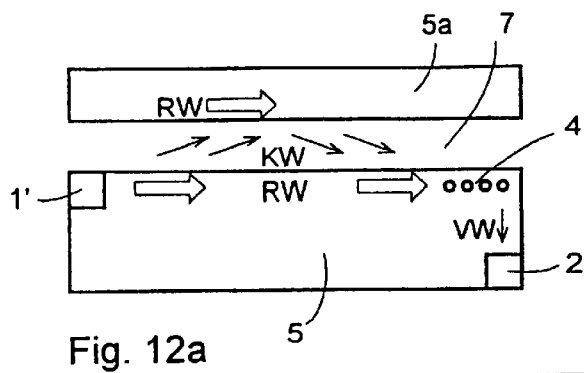

FIG. 12a Principle representation of a measurement installation with a solid lying opposite the test section, whereby the Rayleigh wave speed of the solid corresponds to the test section, with a Rayleigh wave sender and a volume sound wave receiver in the solid of the test section.

Figure 12B:
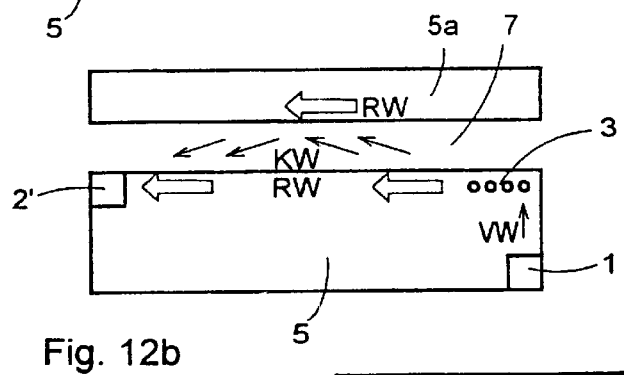

FIG. 12b As for FIG. 12a, but with a volume sound wave sender and a Rayleigh wave receiver in the solid of the test section.

Figure 12C:
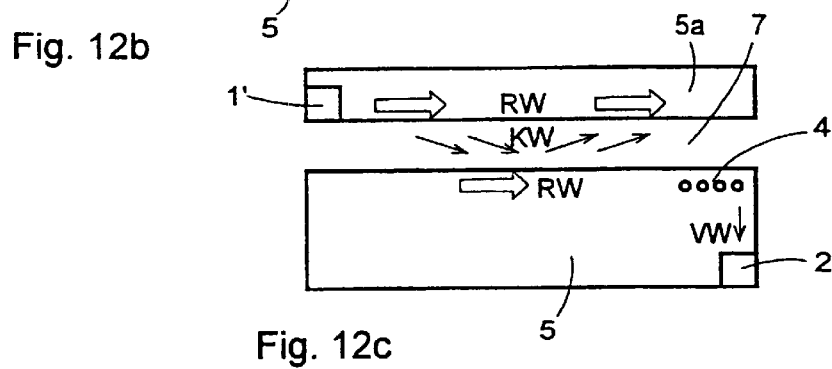

FIG. 12c As for FIG. 12a, but with a Rayleigh wave sender in the opposite-lying solid and a volume sound wave receiver in the solid of the test section.

Figure 13:
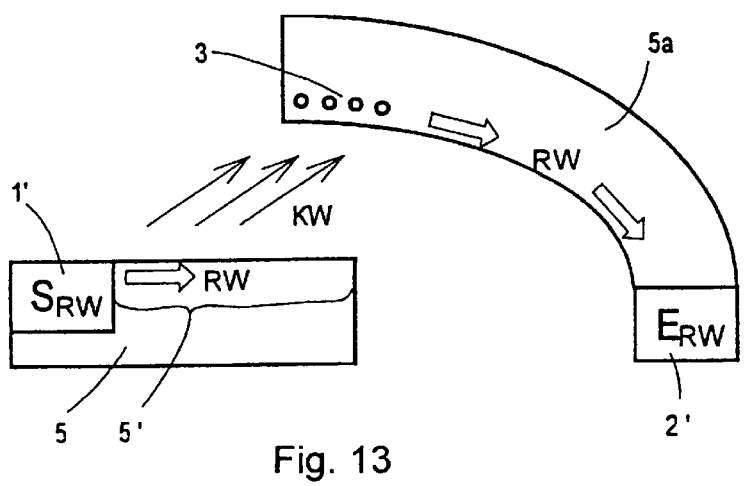

FIG. 13 Measurement installation with a solid curved in relation to the plane of the test section or positioned at a gradient, whereby the solid carries a Rayleigh wave receiver.

Figure 14A:
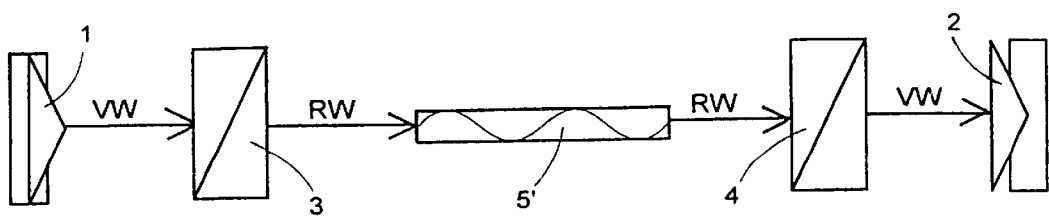

FIG. 14a Block wiring diagram of the propagation and conversion of a volume sound wave between the sender and the receiver, using a respective mode converter at the edges of the test section.

Figure 14B:
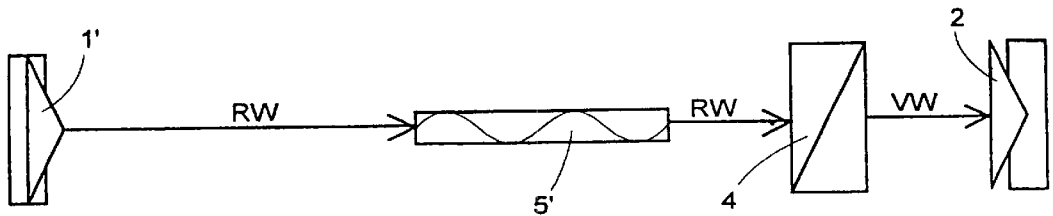
Figure 14C:
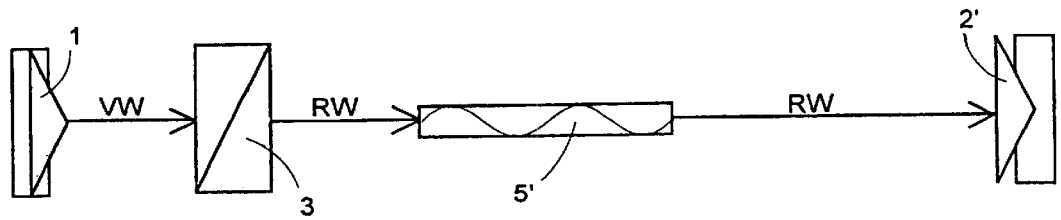
Figure 14D:
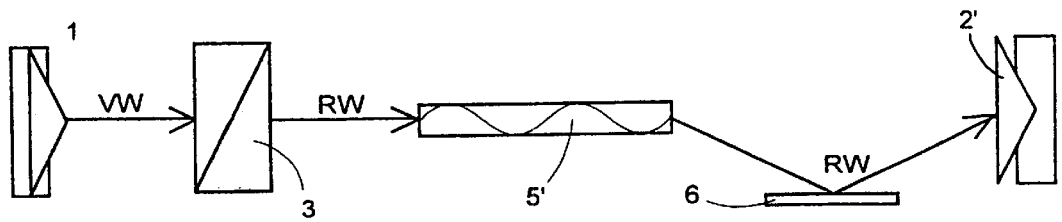

FIG. 14b Block wiring diagram of the propagation and conversion of a volume sound wave between the sender and the receiver, using a mode converter between the test section and the receiver FIG. 14c Block wiring diagram of the propagation and conversion of a volume sound wave between the sender and the receiver, using a mode converter between the sender and the test section FIG. 14d As for FIG. 14c, but additionally with a reflector in the path of the wave propagation between the test section and the receiver.

Figure 14E:
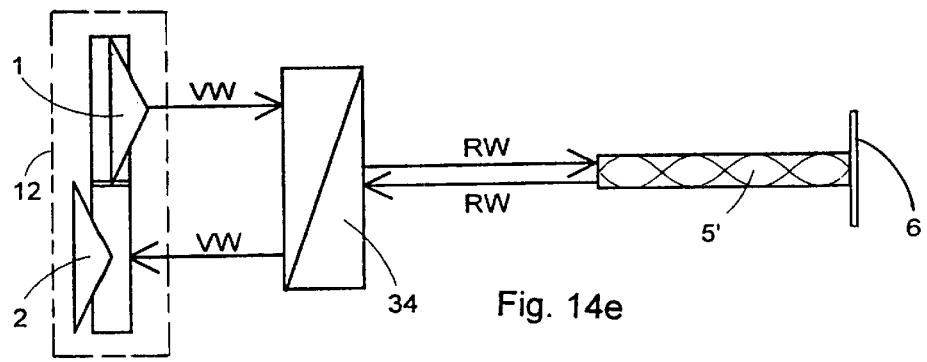

FIG. 14e Block wiring diagram of the propagation and conversion of a volume sound wave between the sender and the receiver with a one-component sender-receiver unit and a mode converter running in two directions from the wave.

DETAILED DESCRIPTION

FIGS. 1a to 1c show according to the invention, the wave-guiding property of the acoustic transfer system. These examples are only representative of the multitude of possible combinations/configuration of the elements (sender, receiver, test section and, if appropriate, feed section, removal section, mode converter, protection) belonging to the acoustic transfer section.

The schematic representation of FIG. 1a shows a test section 100, which is connected on one side to a feed section 110 to a sender $S_{RW}$ for Rayleigh waves and on the other side is connected via a removal section 120 to a receiver $E_{RW}$. The test section 100 is thus geographically or physically separated from the sender $S_{RW}$ and the receiver $E_{RW}$. If the material chosen for the feed section 110 and removal section 120 is different from the material carrying the test section 100, there is also an uncoupling on the material side. This has the advantage that the test section 100 can be optimally adapted to suit the concrete conditions of the respective application. One does not have to use special materials suited for the generation of Rayleigh waves. According to the embodiment of the invention described, so far as possible exclusively Rayleigh waves are generated by the sender $S_{RW}$ on the neighboring feed section 110 and made available at (the beginning of) the test section 100. The test section 100 is connected to a liquid which is to be measured (not illustrated) and takes—dependent upon its substance properties—a certain amount of energy from the Rayleigh waves traversing the test section 100. The thus altered Rayleigh wave is passed via the removal section 120 to the receiver $E_{RW}$ and is sensed there. In this connection it is significant that the feed section 110 and removal section 120 during the measurement process cannot come into contact with media which have good acoustic coupling properties and would thus lead to the uncoupling of wave energy.

The generally uniform Rayleigh-wave-guiding structure of this embodiment of the invention creates in itself relatively strong system boundaries which bring about wave-guiding properties of the entire acoustic transfer system 5, i.e. the wave energy generated by the sender $S_{RW}$ is so far as possible kept within the system boundaries and protected from external interference. A proportion of the wave energy left after the passage of the Rayleigh wave through the test section 100, at least sufficient for the measurement, is passed to the receiver $E_{RW}$. The wave-guiding property begins at least at the beginning of the test section 100 and continues up to the receiver $E_{RW}$. This includes both the forwarding or guiding of the use signal gained in the test section 100 with the lowest possible loss and protection against unwanted distortional influences. For the purpose of determining the dimension to be measured, only changes of at least one parameter of the Rayleigh wave are used, whereby preferably the dissipative energy loss of the Rayleigh wave in the test section serves as a basis for the evaluation.

A further fundamental characteristic of the wave-guiding property in the region of the test section consists in either preventing an uncoupling of energy through the vertical component of the Rayleigh wave into the contiguous liquid (due to the generation of compression waves), or in keeping the uncoupled energy so far as possible within the acoustic transfer system and passing it on to the $E_{RW}$. At least, however, the conditions to which the uncoupled energy is subjected should be known and be constant.

The uncoupling of compression waves into the liquid can occur through the above-described Variants 1 and 3. For example, uncoupling can occur by limiting the layer thickness of the liquid to be measured to a maximum of $l_{KW}/4$ of the compression wave and (if a solid borders the liquid layer) limiting the Rayleigh wave speed of the solid to fulfill the condition that total reflection is greater than the Rayleigh wave speed of the test section 100. Alternatively, or it can occur through the use of a material for the test section which has a Rayleigh wave speed smaller than the speed of the compression wave in the liquid. However, in the event that the afore-mentioned conditions cannot be fulfilled and a liquid layer with a thickness greater than $l_{KW}/4$ of the compression wave must be accepted, it can be ensured through the above-described Variant 2 that information about the dimensions of the liquid to be measured obtained through the interaction of the Rayleigh wave with the liquid is not lost and is contained in the use signal of the receiver. On the one hand this can be achieved through the use of a suitable solid positioned at a distance from the test section, where this solid re-captures the compression wave generated in the liquid and leaving the test section, and converts it on its surface to a Rayleigh wave. If the propagation stretch for the Rayleigh wave is sufficiently large on the opposite-lying solid, a compression wave is also generated from here and will again be captured by the opposite-lying test section 100. The Rayleigh-wave-guiding boundary layer of the second solid, thus analogous to the test section 100, influences the contiguous liquid and thus contributes to the measuring effect. A further possibility for ensuring the wave-guiding principles according to the invention consists in recording the compression wave leaving the test section 100 directly by a suitable receiver or via intermediate switching of a solid which is connected to a receiver. The influencing of the use signal through the wave-guiding properties of the acoustic transfer system should preferably be known, ideally be optimized.

In order to be able to achieve a sufficient measurement effect, the Rayleigh wave must be able to propagate on the test section 100 over at least 1/8, preferably however more than 2l.

The acoustic transfer system of FIG. 1b differs from that of FIG. 1a due to a sender $S_{VW}$ for volume sound waves, which emits sound waves evenly in all directions. A proportion of these volume sound waves meets with the mode converter 4 positioned at the beginning of the test section 100 where the volume sound waves are converted into Rayleigh waves. The energy transfer between the sender $S_{VW}$ and the mode converter 4 can take place via a solid or via a liquid. In order that the measurement effect can be evaluated, constant conditions in the area of the feed section 111 are necessary. Between the mode converter 4 and the receiver $E_{RW}$, the conditions prevail with wave-guiding property 130 as already described in connection with FIG. 1a.

The schematic representation of FIG. 1c shows an acoustic transfer system 5 with a sender $S_{VW}$ and a receiver $E_{VW}$ for volume sound waves and mode converters 4, 4' for converting volume sound waves into Rayleigh waves and vice versa, whereby these mode converters 4, 4' are positioned respectively at the beginning and end of the test section 100. Thus only the test section 100 transports Rayleigh waves. In addition, boundaries 131 from the receiver have been placed in a funnel-like way, whereby these boundaries 131 are supposed to sufficiently ensure the wave-guiding property of the field 130. They ensure that a sufficient proportion of the energy of the volume sound wave leaving the mode converter 4' in the direction of the receiver $E_{VW}$ is detectable and that the influence of distortional sources 60 is kept sufficiently low.

The following embodiments of the FIGS. 1d to 1m describe in a stylized form possibilities of the use of the Variant 1, whereby through limiting the layer thickness of the liquid to be measured to a maximum of 1/4 of the compression wave, an uncoupling of compression waves is prevented.

FIG. 1d shows a solid 1a, the ends of which carry a $S_{RW}/E_{RW}$ for Rayleigh waves RW which propagate in a boundary surface 11 lying on the surface 10. Side boundary elements 2'b channel the flow of a liquid layer 3a and thereby define the expanse of the test section 100, onto which on the right and left the feed section 110 and the removal section 120 connect. The thickness d of the liquid layer 3a is limited by a solid 2b lying opposite the test section 100. The solid 2b has a Rayleigh wave speed which is higher than that of the test section 100 so that the condition of total reflection is given. A medium 2a with a poor acoustic coupling ability, e.g. air, borders on the surface 10 of the solid 1a in the area of the feed section 110 and removal section 120. The boundary elements 2'b are formed in such a way that they essentially do not hinder the passage of the Rayleigh wave, in order that the information gained through the interaction of the Rayleigh wave with the liquid so far as possible is not distorted/weakened. If the liquid 3a which is to be measured is not under pressure, the boundary elements 2'b can be left out; the capillary effect will keep the liquid in the gap between the two solids.

For liquids with a sufficiently low viscosity, a tilted plane can also limit the thickness d of the liquid layer 3a, as is indicated in FIG. 1e. The test section 101 extends on the surface of the inclined solid 1b between the sender $S_{RW}$ and the receiver $E_{RW}$ without there being a feed section or removal section for the Rayleigh waves RW in-between. A variation of this principle lies in the use of centrifugal forces, whereby the solid 1b rotates around the rotation axis 140. Compared to the use of gravity-oriented measurement devices, much higher forces can be achieved through the centrifugal principle.

A further possibility for limiting the layer thickness d of the liquid layer 3a lies in the use of separating columns 150 (see FIG. 1f), which periodically pass over the test section of the acoustic transfer system and thereby ensure the necessary reduction of the layer thickness d to less than $l_{KW}/4$. An example of this embodiment is a mixed device (FIGS. 1g and 1h) with a circular-disc-form base (solid 1d) and contact rods (separating column 151) positioned so that they can rotate and the separating columns 151 form a narrow gap to the surface of the solid 1d, in which the sender $S_{RW}$ and the receiver $E_{RW}$ are situated. The feeding of the medium onto the mixed plane can take place through the hollow axis 151a. Depending upon the requirements and conditions of the individual case in question, the sender $S_{RW}$ and receiver $E_{RW}$ can be positioned radially (with test section 103) or in the circumference direction (with test section 102). In the first case the sender $S_{RW}$ and receiver $E_{RW}$ are spread over simultaneously by the separating column, whereas in the second case this occurs one after the other.

FIG. 1i shows two drums 1e and 1ee positioned at a distance from one another, which transport a paste-like or doughy medium 3 through the gap thereby formed. The medium is formed into an extensive formation which is lifted by a separating column 61 from the surface of the drum 1e. Sender $S_{RW}$ and receiver $E_{RW}$ are in this surface in the circumference direction. The boundary layer lying between the sender $S_{RW}$ and receiver $E_{RW}$ forms the test section 104. With each rotation of drum 1e, the test section 104 goes once into the area of the extensive formation 3a and can thus be used periodically for carrying out a measurement cycle. The layer thickness d of the formation 3a again lies under $l_{KW}/4$ of the compression wave in medium 3.

The device of FIG. 1j differs from the device described above in that it does not use mobile senders $S_{VW}$ and receivers $E_{VW}$, but instead uses stationary senders $S_{VW}$ and receivers $E_{VW}$. They are embedded in acoustic coupling components, which are connected to (edging) the surface of the drum 1f. Volume sound waves are activated in the acoustic coupling component 71 by the sender $S_{VW}$ (e.g. a oscillating crystal), and these volume sound waves in turn generate running Rayleigh waves in the boundary layer of the drum 1f. These propagate up to the acoustic coupling component 70 of the receiver $E_{VW}$, where they are converted into volume sound waves and sensed by the receiver $E_{VW}$. The test section extends from the gap between the drums 1f, 1ff to the positioning point of the coupling element 70.

FIG. 1k shows an embodiment similar to FIG. 1e with an inclined plane formed by a solid 1g. However, in this case the coupling of the acoustic energy takes place from the free liquid surface bordering on the medium 2a which has a poor acoustic coupling ability. For this purpose, two wedge converters 72, 73 are used, the wedge angles of which are precisely adapted to the Rayleigh wave to be generated. On the side opposite to the wave erection they carry oscillating crystals which serve as senders $S_{VW}$ and receivers $E_{VW}$. The volume sound waves generated in the wedge converter 72 by the oscillating crystal lead to compression waves in the liquid layer 3a, which in turn due to their angle of incidence on the solid surface activate Rayleigh waves RW. When the Rayleigh waves reach the area of the other wedge converter 73, they convert to compression waves again. The volume waves thereby activated in the wedge converter 73 are sensed by the receiver $E_{VW}$.

The application example of FIGS. 1l and 1m relates to a measurement installation for determining the viscosity of a medium 3 flowing in the channel 62 shortly before it leaves via a nozzle. In order to limit the layer density of the liquid 3a to be measured, a solid 2b is used, the Rayleigh wave speed of which is greater than that of the opposite-lying test section 106. Therefore, a close relationship to the measurement installation schematically represented in FIG. 1a exists. The solid 1h carrying the test section 106 has on one side a narrowing outer contour, which ends in a narrow frontal area. On to this is attached a sender-receiver unit $S_{VW}/E_{VW}$ for sending and receiving volume sound waves, which is periodically driven in send mode (FIG. 1l) and receive mode (FIG. 1m). On the opposite-lying side there is a mode converter 4, on which the volume sound waves are converted to Rayleigh waves. These propagate along the test section 106 and upon reaching the reflector 40 are reflected in such a way that they traverse the test section for a second time. On the mode converter 4 the Rayleigh wave "loaded" with the measurement information belonging to the liquid layer is then converted into a volume sound wave again which runs back in the direction of the sender-receiver unit.

The following embodiments of the invention of FIGS. 2a to 2i describe in a stylized form possibilities for use of Variant 2, whereby the compression wave uncoupled by the first wave-guiding solid into the contiguous liquid is again coupled into an opposite-lying solid. Through this "capture" of the uncoupling, the thickness of the liquid layer along the test section is not subject to any upper limit and can in particular be thicker than ¼ of the wavelength of the compression wave $l_{KW}$ in the liquid. This Variant 2 has three sub-variants, the first two consisting of coupling the compression wave to Rayleigh waves again. This coupling is achieved on an solid surface lying opposite of the test surface, which has the same Rayleigh wave speeds as the test surface, and lies parallel to it, or which has a reciprocal gradient adapted to the various speeds. The third sub-variant consists in coupling the compression wave into an opposite-lying solid which is connected to receivers or is itself a receiver for compression waves.

Thus FIG. 2a shows an acoustic transfer system 5 comprising a solid 1 and an opposite-lying solid 2c, whereby the two solids 1 and 2c have equal Rayleigh wave speeds $V_{(1)RW}=V_{(2)RW}$ and the surfaces of the two solids 1 and 2c lie parallel. Solid 1 carries on one end a sender for Rayleigh waves $S_{RW}$ and on its other end a receiver for Rayleigh waves $E_{RW}$. In the boundary layer 11 the Rayleigh wave RW propagates. Through side boundary elements 25 the liquid 3b to be measured is limited and thus the test section 100 is defined, whereby on this test section 100 on the left and right the feed section 110 and the removal section 120 connect. The thickness d of the liquid layer 3b must be thicker than the viscous boundary layer of the liquid and is not subject to any further condition. The solid boundary surfaces in the region of the feed and removal sections 110, 120, 220 border on a medium 2a with poor acoustic coupling ability (e.g. air or other gases). The boundary elements 25 are formed in such a way that essentially they do not hinder the passage of the Rayleigh wave, in order that the information gained through the interaction of the Rayleigh wave with the liquid so far as possible is not distorted/weakened. On the surface of the solid 2c lying opposite the solid 1 Rayleigh waves RW are activated which propagate in the boundary surface 21. These Rayleigh waves RW are activated through the compression waves KW in the liquid, which are activated by the Rayleigh wave RW in 11, which thereby weakens itself. The Rayleigh waves RW in 21 activate—thereby weakening themselves—for their part compression waves KW in the liquid, which again activate Rayleigh waves RW in 11. This thus gives rise to a mechanism for reciprocal activation of Rayleigh waves RW in the opposite-lying solid boundary surfaces 11,21, mediated through the compression waves KW in the liquid. A further test section 200 is defined through the part of the surface of 2c which touches the liquid 3b and the side boundaries 25. On this further test section 200 the removal section 220 connects on the right to a further receiver $E'_{RW}$. The illustrated measurement device is also able to function if only one of the two receivers $E_{RW}$, $E'_{RW}$ connected to the removal sections 120, 220 is used.

FIG. 2b shows the schematic representation of the gap between a screw conveyor moving inside a case 1 with the screw conveyor shoulder 2 and this case 1. Case 1 and screw conveyor shoulder 2 have the same Rayleigh wave speed $V_{(1)RW}=V_{(2)RW}$. Through a sender for Rayleigh waves $S_{RW}$, Rayleigh waves RW are generated on the case 1, whereby these Rayleigh waves RW propagate on the surface of the case 1 and thus define the test section 100. They thereby activate compression waves KW in the contiguous liquid 3. With uniform movement of the screw conveyor, at periodically recurring points in time, the screw conveyor shoulder 2 lies parallel opposite the test section 100 between sender $S_{RW}$ and receiver $E_{RW}$ as illustrated. This facilitates the activation of Rayleigh waves RW through compression waves KW on the screw conveyor shoulder 2. These Rayleigh waves RW propagating on the surface of 2 thereby define a further test section 200 and generate in turn compression waves KW in the liquid, which for their part activate Rayleigh waves on the case 1. The latter go into the receiver for Rayleigh waves $E_{RW}$ if there are suitable dimensions. The advantage of the sketched device consists in the use of existing components as carriers of the Rayleigh waves. The path of the acoustic (transfer from the sender $S_{RW}$ via Rayleigh waves RW on the case 1, compression waves KW in the liquid, Rayleigh waves RW on the screw conveyor shoulder 2, again compression waves KW in the liquid and again Rayleigh waves RW on the case 1, which finally go into the receiver $E_{RW}$) facilitates a signal transfer from sender to receiver, which would not be possible on the direct path via Rayleigh waves RW on the case 1. It would not be possible either because the distance of the signal transfer is too great and the radiation of compression waves would weaken the Rayleigh waves too much, or because a direct transfer from sender $S_{RW}$ to receiver $E_{RW}$ is not possible through an interruption 7 of the running section, e.g. through an opening.

FIG. 2c shows an acoustic transfer system 5 comprising a solid 1 and an opposite-lying solid 2d. The two solids 1 and 2d have differing Rayleigh wave speeds $V_{(1)RW} \neq V_{(2)RW}$ in such a way that an activation of Rayleigh waves RW is achieved in the boundary layer 21 of 2d through the compression waves KW. The compression waves KW activated by Rayleigh waves RW, which propagate in the boundary layer 11 on the solid 1, through the reciprocal gradient of the surfaces of solid 1 and 2d to one another at the gradient angle f. The solid 1 carries on one end a sender for Rayleigh waves $S_{RW}$ and on its other end a receiver for Rayleigh waves $E_{RW}$. Through side boundary elements 25, the liquid 3b to be measured is contained and thus defines the test section 100, which connects on the left and on the right to the feed section 110 and the removal section 120 respectively. Through the part of the surface of 2d touching the liquid 3b and the side boundaries 25 a further test section 200 is defined, on which on the right the removal section 220 connects to the receiver $E'_{RW}$. The thickness d of the liquid layer 3b must be thicker than the viscous boundary layer of the liquid and is not subject to any further condition. The solid boundary surfaces in the region of the feed and removal sections 110, 120, 220 border on a medium 2a with poor acoustic coupling ability (e.g. air or other gases). The boundary elements 25 are formed in such a way that they essentially do not hinder the passage of the Rayleigh wave, in order that the information gained through the interaction of the Rayleigh wave with the liquid so far as possible is not distorted/weakened. As already described in relation to FIG. 2a, the measurement device is also able to function if only one of the two receivers $E_{RW}$ or $E'_{RW}$ which lie on the solids 1 and 2d is used.

FIG. 2d shows the schematic representation of a sliding bearing in which there is a spindle 2. A part of the seat of the roller bearing 25 is formed as the solid 1 carrying the test section. The solid 1 carries both sender $S_{RW}$ and receiver $E_{RW}$ for Rayleigh waves RW, which propagate on the surface of the solid 1 along the connection section between sender and receiver, whereby the test section 100 is defined. The liquid 3 to be measured is in the gap between the solid 1 carrying the test section 100 and the spindle 2.

The Rayleigh wave propagating along the test section 100 brings about the activation of a (not illustrated) compression wave in the liquid 3. This in turn activates a further Rayleigh wave which propagates on the spindle 2 which lies parallel to the solid 1 and has the same Rayleigh wave speed $V_{(1)RW}=V_{(2)RW}$, whereby a further test section 200 lying opposite the test section 100 is formed. The Rayleigh wave on the spindle 2 activates for its part compression waves in the liquid 3, which again activate Rayleigh waves RW on the solid 1. The device of FIG. 2d facilitates the measurement of liquid properties directly in the gap of a sliding bearing using the surfaces of existing components as carriers of Rayleigh waves.

Instead of a sliding bearing for a rotating spindle, FIG. 2e shows the schematic representation of a sliding bearing for a piston 2 which slides forward and backward. A part of the cylinder 25 guiding the piston 2 is formed as a solid 1 carrying the test section. The solid 1 carries both sender $S_{RW}$ and receiver $E_{RW}$ for Rayleigh waves RW, which propagate on the surface of the solid 1 along the connection section between sender and receiver, whereby the test section 100 is defined. The liquid 3 to be measured is in the gap between the solid 1 and the piston 2. The Rayleigh wave propagating on the solid 1 brings about the activation of a (not illustrated) compression wave in the liquid 3. This in turn activates a further Rayleigh wave which propagates on the piston 2 which lies parallel to the solid 1 and has the same Rayleigh wave speed $V_{(1)RW}=V_{(2)RW}$, whereby a further test section 200 lying opposite the test section 100 is formed. The Rayleigh wave on the piston 2 activates for its part compression waves in 3, which again activate Rayleigh waves RW on the solid 1. As with the device of FIG. 2d, the device of FIG. 2e facilitates the measurement of liquid properties directly in the sliding gap using the surfaces of existing components as carriers of Rayleigh waves.

FIG. 2f shows an acoustic transfer system 5 comprising a solid 1 and an opposite-lying solid 2e, which has a lower speed $V_{(2)RW}$ for the Rayleigh wave than the Rayleigh wave speed of the solid 1 $V(1)RW$. This solid 1 has on one end a sender for Rayleigh waves $S_{RW}$. In the boundary layer 11 the Rayleigh wave RW propagates. Through side boundary elements 25, the liquid 3b to be measured is contained and thus the test section 100 is defined, on to which on the left the feed section 110 connects. The thickness d of the liquid layer 3b must be thicker than the viscous boundary layer of the liquid and is not subject to any further condition. The solid boundary surface in the region of the feed section 110 borders on a medium 2a with poor acoustic coupling ability (e.g. air or other gases). The boundary elements 25 are formed in such a way that they facilitate a good passage for the Rayleigh wave RW. On the surface of the solid 2e lying opposite the solid 1, volume sound waves SW are activated through the compression waves KW in the liquid, which are activated from the Rayleigh wave RW in the boundary layer 11, whereby the Rayleigh wave RW weakens itself. The sound waves SW thus activated propagate in the solid 2e in defined directions and go to receivers E and E' which are connected to the solid 2e.

FIG. 2g shows the schematic representation of a section of a pipe 27 carrying the measurement device, whereby the diameter of the pipe containing the liquid 3 is d. On a solid 1 integrated into the pipe wall, Rayleigh waves RW propagate, which are activated by a sender for Rayleigh waves $S_{RW}$ that is likewise integrated into the pipe wall. The length of the propagation stretch of the Rayleigh waves defines the test section 100. These Rayleigh waves bring about the activation of compression waves KW in the liquid which meet with the opposite-lying pipe wall and activate volume sound waves SW there in a suitable solid 2. These volume sound waves SW are taken from this solid 2 to a receiver $E_{SW}$. The illustrated section of a pipe can be formed in such a way that incorporation into existing systems is possible, whereby only a small change in cross-section is brought about.

The opposite-lying solid surface, with which the compression wave propagating in the liquid meets, can directly be the surface of a receiver for compression waves. Thus FIG. 2b shows an acoustic transfer system 5 comprising a solid 1 and an opposite-lying solid $E_{KW}$ which is a receiver for compression waves. This solid 1 carries on one end a sender for Rayleigh waves $S_{RW}$. In the boundary layer 1 the Rayleigh wave RW propagates, whereby its total propagation stretch defines the test section 100, to which on the left the feed section 110 connects. Through side boundary elements 25 the liquid 3b to be measured is limited. The thickness d of the liquid layer 3b must be thicker than the viscous boundary layer of the liquid and is not subject to any further condition. The solid boundary surface in the region of the feed section 110 borders on a medium 2a with poor acoustic coupling ability (e.g. air or other gases). The boundary elements 25 are formed in such a way that they facilitate a good passage for the Rayleigh wave RW.

FIG. 2i shows the schematic representation of a section of a pipe 27 carrying the measurement device, whereby the diameter of the pipe 27 containing the liquid 3 to be measured is d. Rayleigh waves RW propagate on a solid 1 integrated into the pipe wall, whereby these Rayleigh waves RW are activated by a sender for Rayleigh waves $S_{RW}$ which is likewise integrated into the pipe wall. The length of the propagation stretch of the Rayleigh waves defines the test section 100. These Rayleigh waves bring about the activation of compression waves KW in the liquid, which meet with a receiver for compression waves $E_{KW}$ lying in a pipe support connected to the opposite-lying pipe wall. The illustrated section of a pipe can be formed in such a way that incorporation into existing systems is possible, whereby only a small change in cross-section is brought about.

The following embodiments of FIGS. 3a to 3f describe in a stylised form the possibilities for use of Variant 3, whereby, as a wave-guiding solid surface, a material is used which has a lower speed for the propagation of Rayleigh waves than the speed of the compression waves in the contiguous liquid which is to be measured. The thickness of the liquid layer over the test section is thereby not subject to any upper limit, and can in particular be thicker than ¼ of the wavelength of the compression wave $l_{KW}$ in the liquid.

FIG. 3a shows an acoustic transfer system 5 comprising a solid 1, the Rayleigh wave speed $V_{(1)RW}$ of which is smaller than the compression wave speed $V_{KW}$ of the liquid 3b to be measured. Solid 1 carries on one end a sender for Rayleigh waves $S_{RW}$ and on its other end a receiver for Rayleigh waves $E_{RW}$. In the boundary layer 11 the Rayleigh wave RW propagates. Through side boundary elements 25 the liquid 3b to be measured is limited and thus the measurement stretch 100 is defined, on to which on the left and right the feed section 110 and the removal section 120 connect. The thickness of the liquid layer 3b must be greater than the viscous boundary layer of the liquid and is not subject to any further condition. The solid boundary surface in the region of the feed section 110 and removal section 120 borders on a medium 2a with poor acoustic coupling ability (e.g. air or other gases). The boundary elements 25 are formed in such a way that essentially they do not hinder the passage of the Rayleigh wave, in order that the information gained through the interaction of the Rayleigh wave with the liquid so far as possible is not distorted /weakened. This can for example be achieved through the use of dense materials like PU foam or rubber lips.

Rayleigh waves have the property of being physically bound to the surface of the solid guiding them. This wave-guiding takes place with virtually no losses and thus facilitates the use of geographically separated solids as carriers of the wave. The possible great geographical distance from the sender and receiver on the one hand and the test section on the other hand facilitates measurements at locations which can only be accessed with difficulty or at locations/in mediums in which there are conditions (e.g. high temperatures, chemical corrosivity, electromagnetic interference) to which the sender and/or receiver cannot be subjected. FIG. 3b shows a long lance-like solid 1 with a Rayleigh wave speed smaller than the speed of the compression wave in the liquid 3, one end of which carries sender $S_{RW}$ and receiver $E_{RW}$ for the Rayleigh waves RW and the other end of which immerses in the liquid 3 to be measured. The moistened part of the surface of the solid 1 carrying the Rayleigh wave RW forms the test section 100. The change of the parameters of the Rayleigh wave, which are brought about through the passage through the test section, depend upon the length of the test section and upon the properties of the liquid 3. Therefore, a device of the kind illustrated can be used either as a level sensor—namely when the liquid has constant properties (or the changing liquid properties do not influence the Rayleigh wave)—or when there is fixed immersion depth be used as a sensor for measuring the liquid properties (e.g. viscosity).

FIG. 3c shows a variant of the embodiment, which facilitates the measurement on a liquid in a separate receptacle. In the receptacle wall 25 a shell 27 is secured with a screw 26. This shell 27 serves as a carrier for a lance-like solid 1, which guides the Rayleigh wave and has a lower speed for the Rayleigh wave than the speed of the compression wave in the liquid. This solid 1 is secured in the shell 27 with a dense material 23 which allows the passage of the Rayleigh waves. Therefore, an installation is achieved whereby one end of the solid 1 guiding the Rayleigh wave is in contact with the liquid 3 to be measured and the other end carries a holder H with a sender $S_{RW}$ and receiver $E_{RW}$ for the Rayleigh waves. The illustrated formation of the solid 1 in the area of the conjugate holder H facilitates an easily manageable coupling of sender $S_{RW}$ and receiver $E_{RW}$ on the solid 1.

In FIG. 3d a measurement device is sketched which has on a one-component solid 1 guiding the Rayleigh wave two test sections 101 and 102. With one measurement device the properties of a liquid 3' in a pipe 27 can thereby be measured at two different points, before and after a reactor 61. The solid 1 has a Rayleigh wave speed which is smaller than the speed of the compression wave in the liquid 3'. The solid 1, which carries a bi-directional sender for Rayleigh waves $S_{RW}$ and a likewise bi-directional receiver for Rayleigh waves $E_{RW}$, penetrates the wall of the pipe 27 as illustrated in FIG. 3c. The asymmetrical positioning of the sender $S_{RW}$ gives rise to running stretches of varying lengths for the Rayleigh waves which traverse the test section 101/the Rayleigh waves which traverse the test section 102, whereby—with a pulsed send signal—the wave packets which have covered the paths of varying length meet with the receiver $E_{RW}$ at different points in time and can thus be recorded by a receiver with a time-triggered measurement. If sender $S_{RW}$ and receiver $E_{RW}$ for Rayleigh waves are symmetrically positioned, two separate receivers are necessary in order to differentiate between the signals of the two test sections 101 and 102. The measurement signal obtained can determine the operating conditions of the reactor 61 via a control device 62.

In FIG. 3e, an embodiment is schematically shown which integrates the measurement device into a pipe 27 containing the liquid 3', without reducing the cross-section of the pipe 27. Two pipe supports are positioned on the pipe 27, whereby one of these pipe supports carries the sender for the Rayleigh waves $S_{RW}$ and the other carries the receiver for the Rayleigh waves $E_{RW}$. $S_{RW}$ and $E_{RW}$ thereby lie outside the liquid 3' to be measured which is enclosed by the dense materials 23 sealing the pipe supports. These dense materials 23 are formed in such a way that they facilitate entry of the Rayleigh wave RW. The wave-guiding solid 1 is either formed from the pipe wall itself if this pipe wall consists of a material which has a lower speed for the Rayleigh wave $V_{(1)RW}$ than the speed of the compression wave $V_{KW}$ in the contiguous liquid 3', or it is formed from a material which is let into the pipe wall, is positioned on the pipe wall, or produced through the above-described appropriate change of the material of the pipe wall, whereby this material extends between sender $S_{RW}$ and receiver $E_{RW}$ and fulfils the cited speed condition $V_{(1)RW} < V_{KW}$. The running stretch of the Rayleigh wave RW, which lies within the two dense materials 23 and is moistened by the liquid 3', defines the test section 100. The illustrated pipe section can be incorporated into existing pipes with the flange connections 27'.

FIG. 3f shows that, analogous to the case illustrated in FIG. 3e with a closed pipe, the solid 1 guiding the Rayleigh wave can also be constituted by the wall of an existing receptacle 25 containing the liquid 3 to be measured. On the ends of the receptacle wall which are not moistened by the liquid 3, sender $S_{RW}$ and receiver $E_{RW}$ for the Rayleigh wave RW are positioned. The path of the Rayleigh wave on the receptacle wall takes place through the liquid 3, whereby the test section 100 is defined by the moistened part of the running stretch of the Rayleigh wave. The wave-guiding solid 1 is either formed from the receptacle wall itself if this consists of a material that has a lower speed for the Rayleigh wave $V_{(1)RW}$ than the speed of the compression wave $V_{KW}$ in the contiguous liquid 3, or it is formed from a material which is let into the receptacle wall, is positioned on the receptacle wall, or produced through the above-described appropriate change of the material of the receptacle wall whereby this material extends between sender $S_{RW}$ and receiver $E_{RW}$ and fulfills the cited speed condition $V_{(1)RW} < V_{KW}$. The receptacle 25 can be formed e.g. as a tank, a crucible or a channel containing a flowing liquid.

The FIGS. 4a to 4i described below show embodiments of the invention, which in addition to the acoustic energy, couple an additional energy form in the area of the test section.

According to FIG. 4a, the polar liquid is in an electric field activated from outside. According to their polarity, particles are thereby taken up by the electrode which is simultaneously a test section. Thus the proportion of selectively actuated polar particles can be controlled in front of the electrode and thus within the viscous boundary layer. The comparison of the measurement result of the Rayleigh wave propagation with and without electric field thus allows, e.g. an assertion concerning the ion content in a liquid.

According to FIG. 4b the electrode on the test section is interrupted several times, whereby each part electrode can be controlled with an individual signal. Various operating modes are possible:
  operation with direct or alternating current
  varying direct current potential on differing electrodes (concentration of polar particles)

all electrodes on the same direct current potential but varying alternating current potential (selective actuation of different polar particles via their characteristic (e.g. resonance) frequency generation of an electric "travelling wave" through phase-differing control (ji+1=ji+Dj with i=1 . . . n)

synchronizing this travelling wave with the propagation speed of the Rayleigh wave, e.g. so that the concentration of polar particles is at a maximum where the Rayleigh wave has a maximum deflection of the shear component and a minimum deflection of the compression component FIG. 4c shows the addition of thermal energy, e.g. electrically through resistive heating, in order to achieve a temperature gradient within the liquid. The temperature of the test section $T_{MS}$ is higher than that of the environment Tu.

Therefore, different effects can be produced:

effect upon chemical processes or reactions, which bring about a viscosity change through the addition of thermal energy targeted change of the viscosity distribution (viscosity gradient) via the temperature, e.g. for applications in the field of process engineering (extruder)

FIG. 4d shows a possibility for introducing mechanical (acoustic) energy into the liquid, in order to e.g. accelerate (chemical) processes, or e.g. in order to achieve a purification effect (ultrasound purification). The "purification success" can be determined by change in the concentration/composition/precipitation on the test section. Vice versa, a desired mixing can be produced, e.g. of an emulsion dependent upon the concentration-dependent viscosity ascertained on the test section.

The mechanical change of the form of the test section through mechanical intervention, as is shown in the principle representation of FIG. 4e, has advantages relating to the following:

a mixing of the liquid is possible a pump effect is possible a longer running stretch of the Rayleigh wave is produced (if $l_{MS}>>l_{RW}$)

FIG. 4f indicates the possibility of temperature control through the measurement of the viscosity. For example, temperature-dependent processes can be controlled in a contact mechanism. Control of the temperature via the measurement of the viscosity can also take place using a cooling element (e.g. a Peltier element) (see FIG. $4_g$). Possible applications are e.g. in quality checking and control of a cooling system.

FIG. 4h shows the schematic structure of a measurement device on a transparent solid 1. This solid 1 carries on one end a sender for Rayleigh waves $S_{RW}$ and on its other end a receiver for Rayleigh waves $E_{RW}$. Between the two, the Rayleigh wave RW propagates on the surface of solid 1. Through side boundary elements 25, the liquid 3 to be measured is limited and thus the test section 100 is defined. The boundary elements 25 are formed in such a way that they essentially do not hinder the passage of the Rayleigh wave. Through the transparent solid 1, light 7 enters from below and thus brings an additional energy inflow into the vicinity of the test section 100. Through this optical activation, reactions can be triggered in photo-active liquids or in photo-active solids which are distributed in the liquid. Changes in liquid properties thereby brought about can be measured with the acoustic measurement system. If the measurement device is constructed using a non-transparent solid, the light inflow can in certain circumstances take place from another direction. Using lasers, optical energy can be concentrated in very narrow ray bundles in a narrow area, and thus the test section is only partly supplied with optical energy.

FIG. 4i shows schematically the structure of an acoustic test section on a transparent carrier material for use under a microscope. On an object carrier 1 there is a sender for Rayleigh waves $S_{RW}$ on the left and on the right a receiver for Rayleigh waves $E_{RW}$. The trial liquid 3 to be investigated lies between them and is covered by a covering glass 2. This installation facilitates the measurement of a liquid properties or changes in such properties, for example of biological or biochemical liquids, and the simultaneous optical observation of these liquids with a microscope 6. The device can advantageously be used when the light 7 which is necessary for optical observation acts as a trigger for photochemical processes in the trial liquid 3 and the changes thereby brought about in liquid properties can be measured with the acoustic transfer system.

In FIGS. 5a to 5c, devices according to the invention are schematically illustrated with several test sections. In FIG. 5a the Rayleigh wave RW leaving a sender for Rayleigh waves S goes via a feed section 110 to a first test section 100. After the passage through this test section, the Rayleigh waves go via a section with wave-guiding property 130 to a second test section 101 and from here further via a section with wave-guiding property to a third test section 102. From the end of this test section the Rayleigh waves are passed via a removal section 120 to the receiver E. In practical use, such an installation is found with the level observation of several tanks separated from one another with identical liquids. If the test sections are identically formed, one receives clearly differing receiver signals in the case of 0, 1, 2 or 3 test sections being in contact with the liquid.

A further schematic representation of a configuration according to the invention is illustrated in FIG. 5b. Here, the Rayleigh waves RW leaving a sender for Rayleigh waves S are guided via a feed section 110 to the test sections 100, 101 and 102, and after passing through the respective test section are fed via removal section 120, 121, 122 to the receivers $E_1$, $E_2$ and $E_3$. In practical use, such an installation is found with two test sections in the case of a device according to the invention with a first test section 100 which can be brought into contact with the medium to be measured and a second test section 101 which serves as a reference section and cannot be brought into contact with the medium. Such an installation with a reference section is used particularly if the change in the measurement signal in receiver $E_1$ brought about by the liquid is small compared with other influences like for example signal changes through temperature fluctuations. In both FIG. 5a and FIG. 5b the number of test sections used can be selected as one wishes. In FIG. 5c an installation is schematically illustrated whereby Rayleigh waves leaving a sender S are fed via feed sections 110 and 111 to the test sections 100 and 101, and from here are fed via removal sections 120 and 121 to a single receiver E. If the test sections 100 and 101 have the same formation and if the Rayleigh wave running time on the section 110–120 differs from the Rayleigh wave running time on the section 111–121, when there is pulsed operation of the sender, via the running time differences of the Rayleigh waves, physical or technical parameters of the liquids moistening the test sections 100 and 101 can be derived using a single receiver.

In FIGS. 5d and 5e, two embodiments of configurations of test sections from FIGS. 5a to 5c are represented. FIG. 5d shows a configuration according to the schematic representation in FIG. 5b. On a solid 1 there is a Rayleigh wave sender $S_{RW}$, from which Rayleigh waves RW are sent to the test sections 100, 101 and 103. Via removal sections 120, 121 and 122, the Rayleigh waves are fed to the receivers $E_1$, $E_2$ and $E_3$. The sections with wave-guiding properties 100–120, 101–121 and 102–122 are, in the example of FIGS. 5d and 5e, separated from one another by grooves. The Rayleigh waves are passed on the solid surface 10 of each test section between the grooves and fed to the respective receiver. If the test sections 100, 101 and 102 are formed from various suitable materials, the liquid on the test sections can be identified as one of several possible liquids.

FIG. 5e illustrates a section of an embodiment of a configuration according to the invention for the determination of a physical or technical parameter of a lubricant substance in a sliding bearing. Inside a bearing bush L, a spindle W is positioned in such a way that it can rotate, whereby between the spindle W and the bearing bush L, lubricant S is used to reduce the sliding friction. Volume waves are passed from a sender $S_{SW}$ for sound waves to a mode converter 4, which generates Rayleigh waves on the inner side of the bearing bush L. These Rayleigh waves are converted into a volume wave in a second mode converter 4', and after passing through the bearing bush L meet with a receiver $E_{SW}$ for volume waves. In this example, the gap filled with lubricant between the bush and the spindle functions as the test section. The thickness of the lubricant must thereby as a rule not be small in relation to the Rayleigh wavelength, as in this case there is a configuration as described in Variant 3.

In FIG. 5f, an installation according to the invention with parallel test sections M1, M2 using mode conversion in the wave guide is illustrated. By means of a sender for volume sound waves $S_{SW}$ sound waves are coupled into the solid 1. They meet on the surface 10 of the solid 1 with a mode converter 4, from which Rayleigh waves RW1 and RW2 propagate. The Rayleigh waves are converted back into volume sound waves SW on mode converters 4' and 4" and are received in receivers for volume sound waves $E_{SW}$. In the illustrated embodiment, a Rayleigh wave $RW_1$ runs in the test section M1, which is in contact with the liquid to be measured 2, and the other test section M2 runs on a boundary surface of the solid 1 to air or vacuum. The test section M2 serves preferably as a reference section for the test section M1.

FIG. 5g illustrates an embodiment for the incorporation of a measurement device according to the invention into the wall W of a pipe. The test section 100 is on the outer side of a rod-shaped solid 1, one end of which immerses in the liquid 2 to be measured in the pipe. The solid 1 is separated from the flange F by an insulating material 1, into which the Rayleigh waves RW running on the surface of the solid 1 cannot couple. On the other end of the solid 1, there is a sender $S_{SW}$ for volume sound waves SW. Volume sound waves SW from this sender $S_{SW}$ propagate within the solid 1 and meet with a mode converter 4, from where Rayleigh waves RW propagate along the surface 10. The Rayleigh waves RW1 and RW2 are received by means of Rayleigh wave receivers $E_1$ and $E_2$ on the end of the solid 1 lying away from the pipe wall W. The configuration is selected in such a way that the Rayleigh wave RW2 runs on the part of the solid surface 10 which does not come into contact with the liquid 2 to be measured and which is separated from this by a sound insulator l, into which the RW2 cannot couple. When the measurement results are evaluated, the signal of the receiver E2 is used as a reference value for the conversion efficiency of the mode converter 4. RW1 runs at least partly in an area which is in contact with the liquid 2 and forms the test section 100.

FIGS. 5h and 5i shows examples of wave guides, on which Rayleigh waves RW on their way from the sender to the receiver are reflected at least once. FIG. 5h illustrates the surface of an essentially U-shaped solid carrying Rayleigh waves. A Rayleigh wave propagates in one side of the U along a wave guide which contains the test section M and meets with a limitation B of the solid preferably positioned under 45 degrees. The level Rayleigh waves are reflected on this, meet with the opposite-lying limitation edge B' and are reflected into the other side of the U. FIG. 5i shows a configuration with the same form of wave guide, whereby the Rayleigh wave on the solid surface 10 is passed to grooves N, the depth of which corresponds at least to the wavelength of the Rayleigh wave. Grooves of this nature can either be incorporated mechanically into a solid, be produced during the manufacturing process of the wave guide through injection molding, or, for example, be produced on a solid surface through photo-etching. In FIGS. 5h and 5i, the Rayleigh wave is reflected twice, in order to get from the sender to the location of the receiver. According to the laws of optics of even waves, wave guides with one reflecting limitation (V-shaped wave guide) or with more than two reflecting limitations can also be formed. Likewise a wave guide according to the invention is constituted by a solid surface whereby after the passage of the Rayleigh wave through the test section, there is a grid for Rayleigh waves perpendicular to the propagation direction of the Rayleigh waves. An installation of this nature is useful if the Rayleigh wave leaving a test section has a broad wave front, the energy of which is to be fed almost entirely to a receiver which is small in comparison therewith. Likewise wave guides are conceivable whereby after the passage of the Rayleigh wave through the test section the surface of the wave guide carries a converging lens for Rayleigh waves, in which the Rayleigh waves are diffracted to the receiver. In particular, the test section can be formed as a lens for Rayleigh waves.

FIGS. 5h and 5j show an installation of a solid 1 carrying Rayleigh waves RW and a compact sender-receiver installation. A switch carrier ST is acoustically coupled to the solid 1 (for example using mode converters). This switch carrier ST carries a sender S, the electronic switching SE necessary for the operation of the sender, the receiver E and the electronic switching EE necessary for the operation of the receiver, an interface and evaluation switch, which via a contact strip K is connected to a voltage supply and an evaluation and control system. A switch of this nature can, for example, be positioned as a dense layer switch on a ceramic switch carrier ST which has wave-guiding properties. Such a configuration of compact electronics and a wave-guide for Rayleigh waves loosely connected thereto is preferably used when the wave guide must be exchanged after a measurement process (e.g. with the measurement of irreversible polymerization processes in the liquid). In such exceptional cases the wave guide which can be cost-effectively manufactured is designed for once-only use.

At the beginning it was pointed out that the invention facilitates the integration of the test section into an existing device, for example into the wall of a working machine or a pipe, and thus allows on-line measurements directly at the locations where the evaluation of the liquid properties is of prime importance. In order to be able to ensure the physical separation, if necessary, of the test section on the one hand and the sender/receiver on the other hand, one embodiment of the invention suggests the use of the principle of mode conversion, which is explained below with various embodiments of the invention.

The block wiring diagram of FIG. 14a uses a sender 1 for generating volume sound waves VW, which propagate in a body guiding acoustic waves until they reach a mode converter 3. This mode converter 3 which is in connection with the test section 5' converts the energy of the volume sound waves largely into Rayleigh waves. The part of the boundary layer of the body concerned is in contact with the liquid to be measured and forms the test section. As the Rayleigh waves propagate in the boundary layer the liquid properties (e.g. density and viscosity) influence the parameters of the Rayleigh wave, and a measurable signal change occurs. At the end of the area 5 to be monitored there is a second mode converter 4 for re-converting the arriving Rayleigh waves into volume sound waves which propagate in the direction of the separate receiver 2.

FIG. 14b shows a block wiring diagram with only one mode converter 4 (between test section 5' and the receiver 2) for converting Rayleigh waves RW into volume sound waves VW. The sender 1' generates the Rayleigh waves RW directly at one end of the test section 5' or on a boundary surface which is in a wave-guiding connection with the test section 5'.

FIGS. 14c and 14d again use senders 1 which generate volume sound waves VW. Allocated to the senders 1 in a working connection with the test section 5' is a mode converter 3 for converting volume sound waves VW into Rayleigh waves VW. Mechanical-electrical converters are provided as receivers 2', whereby these mechanical-electrical converters can sense the Rayleigh waves and are positioned at the end of the test section 5' or on a boundary surface which has a wave-guiding connection to the test section 5'. According to FIG. 14d, in the propagation path of the Rayleigh wave there is additionally a reflector 6, which can for example be in the form of an indentation or a slit.

The embodiment of the invention shown in FIG. 14e uses a one-component sender-receiver unit 12, consisting of a sender 1 and a receiver 2. If send mode and receive mode occur at a time distance apart, the same oscillating crystal or shear vibrator can be used for sender 1 and receiver 2. It would generate and receive volume sound waves alternately. A common mode converter 34 is allocated to this sender-receiver unit, whereby the mode converter 34 works in two propagation directions. First, the mode converter 34 converts the volume sound waves VW generated in the send mode into a Rayleigh wave RW, which propagates along the test section 5' until it reaches the reflector 6. After its reflection and return along the test section 5', the reflected Rayleigh wave RW is converted back into a volume sound wave VW which is sensed upon reaching the receiver 2 (or the one-component converter during the receive mode).

FIGS. 6 to 9 show various configurations of mode converters, the sender-receiver characteristic of which is partly direction-indifferent and partly direction-dependent.

In the embodiment of the invention according to FIG. 6, the mode converter 34' divides the test section 5' into a left section and a right section, whereby the outer edges thereof are each flanked by an indentation which function as reflectors for the Rayleigh waves leaving the mode converter 34'. The sender-receiver unit 12' works cyclically in send or receive mode, whereby volume sound waves are generated or received. In FIG. 6, the wave propagation and mode conversion in the body 5 of the test section 5' is shown schematically. The volume sound wave leaving the sender-receiver unit with the propagation direction 10 reaches, in the vicinity of the boundary surface of the test section 5; the mode converter 34; which consists of a series of holes. When the volume sound wave passes through the grid-like mode converter 34', an elementary wave 100' is formed at each gap, whereby the superposition of this elementary wave 100' on the disc upper edge 5' finally leads to the formation of Rayleigh waves. The Rayleigh wave propagates from the mode converter 34' positioned at one end of the test section 5' along its path 10' to a reflector formed as an indentation.

In order to achieve a high efficiency rate of the mode converter 34', it must be ensured that the division t of the individual holes of the series of holes, thus their distance from one another, corresponds as exactly as possible to the wavelength l of the Rayleigh wave to be generated. The distance s of the mode converter 34' from the area 5' to be monitored should be experimentally determined. It is ideal when the superposition of the elementary waves 100' leads to a maximum formation of Rayleigh waves.

The embodiment of the invention of FIG. 7 differs from the embodiment according to FIG. 6 exclusively through the type of mode converter 34' which has been incorporated directly into the contour of the test section 5' It takes the form of a row of wedge-like hollows. The division of the individual hollows corresponds—as with the series of holes 34'– to the wavelength l of the Rayleigh wave to be generated. Its depth d should amount to d≈l/2 with a symmetrical indentation form. With symmetrical formation of the periodic indentations, the mode converter 34' is suited equally to the generation and reception of Rayleigh waves for the purpose of mode conversion. With an asymmetrical formation of the indentations, for example, whereby one of the wedge sides has a flatter angle with the boundary surface plane than the other wedge side, the generation of the Rayleigh wave occurs preferably in the direction of the flatter angle. The reception of the Rayleigh wave is preferably from the opposite direction.

In order to protect the mode converter 34" from soiling, its indentations should be filled with a material whose acoustic properties differ considerably from those of the material of the test section. This step can also be used to protect the slit-like reflectors.

FIG. 8 shows a mode converter 34''' consisting of several individual components positioned on the test section. The distance between the individual components again corresponds to the wavelength l of the Rayleigh wave to be generated. Compared to the embodiments of FIGS. 6 and 7, this embodiment of the invention has the advantage that there does not have to be any intervention into the material of the test section. The sender plane of the opposite-lying sender-receiver unit 12 is positioned at a gradient in relation to the plane of the mode converter 34''' and the test section 5' carrying it. Therefore, the emitted Rayleigh waves meet with the mode converter 34''' at a corresponding angle, which leads to a preferred propagation direction 10' of the Rayleigh waves generated there.

Even the reception of the Rayleigh wave and its conversion back into a volume sound wave is preferred from this direction. Therefore, such a mode converter 34''' should be positioned at the end of the test section 5', whereas the other end of the measuring area 5' is flanked by a reflector.

FIG. 9 shows a mode converter with a similar sender-receiver member 12. It has a wedge-like form and is securely connected to the test section 5' via a coupling surface 50. Slits 340 are angularly incorporated into the allocated coupling surface 341 of the mode converter 34'''', whereby the distance between the slits 340 corresponds approximately to the wavelength l of the Rayleigh wave. The volume sound waves are firstly broken on the boundary surface (coupling surfaces 50, 341) between the body 5 of the measuring area 5' and the mode converter 34''" in the direction of the slit 340, before they are reflected there and finally coupled again into the body 5. The superposition of the reflected waves leads to the formation of the desired Rayleigh wave.

The FIGS. 10 to 13 described below show a small selection of measuring installations with differing combinations of senders, receivers and mode converters. Many other measuring configurations are within the scope of the invention. However, these do not make any further significant contribution to the understanding of the invention. The selection of an embodiment of the invention and its tangible form should always be oriented towards the requirements of the specific case in question. In addition, technical steps are described which in particular are suitable for improving the signal-noise ratio and thus for increasing the measurement accuracy.

FIG. 10 shows in a strongly schematic form a measuring installation with a solid 5. The liquid 7 to be measured borders the test section 5'. The mode converters 3,4 form the edges of the test section 5'. Their representation is understood as a symbol which can stand for any of the embodiments of mode converters described in FIGS. 6 to 9. On the opposite side of the solid 5, sender 1 and receiver 2 are positioned, which e.g. can be formed as simple flexure crystals. A proportion of the volume sound waves activated by sender 1 in the solid 5 reaches the mode converter 3, where a conversion into Rayleigh waves RW occurs, and whereby these Rayleigh waves RW propagate along the test section 5' in the direction of the other mode converter 4. They thereby interact with the contiguous liquid 7. The thus altered Rayleigh wave RW is converted back into a volume wave VW by the mode converter 4 and is sensed by the receiver 2. If the process conditions allow it, the solid 5 forming the test section 5' should have a Rayleigh wave speed which is smaller than the sound speed of the compression wave in the liquid 7. The otherwise unavoidable uncoupling of compression waves KW and the considerable energy loss associated therewith is thereby prevented.

A further possibility for making the energy used for the measurement purpose as extensively usable as possible consists in the limitation of the liquid layer to a density under $l_{KW}/4$ of the compression wave KW in the liquid as shown in FIG. 11. If this is to occur by means of a gap, then the Rayleigh wave speed of the solid 5a lying opposite the test section 5' must be greater than that of the test section 5' itself, so that the conditions for total reflection are fulfilled.

Accordingly, a solid 5 is provided with an opposite-lying solid 5a bordering on a gap which is divided into a left and a right section by means of a division element 8. A test section 5'a, 5'b is allocated to each section of the gap, whereby these test sections 5'a, 5'b extend right and left of the common mode converter 34 to the reflectors 6a, 6b which are incorporated on the edge. The mode converter 34 divides the area between the reflectors 6a, 6b asymmetrically into two sections which are unequal in length, in such a way that the running times of the signals are correspondingly different and can thus be evaluated separately. In order to avoid hindering the formation and propagation of the Rayleigh waves, the division element preferably consists of a material with poor acoustic coupling ability, e.g. polyurethane or rubber.

In order to manage with a one-component sender-receiver unit 12, the unit 12 must work in pulsed operation, i.e. the unit 12 works alternately as a sender and receiver. Through a send pulse, in the solid 5 volume sound waves VW are activated which upon passing through the mode converter 34 are converted into Rayleigh waves RW. As the mode converter 34 does not have a preferred propagation characteristic for Rayleigh waves, the Rayleigh wave RW propagating to the left has around the same energy content as the Rayleigh wave propagating to the right. After their reflection on the reflectors 6a, 6b the Rayleigh waves RW cross the test sections 5'a, 5'b for a second time. Due to the smaller expanse of the test section 5'b, the Rayleigh wave RW which is reflected on the reflector 6b and changed through the interaction with the liquid 7 reaches the mode converter 34 before the Rayleigh wave RW reflected on the reflector 6a, and is converted back into a volume sound wave VW there. It reaches the sender-receiver unit 12 before the signal of the other test section 6a, in such a way that a clear signal classification and evaluation is possible.

FIGS. 12a to 12c show embodiments of a measuring installation with a solid 5a lying opposite the test section, whereby the Rayleigh wave speed of the solid 5a corresponds to that of the test section. The gap in-between for the liquid 7 to be measured can definitely be greater than $l_{KW}/4$ of the compression wave KW in the liquid 7 without risking an unjustifiably large energy loss, as the energy uncoupled by the Rayleigh wave RW—which migrates in the form of compression waves KW through the liquid 7 to the opposite-lying solid surface—is for a large part "captured" again and for its part activates Rayleigh waves RW on this opposite-lying solid surface. These Rayleigh waves again initiate compression waves KW which turn back and activate Rayleigh waves RW again. Through this reciprocal "cross-induction" of acoustic energy not only wave-guiding-like properties of the measuring installation are created; the binding-in of a Rayleigh-wave-guiding additional solid 5a also increases the length of the effective test section. The degree of the reciprocal "cross-induction" of acoustic energy depends to the greatest extent upon the constructive formation of the measuring installation, and is determined essentially by the distance of the opposite-lying solids 5, 5a and the length of the test section.

According to FIG. 12a, a sender 1' is used for the generation of Rayleigh waves RW which propagate along the test section up to the mode converter 4. In this way, through acoustic "cross-induction" interactions with the opposite-lying solid 5a are brought about. During its passage through the mode converter 4 the Rayleigh wave RW converts to a volume sound wave VW in the solid 5 and can be sensed by the receiver 2, e.g. in the form of a flexure crystal.

The embodiment of FIG. 12b hardly differs from the above-described measuring installation in its mode of operation. The sender and receiver have merely been exchanged. i.e. a sender for volume sound waves VW is positioned on the solid 5 opposite the mode converter 3 (and the test section). The volume sound wave VW is converted to a Rayleigh wave RW and sensed by a receiver for Rayleigh waves positioned at the end of the test section.

The special feature of the embodiment of FIG. 12c is that the opposite-lying solid 5a is incorporated into the measuring installation not only as a passive component but as an active component. Accordingly, a sender 1' for Rayleigh waves RW is positioned in the opposite-lying solid 5a, from where acoustic energy cross-inducts onto the boundary layer of the solid 5 and activates Rayleigh waves RW there. These are converted by the mode converter 4 to volume sound waves VW and are sensed by the receiver 2.

It should be pointed out here that the principal construction of the measuring installations of FIGS. 12a to 12c can also be equipped with several mode converters. However, it must be borne in mind that losses are connected to each mode conversion and these can have a negative effect upon the measurement process.

In the event that the material properties (Rayleigh wave speed) and/or the gradient of the boundary surfaces of the opposite-lying solids which is necessary for the "cross-induction" of acoustic energy cannot be adapted to the requirements, it is possible to use the principle illustrated in FIG. 13. It is based upon the observation that compression waves KW in the liquid in a comparably wide angle area of their incidence on a solid are in a position to couple a sufficiently large amount of energy. The schematic representation of FIG. 13 shows a first solid 5 with a sender 1' for Rayleigh waves RW which propagate along the test section 5'. The energy coupled through the vertical component of the Rayleigh wave RW and converted into a compression wave KW of the liquid meets at a certain distance with the surface of a curved (or positioned at a gradient) second solid 5a. Through the mode converter 3 placed on the surface part of the energy of the volume sound wave KW is converted into Rayleigh wave energy, which propagates in the boundary layer of the solid 5a up to the receiver 2. As with FIG. 12c, the boundary surfaces of both solids 5, 5a contribute to the measuring effect.

We claim:

1. A method for measuring physical characteristics or physical properties of liquids comprising:
   providing an acoustic transfer system having at least one receiver and at least one test section formed from a solid surface made from non-piezo-electric material that is brought at least partly into contact with a liquid to be measured,
   feeding acoustic wave energy to the test section by a sender, wherein at least part of the acoustic wave energy is made available in the form of at least one Rayleigh wave,
   propagating the Rayleigh wave on the test section over at least an eighth of its wavelength,
   passing at least part of the acoustic wave energy leaving the sender through a mode converter at least once on its way to the receiver, and
   converting the part of the acoustic wave energy passing through the mode converter at least partly from one of a Rayleigh wave and a volume soundwave into the other of a Rayleigh wave and a volume sound wave, and
   determining from the acoustic wave energy received by the receiver the physical characteristics or physical properties of the liquid to be measured by using changes of at least one parameter of the Rayleigh wave as a basis.

2. A method according to claim 1 wherein volume soundwaves are activated by the sender in the solid carrying the test section, whereby these volume soundwaves are converted into Rayleigh waves by a mode converter situated in close proximity to the test section, whereby the Rayleigh waves then traverse the test section.

3. A method according to claim 2 wherein after passing through the test section the Rayleigh waves are converted back into volume soundwaves by a second mode converter connecting to the test section, whereby these volume soundwaves propagate up to a volume-soundwave-sensitive receiver.

4. A method according to claim 2 wherein after passing through the test section, the Rayleigh waves are sensed by a Rayleigh-wave-sensitive receiver either directly or after passing through a removal section connected to the test section.

5. A method according to claim 2 wherein after passing through the test section, the Rayleigh waves are reflected in such a way that they pass through the test section for a second time in the opposite direction, and meet with the mode converter again, which converts the returning Rayleigh wave again into a volume soundwave which propagates up to the receiver, wherein the wave activation takes place in a pulsed way.

6. A method according to claim 1 wherein Rayleigh waves are activated by the sender in the test section or in a feed section connected thereto, whereby these Rayleigh waves, after passing through the test section, are converted into volume soundwaves by the mode converter and are passed on to the receiver.

7. A method according to claim 1 wherein dissipative energy loss of the Rayleigh wave in the test section is the only parameter used to determine the physical characteristics or physical properties to be measured.

8. A method according to claim 1 wherein the layer thickness or the liquid to be measured on the test section is greater than the viscous boundary layer thickness and less than the liquid layer necessary for formation of the fundamental vibration of a stationary compression wave.

9. A method according to claim 8 wherein the thickness of the layer to be measured is limited by a gap which on one side is limited by the test section and on the other side by an opposite-lying solid whose Rayleigh wave speed is greater than that of the test section.

10. The method of claim 8 wherein the thickness of the liquid layer is less than one quarter of the wavelength of the compression wave.

11. A method according to claim 1 wherein on the solid surface of the test section, the Rayleigh waves are converted into compression waves and radiated into the liquid to be measured, the liquid having a layer thickness greater than a quarter of the wavelength of the compression wave, and the compression waves are as completely as possible captured by a solid surface positioned at a distance to the test section.

12. A method according to claim 1 wherein for the test section, a solid is used whose Rayleigh wave speed is smaller than the sound speed of the compression wave in the liquid to be measured.

13. A method according to claim 1 wherein the acoustic transfer system works according to the principle of a wave guide at least between the beginning and end of the test section, whereby an uncoupling of energy from the Rayleigh wave into the medium to be measured which does not serve the measurement is suppressed, or energy uncoupled from the Rayleigh wave is fed to the receiver.

14. The method of claim 1 wherein the liquid to be measured is highly viscous, doughy or paste-like.

15. The method of claim 1 wherein the device is a working machine, a receptacle, or a transport system.

16. The method of claim 1 wherein the Rayleigh wave propagates over at least twice its wavelength.

17. A device for measuring physical characteristics or physical properties of liquids comprising:
   an acoustic transfer system having at least one receiver and at least one test section formed from a solid surface made from non-piezo-electric material that, when a liquid is being measured, can be brought at least partly into contact with the liquid, and is a functional component of a device, and
   a sender by which acoustic energy is fed to the test section, wherein the test section is suitable for passing on Rayleigh waves (RW) at least an eighth of the wavelength of the Rayleigh wave, at least one mode converter operably connected to the test section, whereby the mode converter converts at least one of a volume soundwave running from the sender to the test section into a Rayleigh wave (RW) or a Rayleigh wave running from the test section to the receiver into a volume soundwave, and wherein the device is formed in such a way that when a liquid is being measured, changes of at least one parameter of the Rayleigh wave (RW) are used as a basis to determine the physical characteristics or physical properties of the liquid.

18. A device according to claim 17 wherein the sender and receiver are positioned on the opposite side of the solid carrying the test section and are in a volume soundwave conductive connection with mode converters provided at at least one of the beginning and end of the test section.

19. A device according to claim 17 wherein the sender and receiver are formed as a one-component unit and are positioned on the side opposite of the solid carrying the test section, and are in a volume soundwave conductive connection with a mode converter provided at the beginning of the test section, and wherein at the end of the test section a reflector is provided which reflects the Rayleigh wave in the direction of the mode converter.

20. A device according to claim 17 wherein the mode converter consists of several periodically positioned elements, which are positioned along the propagation direction of the Rayleigh wave at a distance which approximately corresponds to the wavelength of the Rayleigh wave.

21. A device according to claim 17 wherein the mode converter is in the form of a series of holes in the vicinity of the boundary surface of the solid forming or carrying the test section.

22. A device according to claim 20 wherein the mode converter is in the form of periodically-positioned, symmetrically or asymmetrically formed teeth or indentations in the surface of the solid forming or carrying the test section.

23. A device according to claim 20 wherein the mode converter is formed from additional separate components which are positioned on the surface of the solid forming or carrying the test section.

24. A device according to claim 23 wherein the mode converter is formed from individual components which are connected at a distance of one wavelength of the Rayleigh waves securely to the surface of the solid carrying the test section, whereby the send direction of the volume soundwave runs at a gradient to the solid surface.

25. A device according to claim 17 wherein the thickness of a liquid layer to be measured on the test section is greater than the viscous border layer thickness and less than the thickness of the liquid layer necessary for the formation of the fundamental vibration of a stationary compression wave.

26. The device of claim 25 wherein the thickness of the liquid layer is less than one quarter of the wavelength of the compression wave.

27. A device according to claim 17 wherein the sender and receiver are formed as a one-component unit and the unit is driven alternately in send mode and receive mode.

28. The device of claim 17 wherein the liquid to be measured is highly viscous, doughy or paste-like.

29. The device of claim 17 wherein the functional component is on a working machine, a receptacle, or a transport system.

30. The device of claim 17 wherein the test section is at least twice the length of the Rayleigh wavelength.

* * * * *